US012570627B2

(12) United States Patent
Ochii et al.

(10) Patent No.: US 12,570,627 B2
(45) Date of Patent: Mar. 10, 2026

(54) PHARMACEUTICAL COMPOSITION IN WHICH PRODUCTION OF IMPURITIES IS SUPPRESSED

(71) Applicant: Shionogi & Co., Ltd., Osaka (JP)

(72) Inventors: Yuya Ochii, Osaka (JP); Chika Nishida, Tokyo (JP); Go Kimura, Hyogo (JP); Shinichi Oda, Hyogo (JP); Shohei Majima, Hyogo (JP); Takahiro Oshima, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 787 days.

(21) Appl. No.: 17/925,221

(22) PCT Filed: May 13, 2021

(86) PCT No.: PCT/JP2021/018157

§ 371 (c)(1),
(2) Date: Nov. 14, 2022

(87) PCT Pub. No.: WO2021/230308

PCT Pub. Date: Nov. 18, 2021

(65) Prior Publication Data

US 2023/0183205 A1 Jun. 15, 2023

(30) Foreign Application Priority Data

May 15, 2020 (JP) ................................ 2020-086271
Jul. 17, 2020 (JP) ................................ 2020-122771

(51) Int. Cl.
*C07D 401/12* (2006.01)
*A61K 9/20* (2006.01)
*A61K 9/28* (2006.01)

(52) U.S. Cl.
CPC .......... *C07D 401/12* (2013.01); *A61K 9/2013* (2013.01); *A61K 9/2054* (2013.01); *A61K 9/2893* (2013.01); *C07B 2200/13* (2013.01)

(58) Field of Classification Search
CPC C07D 401/12; C07B 2200/13; A61K 9/2013; A61K 9/2054; A61K 9/2893
See application file for complete search history.

(56) References Cited

U.S. PATENT DOCUMENTS

| | | | |
|---|---|---|---|
| 2003/0225050 A1 | 12/2003 | Grawe et al. |
| 2010/0016378 A1 | 1/2010 | Suzuki |
| 2016/0115151 A1 | 4/2016 | Kai |

FOREIGN PATENT DOCUMENTS

| | | |
|---|---|---|
| CA | 2 479 991 | 11/2003 |
| CA | 2 480 004 | 11/2003 |
| EP | 3 009 432 | 4/2016 |
| EP | 3 263 110 | 1/2018 |
| EP | 3 785 716 | 3/2021 |
| EP | 3 862 000 | 8/2021 |
| EP | 4 032 884 | 7/2022 |
| EP | 4 129 294 | 2/2023 |
| JP | 2005-523333 | 8/2005 |
| JP | 2005-524698 | 8/2005 |
| JP | 2009-529982 | 8/2009 |
| JP | 2013-14547 | 1/2013 |
| JP | 2013-121951 | 6/2013 |
| JP | 2015-180684 | 10/2015 |
| JP | 6873534 | 4/2021 |
| WO | 03/091272 | 11/2003 |
| WO | 2003/090714 | 11/2003 |
| WO | 2006/118210 | 11/2006 |
| WO | 2007/106768 | 9/2007 |
| WO | 2014/200078 | 12/2014 |
| WO | 2016/136849 | 9/2016 |
| WO | 2017/175855 | 10/2017 |
| WO | 2019/208540 | 10/2019 |
| WO | 2020/071530 | 4/2020 |

OTHER PUBLICATIONS

International Search Report dated Jun. 15, 2021 in International (PCT) Application No. PCT/JP2021/018157.
International Preliminary Report on Patentability dated Nov. 24, 2022 in International (PCT) Application No. PCT/JP2021/018157.
Extended European Search Report issued Apr. 16, 2024 in counterpart European Patent Application No. 21804194.5.
Zhi Hui Loh et al., "Overview of milling techniques for improving the solubility of poorly water-soluble drugs", Asian Journal of Pharmaceutical Sciences, Feb. 17, 2015, vol. 10, No. 4, pp. 255-274.
P. Bowen, "Particle Size Distribution Measurement from Millimeters to Nanometers and from Rods to Platelets", Journal of Dispersion Science and Technology, 2002, vol. 23, No. 5, pp. 631-662.

*Primary Examiner* — Alicia L Otton
(74) *Attorney, Agent, or Firm* — Wenderoth, Lind & Ponack, L.L.P.

(57) ABSTRACT

By wet-pulverizing a compound represented by Formula (I), a pharmaceutically acceptable salt thereof, or a solvate thereof (hereinafter referred to as a compound represented by Formula (I) or the like), it is possible to provide a crystal of the compound represented by Formula (I) or the like and a pharmaceutical composition containing the same having excellent stability. In addition, by wet-kneading and/or wet-granulating the compound represented by Formula (I) or the like, it is possible to provide a pharmaceutical composition containing the compound represented by Formula (I) or the like having excellent stability.

35 Claims, 15 Drawing Sheets

PHARMACEUTICAL COMPOSITION IN WHICH PRODUCTION OF IMPURITIES IS SUPPRESSED

TECHNICAL FIELD

The present invention relates to a method for producing a crystal of a compound represented by Formula (I):

[Chemical Formula 1]

(I)

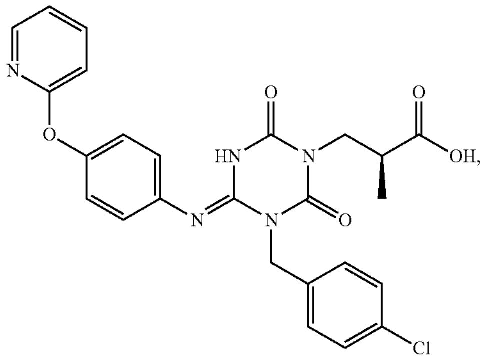

a pharmaceutically acceptable salt thereof, or a solvate thereof (hereinafter referred to as a compound represented by Formula (I) or the like). More specifically, the present invention relates to a method for producing a crystal of a compound represented by Formula (I) or the like, characterized by wet-pulverizing the compound represented by Formula (I) or the like.

The present invention also relates to a method for producing a pharmaceutical composition containing a compound represented by Formula (I) or the like. More specifically, the present invention relates to a method for producing a pharmaceutical composition containing a compound represented by Formula (I) or the like, the method including a step of wet-pulverizing the compound represented by Formula (I) or the like, or a step of wet-kneading and/or wet-granulating the compound represented by Formula (I) or the like. The present invention also relates to a pharmaceutical composition containing a compound represented by Formula (I) or the like.

BACKGROUND ART

A compound represented by Formula (I) or the like is described in Patent Documents 1 and 9 as a compound having a $P2X_3$ and/or $P2X_{2/3}$ receptor antagonistic action. However, Patent Documents 1 and 9 neither disclose nor suggest a specific pharmaceutical composition containing the compound represented by Formula (I) or the like.

Crystallization and pulverization methods for active pharmaceutical ingredients have been studied.

Patent Documents 10 and 11 describe that fine pulverization with a jet mill causes enlargement of a surface area and thermodynamic activation of a surface due to partial amorphization and/or large destruction or perturbation of a lattice structure as a conventional art. Patent Document 10 describes a production method including a step of subjecting a supersaturated solution containing a 11ß-benzaldoxime-estra-4,9-diene derivative to wet pulverization using a wet pulverizer while crystallizing the supersaturated solution. Patent Document 11 describes an example of using a supersaturated solution containing a steroid. It is described that these production methods can produce crystals that do not have disadvantages of a conventional art and meet requirements of low-dose formulations.

As a method for producing a crystal having a particle size within a predetermined particle size range by wet-pulverizing a supersaturated solution, for example, Patent Document 12 describes a method for producing crystals of a Cox-II inhibitor, a BK1 antagonist, a bisphosphonate, a DP-1V inhibitor, and a lipid-lowering compound.

However, these documents neither disclose nor suggest a crystal of the compound represented by Formula (I) or the like and a method for producing the same.

In addition, methods for stabilizing solid formulations have been widely studied. For example, Patent Document 2 describes a method for stabilizing wet-treated amlodipine, characterized by wet-kneading or wet-granulating amlodipine using water or a water-containing solvent in which either methylcellulose or hydroxypropyl methylcellulose is dissolved or suspended. In addition, additives that stabilize solid formulations have been widely studied. For example, Patent Documents 3 to 8 report that storage stability is improved by adding triethyl citrate, medium-chain triglyceride miglyol 812, or triacetin to a compound having candesartan cilexetil, baloxavir marboxil, a cyano group, and an amino group.

PRIOR ART REFERENCES

Patent Document

[Patent Document 1] International Publication WO 2014/200078 A
[Patent Document 2] International Publication WO 2006/118210 A
[Patent Document 3] JP 2013-14547 A
[Patent Document 4] JP 2013-121951 A
[Patent Document 5] JP 2015-180684 A
[Patent Document 6] International Publication WO 2016/136849 A
[Patent Document 7] International Publication WO 2017/175855 A
[Patent Document 8] International Publication WO 2019/208540 A
[Patent Document 9] International Publication WO 2020/071530 A
[Patent Document 10] JP 2005-523333 A
[Patent Document 11] JP 2005-524698 A
[Patent Document 12] JP 2009-529982 A

SUMMARY OF THE INVENTION

Problems to be Solved by the Invention

In order to examine stability of the compound represented by Formula (I) or the like in production of a pharmaceutical composition containing the compound represented by Formula (I) or the like, the present inventors conducted a stability testing using a raw material obtained by dry-pulverizing the compound represented by Formula (I) or the like, and found that an amount of a compound represented by Formula (III):

[Chemical Formula 2]

(III)

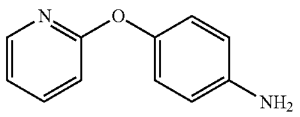

(hereinafter referred to as a compound represented by Formula (III)) increases. That is, an object of the present invention is to provide a pharmaceutical composition having excellent stability containing the compound represented by Formula (I) or the like.

Means for Solving the Problem

The present inventors have extensively conducted studies for achieving the above-mentioned object, and resultantly found that by wet-pulverizing a compound represented by Formula (I) or the like to obtain a crystal of the compound represented by Formula (I) or the like, and by producing a pharmaceutical composition containing the crystal, it is possible to suppress production of a compound represented by Formula (III) in a stability testing, and it is possible to stabilize the pharmaceutical composition containing the compound represented by Formula (I) or the like.

That is, the present inventors have found that by wet-pulverizing the compound represented by Formula (I) or the like, it is possible to produce a crystal of the compound represented by Formula (I) or the like that does not contain the compound represented by Formula (III) or contains the compound represented by Formula (III) and has a content ratio of the compound represented by Formula (III) to an amount of the compound represented by Formula (I) of 0.0001 to 30 ppm, preferably 0.0001 to 10 ppm.

Further, the present inventors have found that even when a stability testing is performed, these crystals do not contain the compound represented by Formula (III) or contain the compound represented by Formula (III) and has a content ratio of the compound represented by Formula (III) to an amount of the compound represented by Formula (I) or the like of 0.0001 to 30 ppm, preferably 0.0001 to 10 ppm.

Furthermore, the present inventors have also found that in a dihydrate crystal of the compound represented by Formula (I), the compound represented by Formula (III) is not contained or is below a detection limit.

In addition, the present inventors have found that by wet-kneading and/or wet-granulating the compound represented by Formula (I) or the like to produce a pharmaceutical composition containing the compound represented by Formula (I) or the like, it is possible to suppress production of the compound represented by Formula (II) in a stability testing, and it is possible to stabilize the pharmaceutical composition containing the compound represented by Formula (I) or the like.

Furthermore, the present inventors have also found that by using a polyhydric alcohol ester in the step of wet kneading and/or wet granulation, it is possible to further stabilize the pharmaceutical composition containing the compound represented by Formula (I) or the like.

That is, the present invention includes the following inventions.

(1) A method for producing a pharmaceutical composition containing a compound represented by Formula (I) or the like, the method including: a step of wet-pulverizing the compound represented by Formula (I) or the like; and/or a step of wet-kneading and/or wet-granulating the compound represented by Formula (I) or the like.

(2) The method for producing the pharmaceutical composition according to the above (1), the method including a step of wet-kneading and/or wet-granulating the compound represented by Formula (I) or the like.

(3) The method for producing the pharmaceutical composition according to the above (2), wherein the pharmaceutical composition does not contain a compound represented by Formula (III) or contains the compound represented by Formula (11) and has a content ratio of the compound represented by Formula (III) to an amount of the compound represented by Formula (I) or the like of 0.0001 to 10 ppm. The method for producing the pharmaceutical composition according to the above (2) or (3), characterized by using a hydroxycarboxylic acid ester, a polyhydric alcohol ester, and/or a polyether in the step of wet kneading and/or wet granulation, the method for producing the pharmaceutical composition according to the above (2) or (8), characterized by using one or more selected from the group consisting of triethyl citrate, miglyol, triacetin, macrogol 6000, polysorbate 20, polysorbate 60, polysorbate 80, sesame oil, corn oil, olive oil, and soybean oil, the method for producing the pharmaceutical composition according to the above (2) or (3), characterized by using one or more selected from the group consisting of triethyl citrate, miglyol, and triacetin, the method for producing the pharmaceutical composition according to the above (2) or (8), characterized by using triethyl citrate, and the method for producing the pharmaceutical composition according to the above (2) or (3), characterized by using one or more selected from the group consisting of lactose, hydroxypropylcellulose, and low-substituted hydroxypropylcellulose in the step of wet kneading and/or wet granulation, are also included in the present invention.

(4) The method according to the above (3), wherein when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I) or the like is 0.0001 to 10 ppm, (5) The method for producing the pharmaceutical composition according to any one of the above (2) to (4), wherein the compound represented by Formula (I), the pharmaceutically acceptable salt thereof, or the solvate thereof used for the wet kneading and/or the wet granulation is obtained by dry pulverization.

(6) The method for producing the pharmaceutical composition according to the above (1), the method including a step of wet-pulverizing the compound represented by Formula (I) or the like.

(7) A pharmaceutical composition, containing a compound represented by Formula (I) or the like, the pharmaceutical composition being obtained by the method for producing the pharmaceutical composition according to any one of the above (1) to (6).

A pharmaceutical composition containing the compound represented by Formula (I) or the like that has been wet-kneaded and/or wet-granulated is also included in the present invention.

(8) The pharmaceutical composition according to the above (7), which does not contain a compound represented by Formula (III) or contains the compound represented by Formula (III) and has a content ratio of the compound represented by Formula (III) to an amount of the compound represented by Formula (I) or the like of 0.0001 to 10 ppm.

(9) The pharmaceutical composition according to the above (8), wherein when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I) or the like is 0.0001 to 10 ppm.

(10) A pharmaceutical composition, containing a compound represented by Formula (I) or the like, the pharmaceutical composition being a tablet or a granule and containing a hydroxycarboxylic acid ester, a polyhydric alcohol ester, and/or a polyether in a core tablet or an uncoated granule.

(11) The pharmaceutical composition according to the above (10), wherein one or more selected from the group consisting of triethyl citrate, migiyol, triacetin, macrogol 6000, polysorbate 20, polysorbate 60, polysorbate 80, sesame oil, corn oil, olive oil, and soybean oil are contained in the core tablet or the uncoated granule.

(12) The pharmaceutical composition according to the above (11), wherein one or more selected from the group consisting of triethyl citrate, miglyol, and triacetin are contained in the core tablet or the uncoated granule.

(13) The pharmaceutical composition according to the above (12), wherein triethyl citrate is contained in the core tablet or the uncoated granule.

(14) The pharmaceutical composition according to any one of the above (10) to (13), wherein an amount of the hydroxycarboxylic acid ester, the polyhydric alcohol ester, and/or the polyether is 0.01 to 10% by weight based on a total amount of the tablet or the granule.

(15) The pharmaceutical composition according to any one of the above (10) to (13), wherein the amount of the hydroxycarboxylic acid ester, the polyhydric alcohol ester, and/or the polyether is 0.0001 to 0.5 parts by weight based on 1 part by weight of the compound represented by Formula (I) or the like.

The pharmaceutical composition according to any one of the above (10) to (15), which does not contain a compound represented by Formula (III) or contains the compound represented by Formula (III) and has a content ratio of the compound represented by Formula (III) to an amount of the compound represented by Formula (I), a pharmaceutically acceptable salt thereof, or a solvate thereof of 0.0001 to 10 ppm, the pharmaceutical composition according to any one of the above (10) to (15), wherein when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I), the pharmaceutically acceptable salt thereof, or the solvate thereof is 0.0001 to 10 ppm, the pharmaceutical composition according to any one of the above (10) to (15), containing 10 to 450 mg of the compound represented by Formula (I) or the like, and the pharmaceutical composition according to any one of the above (10) to (15), containing one or more additives selected from the group consisting of an excipient, a binder, and a disintegrant, are also included in the present invention.

(16) The pharmaceutical composition according to any one of the above (10) to (15), containing one or more selected from the group consisting of lactose, low-substituted hydroxypropylcellulose, and hydroxypropylcellulose.

The pharmaceutical composition according to any one of the above (10) to (16), which is a core tablet, and the pharmaceutical composition according to any one of the above (10) to (16), which is a film-coated tablet, are also included in the present invention.

(17) A method for producing a crystal of a compound represented by Formula (I) or the like, characterized by wet-pulverizing the compound represented by Formula (I) or the like.

(18) The method according to the above (17), wherein the crystal obtained does not contain a compound represented by Formula (III) or contains the compound represented by Formula (III) and has a content ratio of the compound represented by Formula (III) to an amount of the compound represented by Formula (I) or the like of 0.0001 to 10 ppm.

(19) The method according to the above (18), wherein when the crystal obtained is subjected to a stability testing under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I) or the like is 0.0001 to 10 ppm.

(20) The method according to any one of the above (17) to (19), wherein a 90% particle size distribution of the crystal obtained is 100 μm or less.

(21) The method according to any one of the above (17) to (20), wherein the crystal obtained is an anhydrate crystal of the compound represented by Formula (I). The method according to any one of the above (17) to (20), wherein the crystal obtained is a dihydrate crystal of the compound represented by Formula (I), the method according to any one of the above (17) to (20), characterized by wet-pulverizing a crystal of the compound represented by Formula (I) or the like, the method according to any one of the above (17) to (20), characterized by wet-pulverizing an anhydrate crystal of the compound represented by Formula (I) or the like, and the method according to any one of the above (17) to (20), characterized by wet-pulverizing a dihydrate crystal of the compound represented by Formula (I) or the like, are also included in the present invention.

(22) The method according to any one of the above (17) to (21), characterized by wet-pulverizing an anhydrate crystal and/or an amorphous substance of the compound represented by Formula (I).

(23) The method according to any one of the above (17) to (21), characterized by wet-pulverizing a supersaturated solution.

The method according to the above (23), including: a step of producing an anhydrate crystal of the compound represented by Formula (I) from the supersaturated solution; and a step of controlling a 90% particle size distribution of the crystal obtained in the step to be 100 μm or less, is also included in the present invention.

(24) The method according to the above (23), including: a step of forming a nucleus of a crystal from the supersaturated solution; a step of crystal-growing the nucleus obtained in the step; a step of controlling nucleation and crystal growth; and a step of refining the crystal.

(25) The method according to the above (24), including: a step of producing a dihydrate crystal of the compound represented by Formula (I) from the supersaturated solution: a step of producing an anhydrate crystal of the compound represented by Formula (I) from the crystal obtained in the step; and a step of controlling a 90% particle size distribution of the crystal obtained in the step to be 100 μm or less.

(26) The method according to the above (25), wherein the step of producing a dihydrate crystal of the compound represented by Formula (I) from the supersaturated solution is performed at 25±5° C.

(27) The method according to the above (25) or (26), wherein the step of producing an anhydrate crystal of the compound represented by Form ula (I) from the dihydrate crystal of the compound represented by Formula (I) includes a step of heating and cooling.

(28) The method according to any one of the above (17) to (27), wherein a solvent in a step of the wet-pulverizing contains one or more solvents selected from the group consisting of water, methanol, and 2-propanol.

The method according to any one of the above (17) to (27), wherein a solvent in a step of the wet-pulverizing contains water, an organic solvent, or a mixed solvent thereof, the method according to any one of the above (17) to (28), wherein a step of the wet pulverizing is performed by one or more selected from the group consisting of a rotor stator, a pressure type homogenizer, a ball mill, a medium mill, and ultrasonic crushing, the method according to any one of the above (17) to (28), wherein a step of the wet-pulverizing is one or more selected from the group consisting of a batch type method, a semi-continuous type method, and a continuous type method, the method according to any one of the above (17) to (28), wherein a step of the wet-pulverizing is a step using a recirculation loop, and the method according to any one of the above (17) to (28), wherein a step of the wet-pulverizing is performed in one pot, are also included in the present invention.

(29) A crystal of a compound represented by Formula (I) or the like, the crystal being obtained by the method according to any one of the above (17) to (28). An anhydrate crystal of the compound represented by Formula (I) obtained by the method according to the above (21), a crystal of the compound represented by Formula (I) that has been wet-pulverized, and an anhydrate crystal of the compound represented by Formula (I) that has been wet-pulverized are also included in the present invention.

(30) The crystal according to the above (29), which does not contain a compound represented by Formula (III) or contains the compound represented by Formula (III) and has a content ratio of the compound represented by Formula (III) to an amount of the compound represented by Formula (I) or the like of 0,0001 to 10 ppm.

(31) The crystal according to the above (30), wherein when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I) or the like is 0.0001 to 10 ppm.

The crystal according to any one of the above (29) to (31), wherein a 90% particle size distribution is 100 μm or less, is also included in the present invention.

(32) The crystal according to any one of the above (29) to (31), which is an anhydrate crystal of the compound represented by Formula (I).

(33) The crystal according to the above (32), which exhibits characteristic X-ray powder diffraction peaks at diffraction angles (2θ) of 15.8±0.2°, 19.4±0.2°, 21.7±0.2°, 23.9±0.2°, and 25.4±0.2° or diffraction angles (2θ) of 7.9±0.2°, 9.3±0.2°, 12.9±0.2°, 15.8±0.2°, and 19.4±0.2°.

The crystal according to the above (32), which exhibits characteristic X-ray powder diffraction peaks at diffraction angles (2θ) of 15.8±0.2°, 19.4±0.2°, 21.7±0.2°, 23.9±0.2°, and 25.4±0.2°, the crystal according to the above (32), which exhibits characteristic X-ray powder diffraction peaks at diffraction angles (2θ) of 7.9±0.2°, 9.3±0.2°, 12.9±0.2°, 15.8±0.2°, and 19.4±0.2°, the crystal according to the above (32), which exhibits characteristic X-ray powder diffraction peaks at diffraction angles (2θ) of 12.6±0.2°, 12.9±0.2°, 15.8±0.2°, 19.4±0.2°, 21.7±0.2°, 23.9±0.2°, 25.4±0.2°, 26.6±0.2°, 27.8±0.2°, and 32.8±0.2° or diffraction angles (2θ) of 7.9±0.2°, 9.3±0.2°, 12.9±0.2°, 15.8±0.2°, 17.2±0.2°, 19.4±0.2°, 21.7±0.2°, 23.9±0.2°, 25.4±0.2°, and 27.8±0.2°, the crystal according to the above (32), which exhibits characteristic X-ray powder diffraction peaks at diffraction angles (2θ) of 12.6±0.2°, 12.9±0.2°, 15.8±0.2°, 19.4±0.2°, 21.7±0.2°, 23.9±0.2°, 25.4±0.2°, 26.6±0.2°, 27.8±0.2°, and 32.8±0.2°, the crystal according to the above (32), which exhibits characteristic X-ray powder diffraction peaks at diffraction angles (2θ) of 7.9±0.2°, 9.3±0.2°, 12.9±0.2°, 15.8±0.2°, 17.2±0.2°, 19.4±0.2°, 21.7±0.2°, 23.9±0.2°, 25.4±0.2°, and 27.8±0.2°, the crystal according to the above (32), characterized by an X-ray powder diffraction pattern substantially identical to that shown in FIG. 1, the crystal according to the above (32), characterized by a Raman spectrum substantially identical to that shown in FIG. 2, and the crystal according to the above (32), having absorption peaks at 829 $cm^{-1}$±2 $cm^{-1}$, 989 $cm^{-1}$±2 $cm^{-1}$, 1013 $cm^{-1}$±2 $cm^{-1}$, 1128 $cm^{-1}$±2 $cm^{-1}$, and 1370 $cm^{-1}$+2 $cm^{-1}$ in a Raman spectrum, are also included in the present invention.

(34) A method for analyzing a related substance in a sample, the method including: a) a step of using a crystal of a compound represented by Formula (I) or the like, or a pharmaceutical composition containing the compound represented by Formula (I) or the like as the sample, and performing chromatographic analysis on the sample; and b) a step of obtaining a content or a content ratio of a compound represented by Formula (III) in the chromatographic analysis obtained in the above step.

(35) A method for analyzing a content or a content ratio of a compound represented by Formula (III) in a crystal of a compound represented by Formula (I) or the like, or in a pharmaceutical composition containing the compound represented by Formula (I) or the like, wherein the compound represented by Formula (III) is used as a standard sample.

A dihydrate crystal of the compound represented by Formula (I), a dihydrate crystal of the compound represented by Formula (I), which exhibits characteristic X-ray powder diffraction peaks at diffraction angles (2θ) of 5.7±0.2°, 7.7±0.2°, 11.8±0.2°, 15.2±0.2°, and 17.7±0.2°, a dihydrate crystal of the compound represented by Formula (I), which exhibits characteristic X-ray powder diffraction peaks at diffraction angles (2θ) of 5.7±0.2°, 7.7±0.2°, 11.8±0.2°, 15.2±0.2°, 17.7±0.2°, 20.6±0.2°, 20.8±0.2°, 20.5±0.20, 27.1±0.2°, and 29.1±0.2°, and a dihydrate crystal of the compound represented by Formula (I), characterized by an X-ray powder diffraction pattern substantially identical to that shown in FIG. 3, are also included in the present invention.

Effect of the Invention

By wet-pulverizing the compound represented by Formula (I) or the like, it was possible to produce a crystal having excellent stability. In addition, by using the crystal, it was possible to improve stability of the pharmaceutical composition containing the compound represented by Formula (I) or the like. In addition, by wet-kneading and/or wet-granulating the compound represented by Formula (I) or the like, it was possible to improve the stability of the pharmaceutical composition containing the compound represented by Formula (I) or the like.

BRIEF DESCRIPTION OF TILE DRAWINGS

Figure 8:
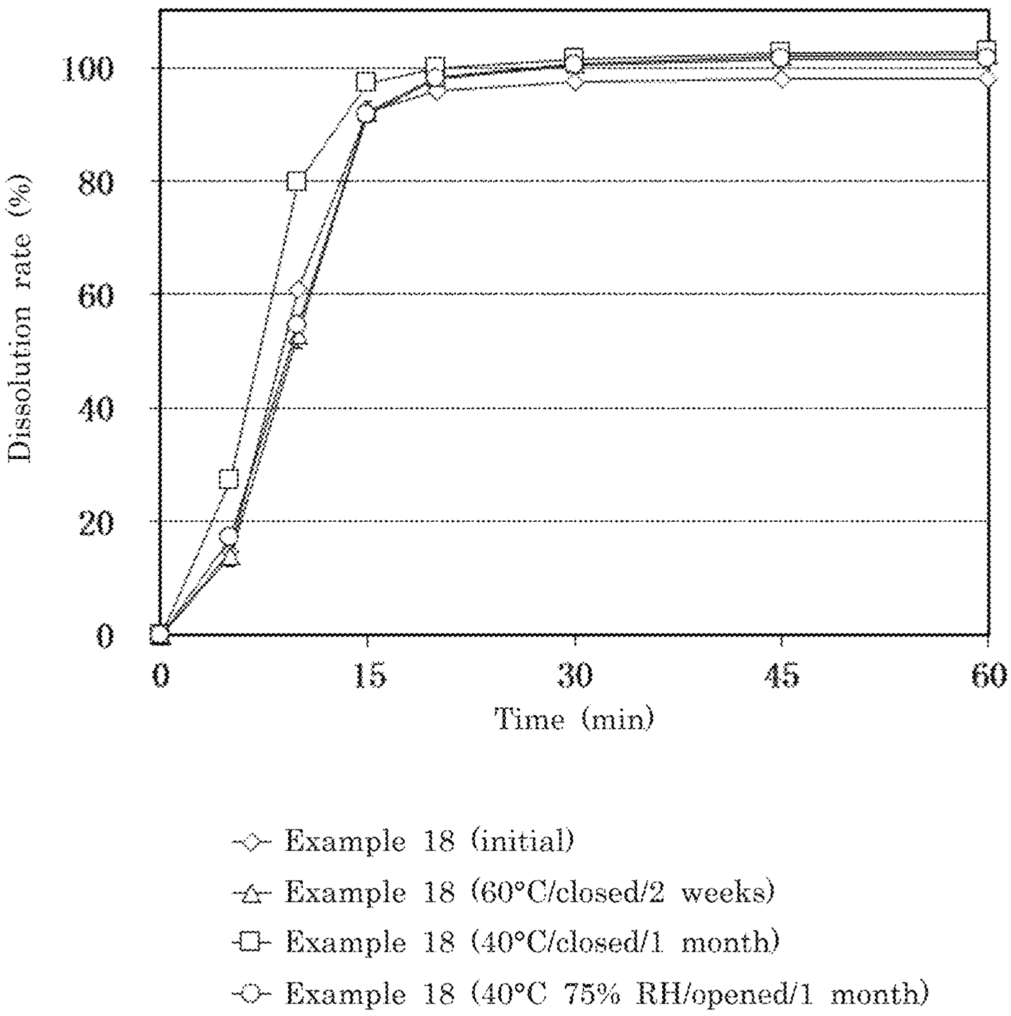

FIG. 8 shows dissolution profile of the 10 mg tablet containing triethyl citrate after storage under a condition of 60° C. closed for 2 weeks, under a condition of 40° C. closed for 1 month, and a condition of 40° C./75% RE opened for 1 month. The horizontal axis represents time (min), and the vertical axis represents a dissolution rate (%).

Figure 9:
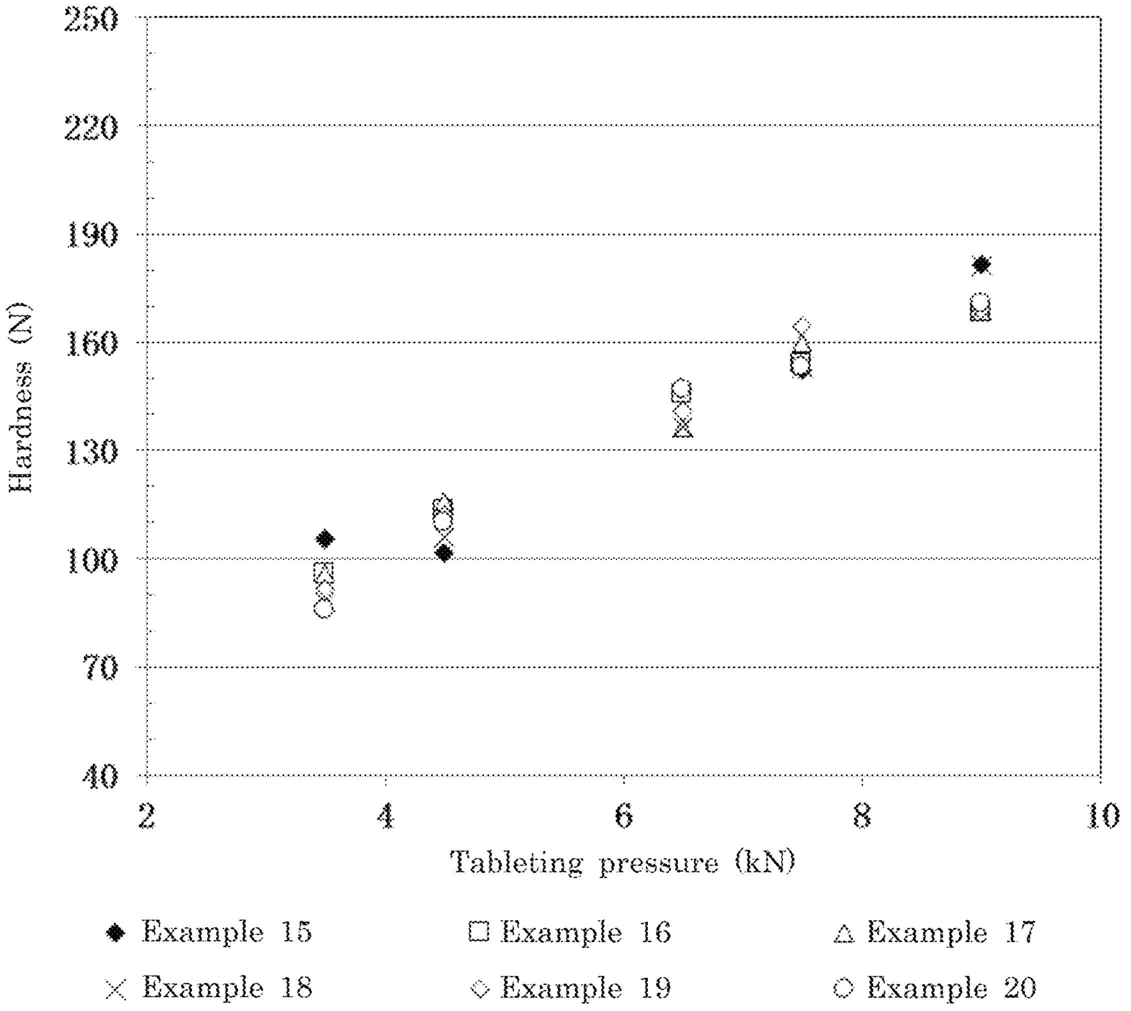

FIG. 9 shows physical properties of the 10 mg tablet containing triethyl citrate. The horizontal axis represents a tableting pressure (kN), and the vertical axis represents a hardness (N).

Figure 10:
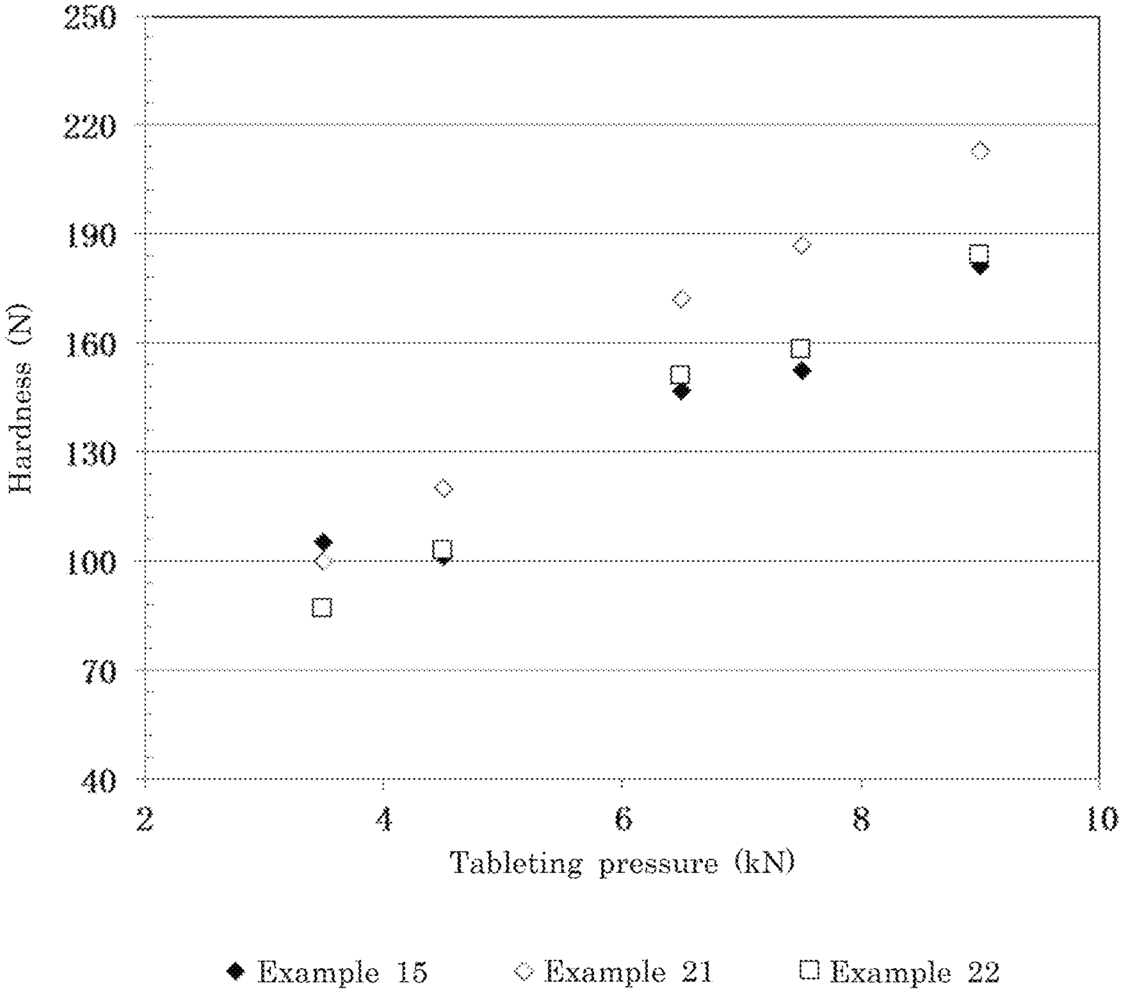

FIG. 10 shows physical properties of a 10 mg tablet containing miglyol 812. The horizontal axis represents a tableting pressure (kN), and the vertical axis represents a hardness (N).

Figure 11:
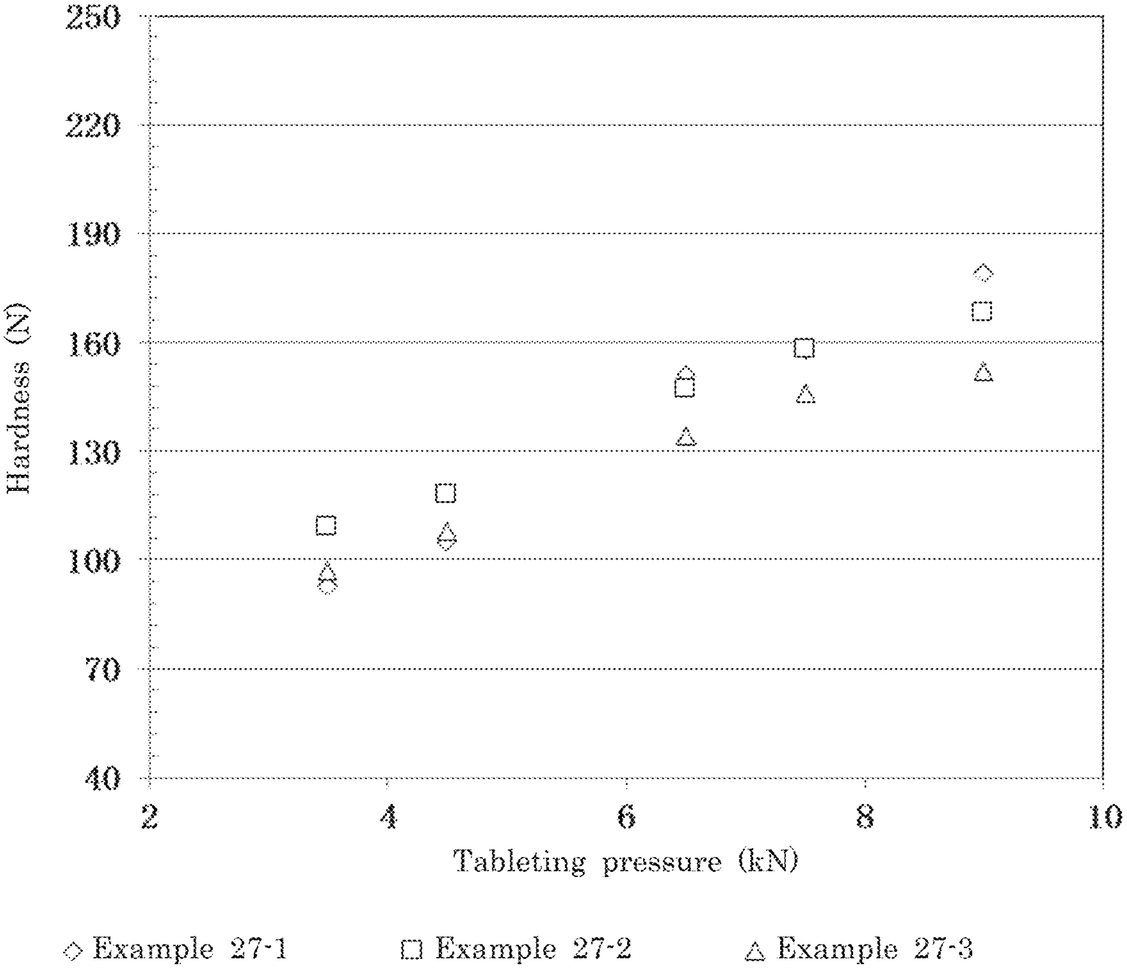

FIG. 11 shows physical properties of a 50 mg tablet containing triethyl citrate. The horizontal axis represents a tableting pressure (kN), and the vertical axis represents a hardness (N).

Figure 12:
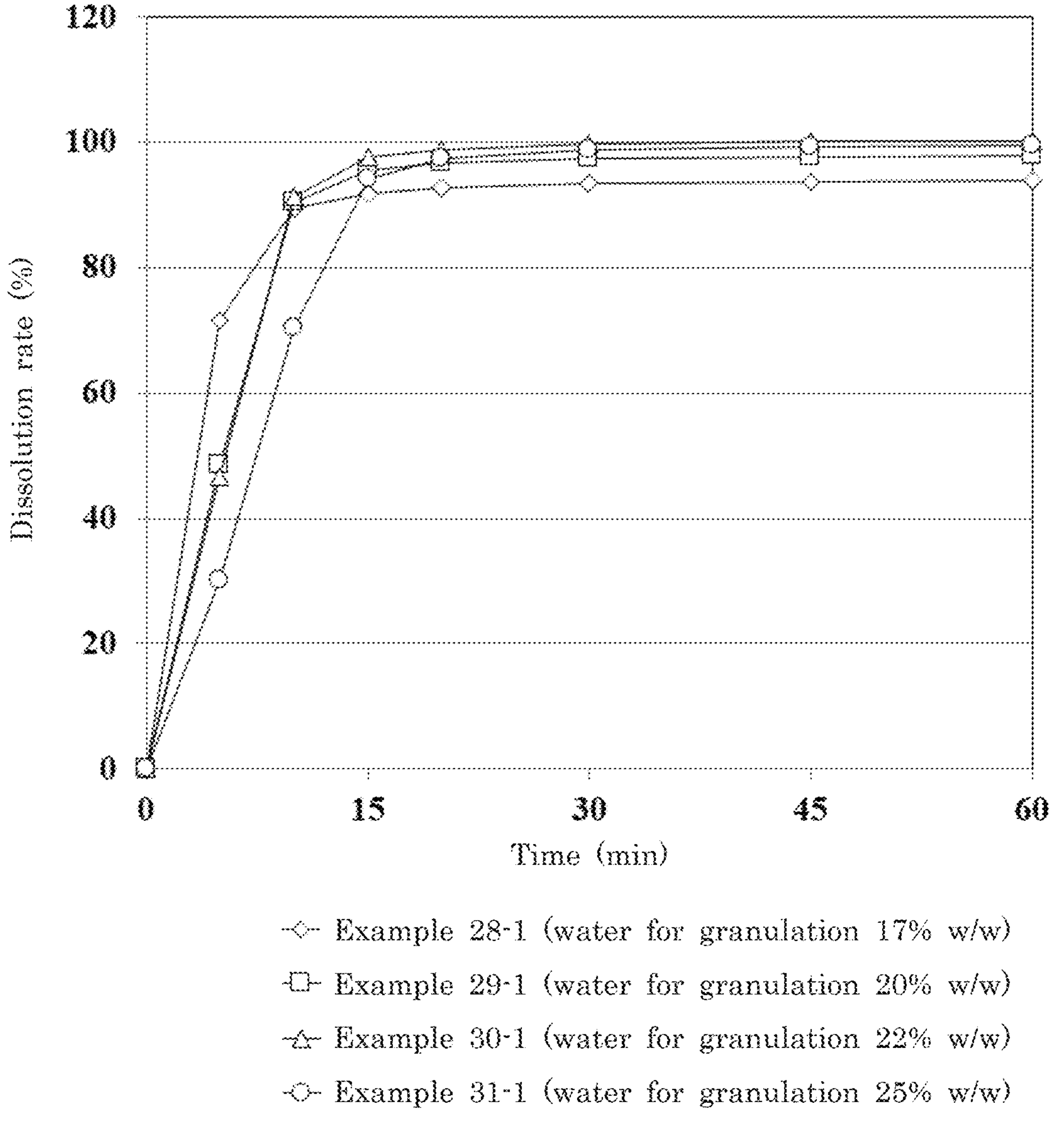

FIG. 12 shows dissolution profile of a 10 mg tablet (core tablet) produced by changing water for granulation at the time of granulation, producing a granule with a stirring granulator, and tableting the granule. The horizontal axis represents time (min), and the vertical axis represents a dissolution rate (%).

Figure 13:
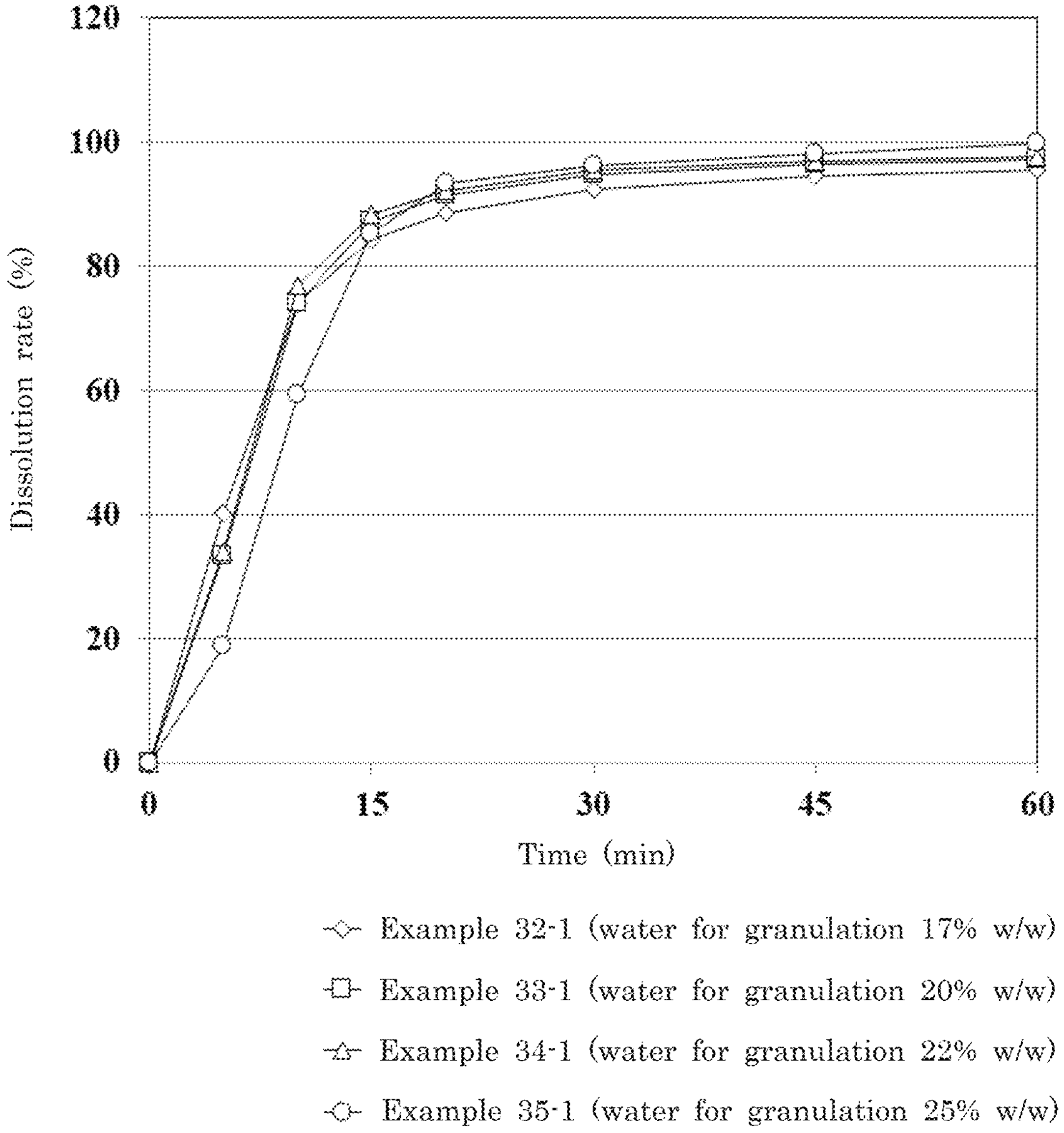

FIG. 13 shows dissolution profile of a 50 mg tablet (core tablet) produced by changing water for granulation at the time of granulation, producing a granule with a stirring granulator, and tableting the granule. The horizontal axis represents time (min), and the vertical axis represents a dissolution rate (%).

Figure 14:
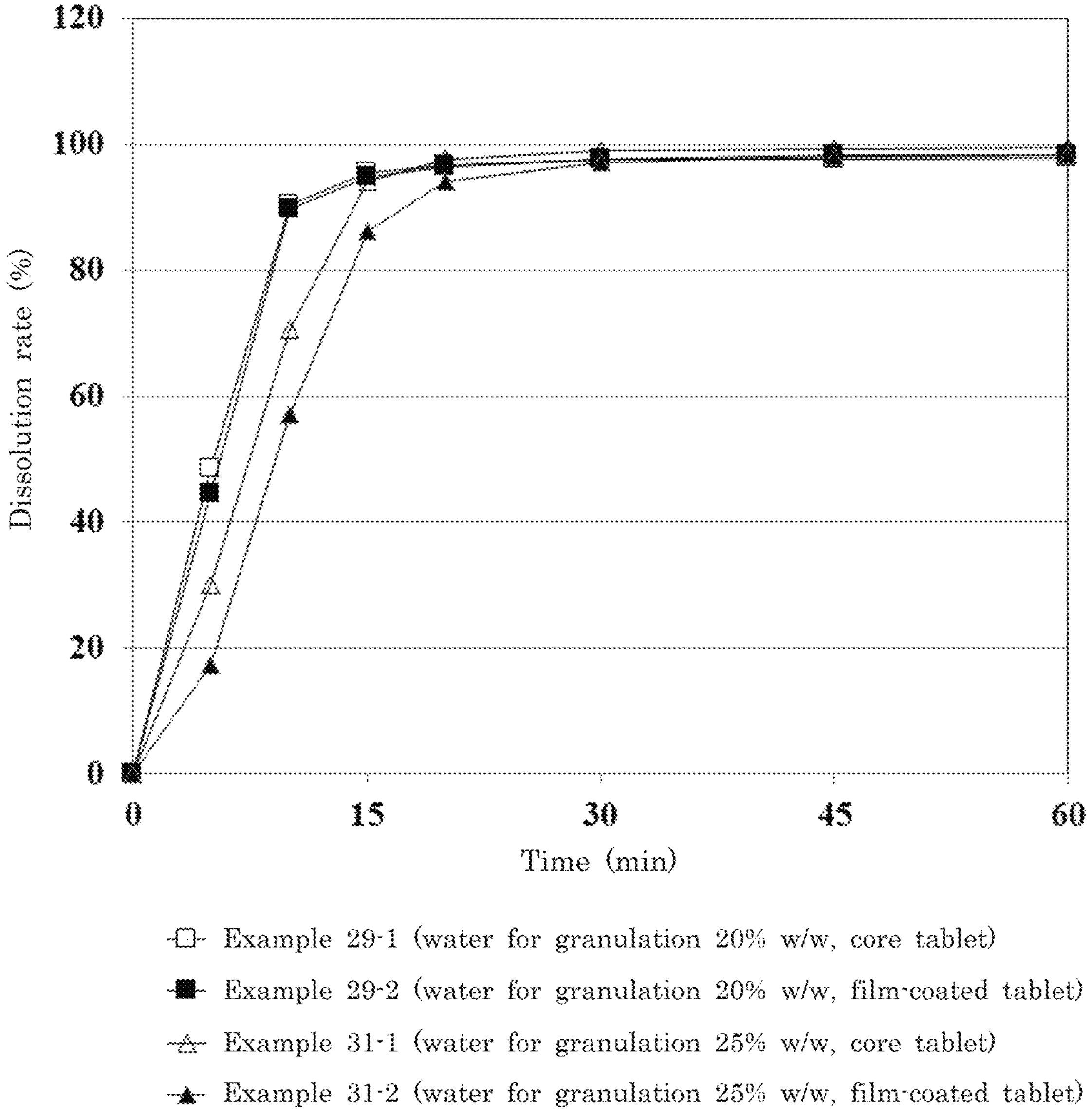

FIG. 14 shows dissolution profile of 10 mg tablets (core tablet and film-coated tablet) produced by producing granules with a stirring granulator and tableting the granules. The horizontal axis represents time (min), and the vertical axis represents a dissolution rate (%).

Figure 15:
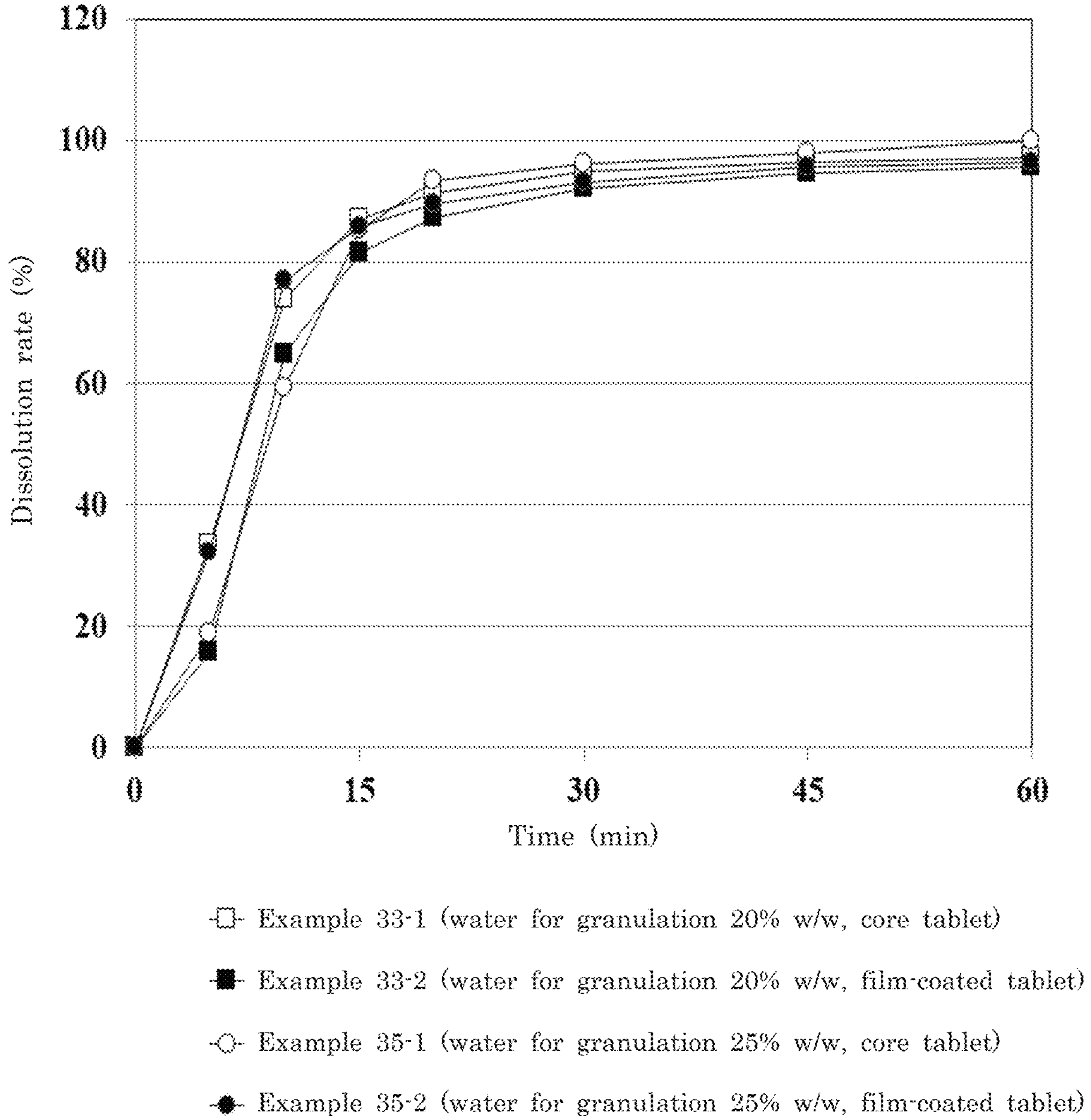

FIG. 15 shows dissolution profile of 50 mg tablets (core tablet and film-coated tablet) produced by producing granules with a stirring granulator and tableting the granules. The horizontal axis represents time (min), and the vertical axis represents a dissolution rate (%).

MODE FOR CARRYING OUT THE INVENTION

Hereinafter, the present invention will be described in detail. Unless otherwise specified, each term is used in the same meaning when used alone or in combination with another term. Chemical structural formulas represented by Formula (I), Formula (II), and Formula (III) are also commonly used in the respective formulas.

The term “consisting of” means having only the components. The term “including” or “containing” means being not limited to the components, but not excluding elements that are not described.

It is to be understood that throughout the specification, the singular forms of expression also include the concept of the plural forms thereof, unless otherwise stated. Thus, it is to be understood that the singular article (for example, in English, “a”, “an”, “the”, and the like) also includes the plural concept thereof unless otherwise stated.

It is also to be understood that the terms used in the present specification are used in the sense commonly used in the art, unless otherwise stated. Thus, unless defined otherwise, all technical and scientific terms used in the present specification have the same meanings as those commonly understood by those skill in the art to which the present invention belongs. In case of conflict, the present specification (including definitions) will control.

The present invention is a method for producing a crystal of a compound represented by Formula (I):

[Chemical Formula 3]

(I)

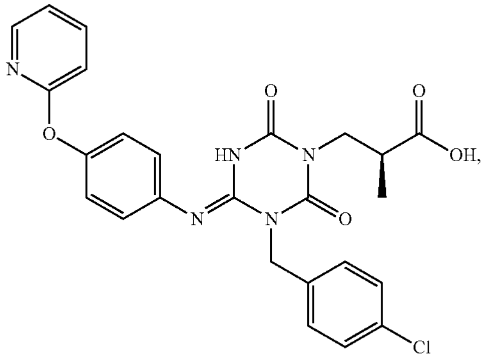

or the like, characterized by wet-pulverizing the compound represented by Formula (I) or the like.

The compound represented by Formula (I) or the like means a compound represented by Formula (I):

[Chemical Formula 4]

(I)

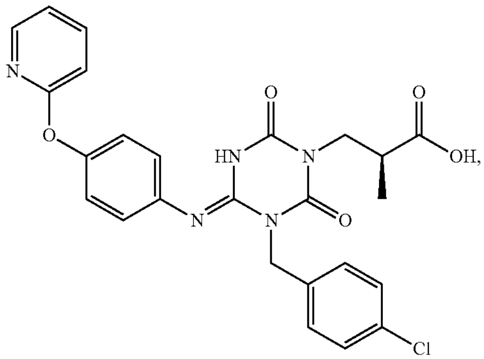

a pharmaceutically acceptable salt thereof, or a solvate thereof.

The compound represented by Formula (I) includes not only the compound represented by Formula (I) but also a tautomer thereof or a mixture thereof.

The compound represented by Formula (I) is described in Patent Documents 1 and 9 as a compound having a $P2X_3$ and/or $P2X_{2/3}$ receptor antagonistic action.

The tautomer of the compound represented by Formula (I) is a compound represented by Formula (II):

[Chemical Formula 5]

(II)

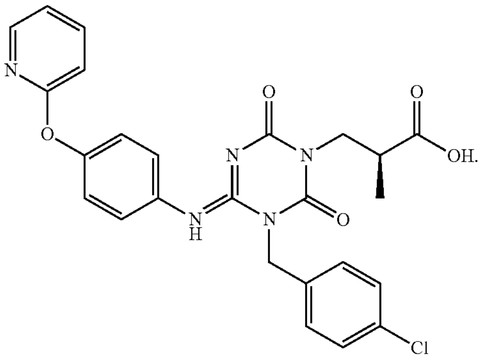

This compound has a $P2X_3$ and/or $P2X_{2/3}$ receptor antagonistic action, like the compound represented by Formula (I).

The compound represented by Formula (I) may also include a mixture of the compound represented by Formula (I) and the compound represented by Formula (II), and they may be mixed at an arbitrary ratio.

Further, one or more hydrogen, carbon, or other atoms of the compound represented by Formula (I), a tautomer thereof, or a mixture thereof may be substituted with isotope(s) of hydrogen, carbon, or other atoms. For example, the compound represented by Formula (I), a tautomner thereof, or a mixture thereof may be labeled with an isotope (e.g., $^{2}H$, $^{1}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$).

The “pharmaceutically acceptable salt” used in the present specification may be composed of, for example, the “compound represented by Formula (I), a tautomer thereof, or a mixture thereof” and a counter molecule or a counter ion and may include any number of counter molecules or counter ions.

In one aspect of the present invention, the compound is in the form of a base addition salt. Examples of the base addition salt include salts made from pharmaceutically acceptable non-toxic bases including inorganic and organic bases. Examples of the salt derived from inorganic bases include, but are not limited to, salts of aluminum, calcium, lithium, potassium, magnesium, sodium, zinc, and other metal salts. Examples of the salt derived from pharmaceutically acceptable non-toxic bases include salts of primary, secondary or tertiary amines, and substituted amines including naturally occurring substituted amines, cyclic amines and basic ion exchange resins, such as, arginine, betaine, benzathine, caffeine, choline, chloroprocaine, cycloprocaine, N'N'-dibenzylethylenediamine, diethanolamine, diethylamine, 2-diethyl-aminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, meglumine, morpholine, piperazine, piperidine, polyamine resins, procaine, purines, tertiary butylamine (2-methylpropane-2-amine), theobromine, triethylamine, trimethylamine, tripropylamine, and tromethamine; as well as nontoxic ammonium and quaternary ammonium, and salts of cations including, but not limited to, ammonium, tetramethylammonium, and tetraethylammonium.

In one aspect of the present invention, the compound is in the form of an acid addition salt. Examples of the acid addition salt include salts made from pharmaceutically acceptable non-toxic acids including inorganic and organic acids. Examples of the inorganic acid include, but are not limited to, hydrofluoric acid, hydrochloric acid, hydrobromic acid, orthophosphoric acid, hydroiodic acid, nitric acid, phosphoric acid, boric acid, and sulfuric acid. Examples of the organic acid include, but are not limited to, methanesulfonic acid, ethanesulfonic acid, p-toluenesulfonic acid, benzenesulfonic acid, trifluoromethylbenzenesulfonic acid, chlorobenzenesulfonic acid, methoxybenzenesulfonic acid, acetic acid, propionic acid, lactic acid, citric acid, fumaric acid, malonic acid, malic acid, succinic acid, salicylic acid, maleic acid, glycerophosphoric acid, tartaric acid, benzoic acid, glutamic acid, aspartic acid, 2-naphthalenesulfonic acid, hexanoic acid, or acetylsalicylic acid. The acid addition salt may be a mixed acid salt of two or more combinations selected from these acids.

In one aspect of the present invention, a free (or amphoteric ionic or zwitterionic) form may be converted to a pharmaceutically acceptable salt or a solvate of a salt by reacting the free form with a desired acid or base.

The term "pharmaceutically acceptable solvate" used in the present specification refers to, for example, one that is arranged with an arbitrary number of solvent molecules with respect to the compound represented by Formula (I) or a pharmaceutically acceptable salt thereof.

Examples of the solvent molecule include acetonitrile, chlorobenzene, chloroform, cyclohexane, 1,2-dichloroethene, dichloromethane, 1,2-dimethoxyethane, N,N-dimethylacetamide, N,N-dimethylfomamide, 1,4-dioxane, 2-ethoxyethanol, ethylene glycol, formamide, hexane, methanol, 2-methoxyethanol, methylbutyl ketone, methylcyclohexane, N-methylpyrrolidone, nitromethane, pyridine, sulfolane, tetralin, toluene, 1,1,2-trichloroethene, xylene, acetic acid, anisole, 1-butanol, 2-butanol, t-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methy-1-butanol, methyl ethyl ketone, methyl isobutyl ketone, 2-methyl-1-propanol, pentane, 1-pentanol, 1-propanol, 2-propanol, propyl acetate, tetrahydrofuran, water (i.e., hydrate), ethanol, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid, and trifluoroacetic acid.

Preferred examples include acetic acid, anisole, 1-butanol, 2-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1 butanol, methyl ethyl ketone, methyl isobutyl ketone, 2-methyl-1-propanol, pentane, 1-pentanol, 1-propanol, 2-propanol, propyl acetate, tetrahydrofuran, water (i.e., hydrate), ethanol, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid and trifluoroacetic acid.

More preferred examples thereof include water (i.e., hydrate), ethanol, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid, and trifluoroacetic acid.

When the compound represented by Formula (I) or a pharmaceutically acceptable salt thereof is left to stand in the atmosphere, moisture is absorbed, and adsorbed water may adhere thereto, or a hydrate may be formed.

The pharmaceutically acceptable salt or the pharmaceutically acceptable solvate can be produced from the compound represented by Formula (I).

The term "anhydrate" used in the present specification is synonymous with "ansolvate" "non-solvate", "anhydride", and "non-hydrate".

The term "wet pulverization" used in the present specification means that the compound represented by Formula (I) or the like is subjected to a wet pulverization treatment with a suspension of a solvent by a wet pulverizer. Examples of the wet pulverization include a method for pulverizing with a shear force, a shear stress, a frictional force, or the like by a pulverizing medium, a method for pulverizing with a shear stress or a frictional force between pulverizing materials, a method for pulverizing by colliding a high-pressure fluid, a method for pulverizing by passing through a narrow gap, and the like, and the wet pulverization is not particularly limited in the present invention.

In the wet pulverization, water, an organic solvent, or a mixed solvent thereof can be used. The water used in the wet pulverization is not particularly limited, but it is preferable to use purified water usually used in production of pharmaceuticals and the like. As the organic solvent, alcohol, acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, formamide, hexane, methylbutyl ketone, methylcyclohexane, N-methylpyrrolidone, nitromethane, pyridine, sulfolane, tetralin, toluene, 1,1,2-trichloroethene, xylene, acetic acid, anisole, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, methyl ethyl ketone, methyl isobutyl ketone, pentane, propyl acetate, tetrahydrofuran, acetone, 1,1-diethoxypropane, 1,1-dimethoxymethane, 2,2-dimethoxypropane, isooctane, isopropyl ether, methyl isopropyl ketone, methyl tetrahydrofuran, petroleum ether, trichloroacetic acid, trifluoroacetic acid, 3-methyl-1-butanol, 2-methyl-1-propanol, and the like can be used. As the alcohol, methanol, 2-propanol, ethanol, t-butanol, 2-ethoxyethanol, ethylene glycol, methanol, 2-methoxyethanol, 1-butanol, 2-butanol, 1-pentanol, 1-propanol, 3-methyl-1-butanol, 2-methyl-1-propanol, and the like can be used. Methanol and/or 2-propanol is preferable. As the mixed solvent, a mixed solvent of water and alcohol is desirable. A mixing ratio of water and alcohol is water:alcohol=0.01 to 99.9:99.9 to 0.01, preferably 15 to 60:85 to 40, and more preferably 20 to 50:80 to 50.

Wet-pulverizing the compound represented by Formula (I) or the like includes, for example, wet-pulverizing a crystal of the compound represented by Formula (I) or the like, wet-pulverizing an amorphous substance of the compound represented by Formula (I) or the like, and wet-pulverizing a solution of the compound represented by Formula (I) or the like.

Wet-pulverizing the crystal of the compound represented by Formula (I) or the like includes, for example, wet-pulverizing an anhydrate crystal of the compound represented by Formula (I) and wet-pulverizing a dihydrate crystal of the compound represented by Formula (I).

Wet-pulverizing the crystal of the compound represented by Formula (I) includes a step of refining the crystal, preferably a step of controlling a 90% particle size distribution to be 100 μm or less.

The step of refining the crystal includes treatment at a pressure of 10 megapascals to 100 megapascals (preferably 60 to 90 megapascals, particularly preferably 70 megapascals) at a temperature of 0° C. to 60° C. (preferably 10° C. to 55° C., particularly preferably 25±5° C.) for 2 passes to 80 passes (preferably 3 to 10 passes, particularly preferably 5 to 7 passes) for 2 hours to 80 hours (preferably 3 hours to 10 hours, particularly preferably 5 hours to 7 hours) using a pressure type homogenizer.

Note that the pass is a unit indicating a theoretical treatment number, and the theoretical treatment number is obtained by the following calculation formula.

(Calculation formula)

Treatment time required for one pass($h$)=amount of slurry liquid($L$)/treatment speed of wet pulverizer($L/h$) (Mathematical formula 1)

Theoretical treatment number(pass)=treatment time ($h$)/treatment time required for one pass($h$) (Mathematical formula 2)

The term "crystal" used in the present specification means a solid in which atoms, ions, molecules, and the like constituting the crystal are three-dimensionally and regularly arranged, and is distinguished from an amorphous solid not having such a regular internal structure. The crystal of the present invention may be a single crystal, a twin crystal, a polycrystal, or the like.

Furthermore, in the "crystal", there may be a "crystalline polymorphism" that has the same composition but has different arrangement in the crystal, and crystals including these are referred to as "crystalline forms".

The crystal used in the present specification may be any of these, salts, hydrates, solvates, and crystalline polymorphisms, even a mixture of two or more is intended to be included in the scope of the invention.

The crystalline form and the crystallinity can be measured by many techniques including, for example, X-ray powder diffraction measurement. Raman spectroscopy, infrared absorption spectroscopy, moisture adsorption/desorption measurement, differential scanning calorimetry, and dissolution characteristics.

(X-Ray Powder Diffraction (XRPD))

X-ray powder diffraction (XRPD) is one of the most sensitive analytical methods for measuring the crystalline form and crystallinity of a solid. When the crystal is irradiated with X-rays, the X-rays are reflected by the crystal lattice planes and interfere with each other, and ordered diffraction lines corresponding to the period of the structure are shown. On the other hand, an amorphous solid usually does not have an ordered repetition period in its structure, so that a diffraction phenomenon does not occur and shows a featureless broad XRPD pattern (also referred to as a halo pattern).

The crystalline form of the compound represented by Formula (I) or the like can be identified by X-ray powder diffraction patterns and characteristic diffraction peaks.

Characteristic diffraction peaks used in the present specification are those selected from the observed diffraction patterns. The characteristic diffraction peaks are preferably selected from about 10 peaks, more preferably about 5 peaks, in a diffraction pattern.

In distinguishing a plurality of crystals, a peak that is observed in a crystal and is not observed in the other crystals, rather than the intensity of the peak, is a preferred characteristic peak in identifying the crystal. With such a characteristic peak, even one or two peaks can characterize the crystal. When the charts obtained by the measurement are compared and these characteristic peaks coincide with each other, it can be said that the X-ray powder diffraction spectra substantially coincide with each other.

In general, since the diffraction angle (2θ) in X-ray powder diffraction may have an error within a range of ±0.2°, the value of the diffraction angle of X-ray powder diffraction needs to be understood as including a numerical value within a range of about ±0.2°. Therefore, the present invention includes not only crystals in which the diffraction angles of peaks in X-ray powder diffraction completely coincide with each other, but also crystals in which the diffraction angles of peaks coincide with each other with an error of about ±0.2.

It is generally known that the intensities of the peaks displayed in the following tables and figures can vary depending on many factors, for example, the effect of a selective orientation of a crystal on X-ray beam, the effect of coarse particles, the purity of a substance to be analyzed or the crystallinity of a sample. The peak position can also be shifted based on the height variation of the sample. Further, different shifts are obtained according to the Bragg equation ($n\lambda=2d \sin \theta$) when measurement is carried out using a different wavelength, and such a different XRPD pattern obtained by using a different wavelength is also within the scope of the present invention.

(Single Crystal Structure Analysis)

This is one of methods for identifying a crystal, and it is possible to obtain crystallographic parameters in the crystal, atomic coordinates (values indicating a spatial positional relationship of each atom), and a three-dimensional structure model. See Toshio SAKURAI, "X-sen Kozo Kaiseki no Tebiki (Guide to X-ray Structural Analysis)", published by Shokabo Co., Ltd. (1983), and Stout & Jensen, "X-Ray Structure Determination: A Practical Guide", Macmillan Co., New York (1968), and the like. Single crystal structure analysis is useful for identifying a structure of a crystal of a compound having tautomerism as in the present invention.

(Raman Spectroscopy)

A Raman spectrum shows vibrational features of molecules or a complex system. Its origin lies in inelastic collisions between molecules and photons as particles of light including light rays. The collision of molecules with photons leads to an exchange of energy, which results in a change in energy, which in turn changes the wavelength of the photons. That is, since the Raman spectrum is a spectral line that is emitted when photons are incident on a target molecule and has an extremely narrow wavelength, a laser or the like is used as a light source. The wavelength of each Raman line is represented by a wavenumber shift from an incident light, which is a difference between an inverse of the wavelength of the Raman line and that of the incident light. The Raman spectrum is used for measuring a vibrational state of a molecule, which is determined by its molecular structure.

In general, since an absorption band ($cm^{-1}$) in a Raman spectrum may have an error within a range of ±2 $cm^{-1}$, the value of the absorption peak should be understood as including a numerical value within a range of about ±2 cm E. Therefore, the present invention includes not only crystals in which the peaks in the absorption bands in the Raman spectra completely coincide with each other, but also crystals in which the peaks in the absorption bands coincide with each other with an error of about ±2 $cm^{-1}$.

(Thermogravimetry/Differential Thermal Analysis (TG/DTA))

TG/DTA is one of the main measurement methods of thermal analysis, and is a method for measuring weight and thermal properties of a substance as an aggregate of atoms and molecules.

TG/DTA is a method for measuring changes in weight and heat quantity of a pharmaceutically active ingredient with respect to temperature or time, and curves of TG (thermogravimetry) and DTA (differential thermal analysis) are obtained by plotting the obtained data with respect to temperature or time. From the TG/DTA curves, it is possible to obtain information on weight and heat quantity change regarding decomposition, dehydration, oxidation, reduction, sublimation, and evaporation of the pharmaceutically active ingredient.

For TG/DTA, it is known that the observed temperature and weight change may depend on temperature change rate as well as a sample preparation technique and specific equipment used. Thus, the "melting point" in TG/DT A refers to onset temperature that is less susceptible to sample preparation techniques. In recognition of the identity of crystals, not only the melting point but also the overall pattern is important, and the overall pattern may slightly vary depending on measurement conditions and a measuring instrument.

(Differential Scanning Calorimetry (DSC))

DSC is one of the main measurement methods of thermal analysis, and is a method for measuring thermal properties of a substance as an aggregate of atoms and molecules.

A differential scanning calorimetry curve is obtained by measuring a change in heat quantity with respect to temperature or time of the pharmaceutically active ingredient by DSC and plotting the obtained data with respect to temperature or time. From the differential scanning calorimetry curve, it is possible to obtain information on the onset temperature when the pharmaceutically active ingredient is melted, the maximum value of the endothermic peak curve associated with melting, and enthalpy.

For DSC, it is known that the observed temperature may depend on temperature change rate as well as a sample preparation technique and specific equipment used. Thus, the "melting point" in DSC refers to onset temperature that is less susceptible to sample preparation techniques. An error range at the onset temperature obtained from the differential scanning calorimetry curve is approximately +2° C. In recognition of the identity of crystals, not only the melting point but also the overall pattern is important, and the overall pattern may slightly vary depending on measurement conditions and a measuring instrument.

(Moisture Adsorption/Desorption Isotherm Measurement Method (DVS))

The moisture adsorption/desorption isotherm measurement is a measurement method for measuring the adsorption and desorption behavior of moisture by measuring a weight change in a solid as a measurement target under each relative humidity condition.

As a basic measurement method based on the dry weight at 0% RH (relative humidity 0%), the relative humidity is increased every 5% or 10%, and after the weight is stabilized at each relative humidity, the amount of adsorbed water can be determined from the weight increase from the reference value. Similarly, the desorption amount of water can be measured by decreasing the relative humidity every 5% or 10% from 100% RH (relative humidity 100%).

By plotting the value of the weight change at each relative humidity, an adsorption/desorption isotherm can be obtained. From this result, it is possible to consider a phenomenon of adsorption and desorption of adhering moisture at each humidity. In addition, when an anhydrate crystal and a hydrate crystal mutually undergo crystal transition due to humidity, it is possible to calculate the humidity at which the crystal transition occurs and the amount of crystal water.

Adsorption and desorption of adhering water and crystal water are affected by particle size, crystallinity, crystal habit, and the like, so that the measurement results may slightly change.

Wet-pulverizing an amorphous substance such as the compound represented by Formula (I) or the like is also included in the present invention.

The term "amorphous (substance)" used in the present specification means a substance in which atoms, ions, molecules, and the like constituting the substance do not have a three-dimensional regular and correct arrangement property, and the amorphous substance can be measured by many techniques including, for example, X-ray powder diffraction measurement, Raman spectroscopy, infrared absorption spectroscopy, moisture adsorption/desorption measurement, differential scanning calorimetry, and dissolution characteristics. A substance may become amorphous by pulverization, freeze drying, spray drying, and the like.

Wet-pulverizing a solution of the compound represented by Formula (I) or the like includes wet-pulverizing a supersaturated solution of the compound represented by Formula (I) or the like. The solution of the compound represented by Formula (I) or the like may be obtained by dissolving the compound represented by Formula (I) or the like in a solvent, or may be obtained by hydrolyzing a compound (9) to produce the compound represented by Formula (I) or the like.

Wet-pulverizing the supersaturated solution such as the compound represented by Formula (I) or the like may include a step of forming a nucleus of a crystal from the supersaturated solution, a step of crystal-growing the nucleus obtained in the step, a step of controlling crystal growth, and a step of refining the crystal obtained.

The step of forming a nucleus of a crystal from the supersaturated solution includes a case of forming a nucleus of a crystal by physical stimulation or the like by a wet pulverizer, a case of forming a nucleus of a crystal using a seed crystal, and a case of forming a nucleus of a crystal by temperature control.

In the step of crystal-growing the nucleus obtained, when an anhydrate crystal and/or a dihydrate crystal of the compound represented by Formula (I) is produced, treatment at a pressure of 1 megapascal to 100 megapascals (preferably 5 megapascals to 20 megapascals, particularly preferably 10 megapascals) at a temperature of 0° C. to 60° C. (preferably 10° C. to 55° C., particularly preferably 25±5° C.) for 5 minutes to 10 hours (preferably 15 minutes to 8 hours, particularly preferably 30 minutes to 3 hours) using a pressure type homogenizer is included.

As another aspect, wet-pulverizing the supersaturated solution such as the compound represented by Formula (I) or the like may include a step of producing a dihydrate crystal of the compound represented by Formula (I) from the supersaturated solution, a step of producing an anhydrate crystal of the compound represented by Formula (I) from the crystal obtained in the step, and a step of controlling a 90% particle size distribution of the crystal obtained in the step to be 100 pin or less.

In the step of producing a dihydrate crystal of the compound represented by Formula (I) from the supersaturated solution, treatment at a pressure of 1 megapascal to 100 megapascals (preferably 5 megapascals to 20 megapascals, particularly preferably 10 megapascals) at a temperature of 0° C. to 0° C. (preferably 10° C. to 55° C., particularly preferably 25±5° C.) for 5 minutes to 10 hours (preferably 15 minutes to 5 hours, particularly preferably 30 minutes to 1 hour) using a pressure type homogenizer is included.

The step of producing an anhydrate crystal of the compound represented by Formula (I) from the crystal obtained in the step includes a step of heating and cooling. The step of heating includes a step of heating to a temperature of 30° C. to 80° C. (preferably 40° C. to 65'C, particularly preferably 50° C.). The step of cooling includes a step of heating to a temperature of 0° C. to 50° C. (preferably 10° C. to 10° C., particularly preferably 25° C.). In this step, it is desirable to use a seed crystal of an anhydrate crystal of the compound represented by Formula (I).

In the step of controlling a 90% particle size distribution of the crystal obtained in the step to be 100 μm or less, treatment at a pressure of 10 megapascals to 100 megapascals (preferably 60 megapascals to 90 megapascals, particularly preferably 70 megapascals) at a temperature of 0° C. to 60° C. (preferably 10° C. to 55° C., particularly preferably 25° C.±5° C.) for 2 hours to 80 hours (preferably 3 hours to 10 hours, particularly preferably 5 hours to 7 hours) using a pressure type homogenizer is included. Note that the pass is a unit indicating a theoretical treatment number, and the theoretical treatment number is obtained by the calculation formula (Mathematical Formula 1).

As the wet pulverizer, a rotor-stator, a pressure type homogenizer, a ball mill, a medium mill, ultrasonic crushing, or the like can be used. A rotor-stator, a pressure type homogenizer, and a ball mill are preferable, and a pressure type homogenizer is particularly preferable.

The rotor-stator is a wet pulverizer that generates a shear force and a propulsive force generated by rotating the rotor at a high speed, and mixes, emulsifies, disperses, and crushes by a high vortex flow generated in a shear groove between the rotor and the stator.

The ball mill is a wet pulverizer in which a pulverizing medium (steel ball, sill pep, pebble, or the like) is placed in a cylindrical drum and pulverized while rotating the trunk. The ball mill also includes a bead mill.

The pressure type homogenizer is a wet pulverizer that emulsifies, disperses, and crushes a sample using energy such as collision between particles caused by ejecting a pressurized sample from a gap, shear force due to a pressure difference, and destructive force of collision to an impact ring.

Wet pulverization can be performed by any of a batch type method, a semi-continuous type method, and a continuous type method. Preferably, the method is a continuous type method. The continuous type method can be performed by a recirculation loop.

The wet pulverization step can be performed in one pot. One pot means that a plurality of steps are performed in one reaction vessel or apparatus.

As the crystal of the compound represented by Formula (I) or the like obtained by the method for producing a crystal of the compound represented by Formula (I) or the like of the present invention or the crystal of the compound represented by Formula (I) or the like that has been wet-pulverized, preferred is a crystal that does not contain the compound represented by Formula (III) or contains the compound represented by Formula (III) and has a content ratio of the compound represented by Formula (III) to an amount of the compound represented by Formula (I) of 0.0001 to 80 ppm. Furthermore, as the crystal of the compound represented by Formula (I) or the like obtained by the method for producing a crystal of the compound represented by Formula (I) or the like of the present invention or the crystal of the compound represented by Formula (I) or the like that has been wet-pulverized, more preferred is a crystal that does not contain the compound represented by Formula (III) or contains the compound represented by Formula (III) and has a content ratio of the compound represented by Formula (III) to an amount of the compound represented by Formula (I) of 0.0001 to 10 ppm.

The phrase "does not contain the compound represented by Formula (III)" means that the compound represented by Formula (III) is not contained, or even if the compound represented by Formula (III) is contained, the amount of the compound represented by Formula (III) is below a detection limit, and the compound represented by Formula (III) cannot be detected.

By wet-pulverizing the compound represented by Formula (I) or the like to produce a crystal of the compound represented by Formula (I) or the like, the compound represented by Formula (III) is not contained, or the content ratio of the compound represented by Formula (III) can be 0.0001 to 30 ppm, preferably 0.0001 to 10 ppm.

Examples of the crystal of the compound represented by Formula (I) or the like that does not contain the compound represented by Formula (III) include a dihydrate crystal of the compound represented by Formula (I).

The compound represented by Formula (ITI) is described in Chemische Berichte (1959), 92, 724-32. It is also used as a synthetic raw material for the compound represented by Formula (I) or the like.

In particular, as the crystal of the compound represented by Formula (I) or the like obtained by wet-pulverizing the compound represented by Formula (I) or the like, preferred is a crystal in which when a stability testing is performed under a condition of 40±2° C. and a relative humidity of 75±5% (glass bottle opened) for 6 months, the compound represented by Formula (lii) is not detected, or the content ratio of the compound represented by Formula (III) to the amount of the compound represented by Formula (I) or the like is 0.0001 to 30 ppm. Furthermore, as the crystal of the compound represented by Formula (I) or the like obtained by wet-pulverizing the compound represented by Formula (I) or the like, more preferred is a crystal in which when a stability testing is performed under a condition of 10±2° C. and a relative humidity of 75±5% (glass bottle opened) for 1 month, the compound represented by Formula (III) is not detected, or the content ratio of the compound represented by Formula (III) to the amount of the compound represented by Formula (I) or the like is 0.0001 to 10 ppm.

The crystal of the present invention also includes a crystal in which when a stability testing is performed under a condition of 25±2° C. and a relative humidity of 60±5% (glass bottle opened) for 12 months or 30±2° C. and a relative humidity of 65±5% (glass bottle opened) for 12 months, the content ratio of the compound represented by Formula (III) to the amount of the compound represented by Formula (I) or the like is 00001 to 30 ppm.

The above temperature and relative humidity vary, but the present invention also includes a crystal of the compound represented by Formula (I) or the like in which when a stability testing is performed for a period as a condition at any temperature and relative humidity included in the above range, the content ratio of the compound represented by Formula (III) to the amount of the compound represented by Formula (I) or the like is 0.0001 to 30 ppm. Under a condition of either glass bottle opened or low-density polyethylene baa, the content ratio of the compound represented by Formula (III) to the amount of the compound represented by Formula (I) or the like may be 0.0001 to 30 ppm.

The crystal is preferably a crystal of the compound represented by Formula (I) or the like in which the content ratio of the compound represented by Formula (III) to the amount of the compound represented by Formula (I) or the like is 0.0001 to 20 ppm, and more preferably 0.0001 to 10 ppm.

The crystal of the present invention can suppress production of the compound represented by Formula (III) in a stability testing.

The compound represented by Formula (III) is considered to be generated by decomposition of the compound represented by Formula (I) or the like. When a stability testing is performed using the compound represented by Formula (I) or the like, the amount of the compound represented by Formula (III) increases. However, by producing a crystal of the compound represented by Formula (I) or the like by the production method of the present invention, it is possible to suppress an increase in the amount of the compound represented by Formula (III) in a stability testing. In addition, by producing a pharmaceutical composition containing the compound represented by Formula (I) or the like by the method for producing a pharmaceutical composition of the present invention, it is possible to suppress an increase in the amount of the compound represented by Formula (III) in a stability testing.

The content ratio of the compound represented by Formula (III) can be determined by dividing the amount of the compound represented by Formula (III) by the amount of the compound represented by Formula (I) or the like. The amount of each compound contained in the crystal of the compound represented by Formula (I) or the like and the amount of each compound contained in the pharmaceutical composition can be determined from a peak area obtained by chromatographic analysis. For example, the content of the compound represented by Formula (III) is determined by comparing a peak area of the compound represented by Formula (III) obtained by chromatographic analysis of a standard solution of the compound represented by Formula (III) with a peak area of the compound represented by Formula (III) obtained by chromatographic analysis of a measurement sample, and using the value, a weight ratio with respect to the compound represented by Formula (I) or the like is determined, whereby the content ratio can be calculated. As the amount of the compound represented by Formula (I) or the like, a theoretical content of the compound represented by Formula (I) or the like at the time of preparing a measurement sample can be used because the amount of the compound represented by Formula (I) or the like that decomposes is very small.

The crystal and the pharmaceutical composition of the compound represented by Formula (I) or the like in which the content ratio of the compound represented by Formula (III) is 0.0001 to 10 ppm or less means a crystal and a pharmaceutical composition in which the amount of the compound represented by Formula (III) can be detected, the content ratio of the compound represented by Formula (III) can be calculated, and the content ratio is 10 ppm or less.

As the crystal obtained by the present invention, a crystal having a 90% particle size distribution of 100 μm or less is preferred. In particular, the 90% particle size distribution is preferably 0.5 μm or more and 50 μm or less, more preferably 0.5 μm or more and 10 μm or less.

In a graph in which a relative particle amount is plotted on the vertical axis and a particle size is plotted on the horizontal axis, a particle size at a point where a distribution curve of integration % intersects the horizontal axis of 90% is referred to as a 90% particle size distribution.

As the crystal obtained by the present invention, an anhydrate crystal of the compound represented by Formula (I) and a dihydrate crystal of the compound represented by Formula (I) are preferable. In particular, an anhydrate crystal of the compound represented by Formula (I) is preferable.

As the crystal of the present invention, a crystal of the compound represented by Formula (I) or the like obtained by the production method of the present invention is preferable. In particular, an anhydrate crystal of the compound represented by Formula (I) obtained by the production method of the present invention is preferable.

That is, as the crystal of the present invention, a crystal of the compound represented by Formula (I) or the like that has been wet-pulverized is preferable. In particular, an anhydrate crystal of the compound represented by Formula (I) that has been wet-pulverized is preferable.

As a result of single crystal structure analysis, the anhydrate crystal of the compound represented by Formula (I) was confirmed to have the following molecular structure,

[Chemical Formula 6]

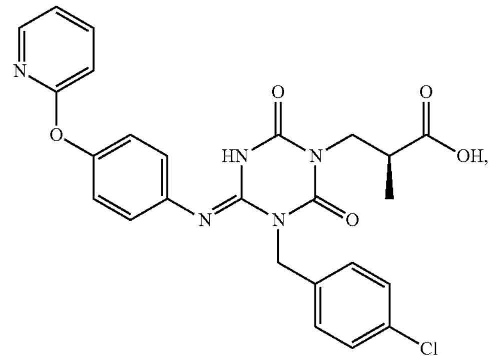

X-ray powder diffraction peaks characteristic of the anhydrate crystal of the compound represented by Formula (I) are at X-ray powder diffraction angles (2θ): 7.9°, 9.3°, 12.6°, 12.9°, 15.8°, 17.2°, 19.4°, 21.7°, 23.9° 25.4°, 26.6°, 27.8°, or 32.8°, each also including a numerical value within a range of about 0.2°. For example, the anhydrate crystal of the compound represented by Formula (I) can be identified as a crystal that exhibits characteristic X-ray powder diffraction peaks at diffraction angles (2θ): 15.8±0.2°, 19.4°±0.2°, 21.7°±0.2°, 23.9°±0.2°, and 25.4°±0.2°, or a crystal that exhibits characteristic X-ray powder diffraction peaks at diffraction angles (2θ): 7.9°±0.2°, 9.3°±0.2°, 12.9±0.2°, 15.8°±0.2°, and 19.4°±0.2°.

The present invention also includes a method for producing a pharmaceutical composition containing a compound represented by Formula (I) or the like, the method including a step of producing a crystal of the compound represented by Formula (I) or the like by wet-pulverizing the compound represented by Formula (I) or the like.

In addition, as the method for producing a pharmaceutical composition containing the compound represented by Formula (I) or the like, preferred is a production method using an anhydrate crystal of the compound represented by Formula (I) obtained by the method for producing a crystal of the present invention or an anhydrate crystal of the compound represented by Formula (I) of the present invention.

The method for producing a pharmaceutical composition mentioned above may further include other steps. For example, any method of dry mixing, dry granulation, wet kneading, and/or wet granulation may be included.

The present invention also relates to a method for producing a pharmaceutical composition containing a compound represented by Formula (I) or the like, the method including a step of wet-kneading and/or wet-granulating the compound represented by Formula (I) or the like.

In the method for producing a pharmaceutical composition mentioned above, as the compound represented by Formula (I) or the like used for wet kneading and/or wet granulation, any of a compound obtained by dry pulverization and a compound obtained by wet pulverization can be used. In particular, the method for producing a pharmaceutical composition of the present invention is useful when the compound represented by Formula (I) or the like obtained by dry pulverization is used. The compound represented by Formula (I) or the like obtained by dry pulverization contains a large amount of an amorphous compound represented by Formula (I) or the like. This amorphous compound represented by Formula (I) or the like is considered to contribute to production of the compound represented by Formula (III). By using the method for producing a pharmaceutical composition of the present invention, it is possible to crystallize the amorphous compound represented by Formula (I) or the like under wet kneading and/or wet granulation, it is possible to reduce the amount of the amorphous compound represented by Formula (I) or the like in the pharmaceutical composition, and it is possible to suppress the production of the compound represented by Formula (III) in a stability testing.

The term "wet kneading and/or wet granulation" used in the present specification means that the compound represented by Formula (I) or the like is treated in a hydrous state, and is not limited to a specific treatment. Examples of the "wet kneading and/or wet granulation" include wet kneading in which a solution containing a hydroxycarboxylic acid ester, a polyhydric alcohol ester, and/or a polyether is added to a powder containing the compound represented by Formula (I) or the like, followed by kneading, and wet granulation in which a mixture is kneaded and then a wet granule is produced. In addition, the wet granulation method can be subdivided into methods such as a mixing and stirring granulation method using a planetary mixer, a screw mixer, or the like, a high-speed mixing and stirring granulation method using a Henschel mixer, a super mixer, or the like, an extrusion granulation method using a cylindrical granulator, a rotary granulator, a screw extrusion granulator, a pellet mill granulator, or the like, a tumbling granulation method, a fluidized bed granulation method, a spray granulation method, and the like, and the present invention can be carried out by any method.

Water used in the "wet kneading and/or wet granulation" in the present invention is not particularly limited, but it is preferable to use purified water usually used in production of pharmaceuticals and the like. When water is added for the "wet kneading and/or wet granulation", water alone may be added, or water may be added as a mixed solvent in which an organic solvent such as alcohol is mixed with water. In these cases, water (water-containing solvent) may be added alone, or may be added in a state in which a soluble component is dissolved or in a state in which an insoluble component is suspended. Moisture at the time of granulation with respect to a mixed powder is 1 to 70%, preferably 5 to 50%, and more preferably 15 to 30%.

In addition, it is preferable to use a hydroxycarboxylic acid ester, a polyhydric alcohol ester, and/or a polyether in the step of wet kneading and/or wet granulation. It is more preferable to use the hydroxycarboxylic acid ester, the polyhydric alcohol ester, and/or the polyether dissolved or suspended in water used for wet kneading and/or wet granulation. It is further preferable to use the hydroxycarboxylic acid ester, the polyhydric alcohol ester, and/or the polyether dissolved or suspended in a binder solution obtained by dissolving a binder in water.

The hydroxycarboxylic acid ester means a hydroxycarboxylic acid ester or a hydroxy protected product thereof. The hydroxycarboxylic acid ester refers to an ester form of a carboxylic acid having a hydroxy group. The hydroxy protected product means a hydroxycarboxylic acid ester in which a hydroxy group is protected by a protecting group. Examples of the protecting group include a formyl group and an acyl group. Specific examples thereof include trimethyl citrate, triethyl citrate, tripropyl citrate, tributyl citrate, trimethyl O-acetylcitrate, triethyl O-acetylcitrate, tripropyl O-acetylcitrate, tributyl O-acetylcitrate, methyl O-acetylricinoleate, and trihexyl O-butylcitrate. Particularly preferred is triethyl citrate.

The polyhydric alcohol ester refers to an ester form of an alcohol having two or more hydroxyl groups in the molecule, and in the polyhydric alcohol, the hydroxyl groups are attached to different carbon atoms. Specific examples thereof include miglyol (medium-chain triglyceride, and examples thereof include miglyol 812, miglyol 810, and miglyol 829), triacetin, polysorbate 20, polysorbate 60, polysorbate 80, and oils and fats (refer to an ester form of glycerin and a saturated or unsaturated higher fatty acid, and examples thereof include sesame oil, corn oil, olive oil, and soybean oil), preferably miglyol and triacetin, and more preferably miglyol.

The polyether is a compound having a continuous structure of $—CR_2—O—CR_2$. Specific examples thereof include macrogol 6000, polysorbate 20, polysorbate 60, and polysorbate 80.

As the hydroxycarboxylic acid ester, the polyhydric alcohol ester, and/or the polyether, preferably, one or more selected from the group consisting of triethyl citrate, miglyol (miglyol 812, miglyol 810, and miglyol 829), triacetin, macrogol 6000, polysorbate 20, polysorbate 60, polysorbate 80, and fats and oils (sesame oil, corn oil, olive oil, soybean oil, and the like) can be used.

In the present invention, one or more additives selected from the group consisting of an excipient, a binder, and a disintegrant may be used in the step of wet kneading and/or wet granulation.

In the present invention, an excipient (also referred to as a filler in some cases) may be used. In addition, since there is a possibility that impurities and related substances increase depending on the excipient, it is necessary to select an excipient that does not increase impurities and related substances. As the excipient, excipients described in the Japanese Pharmacopoeia, the Japanese Pharmaceutical Codex, the Japanese Pharmaceutical Excipients, the Japan's Specifications and Standards for Food Additives, or the like can be used. Examples of the excipient include sugar derivatives, starch derivatives, cellulose derivatives, inorganic excipients, ß-cyclodextrin, magnesium stearate, calcium stearate, sucrose fatty acid ester, crospovidone, soybean lecithin, powdered tragacanth, gum arabic, dextran, and pullulan.

Examples of the sugar derivatives include sugars and sugar alcohols, examples of the sugars include lactose, white soft sugar, glucose, fructose, and sucrose, and examples of the sugar alcohols include mannitol, sorbitol, erythritol, xylitol, powdered maltose starch syrup, and maltitol.

Examples of the starch derivatives include starch, potato starch, corn starch (cornstarch), rice starch, partly pregelatinized starch, pregelatinized starch, porous starch, carboxystarch sodium, hydroxypropyl starch, low-substituted carboxymethyl starch, and carboxymethyl starch.

Examples of the cellulose derivatives include crystalline cellulose, powder cellulose, carmellose sodium, carmellose, croscarmellose sodium, carmellose calcium, carboxymethylethylcellulose, and low-substituted hydroxypropylcellulose.

Examples of the inorganic excipients include silicate derivatives, phosphates, carbonates, sulfates, magnesium oxide, titanium oxide, calcium lactate, synthetic hydrotalcite, talc, kaolin, dried aluminum hydroxide, magnesium oxide, and bentonite.

Examples of the silicate derivatives include silicon dioxides such as hydrated silicon dioxide and light anhydrous silicic acid, magnesium aluminometasilicate, synthetic aluminum silicate, and calcium silicate.

Examples of the phosphates include anhydrous dibasic calcium phosphate, calcium monohydrogen phosphate, calcium hydrogen phosphate, sodium hydrogen phosphate, dipotassium phosphate, potassium dihydrogen phosphate, calcium dihydrogen phosphate, and monobasic sodium phosphate.

Examples of the carbonates include precipitated calcium carbonate, calcium carbonate, and magnesium carbonate. Examples of the sulfates include calcium sulfate.

Two or more kinds of these excipients may be mixed at an appropriate ratio and then used.

The excipient in the formulation of the present invention is preferably lactose. A sugar alcohol saccharide and a sugar alcohol may be mixed and then used. In this case, a sugar alcohol and a saccharide may be combined, a sugar alcohol and another sugar alcohol may be combined, or a saccharide and another saccharide may be combined.

In the present invention, a binder may be used, and binders described in the Japanese Pharmacopoeia, the Japanese Pharmaceutical Codex, the Japanese Pharmaceutical Excipients, the Japan's Specifications and Standards for Food Additives, or the like can be used. Examples of the binder include a cellulose-based binder, a starch-based binder, a vinyl-based binder, polyether, gum arabic, gum arabic powder, powdered acacia, alginic acid, sodium alginate, sucrose, gelatin, dextrin, pullulan, tragacanth, powdered tragacanth, xanthane gum, pectin, sodium polyacrylate, agar, powdered phellodendron bark, guar gum, light anhydrous silicic acid, and hardened oil.

Examples of the cellulose-based binder include carboxymethylcellulose (carmellose, CMC), carboxymethylcellulose sodium (carmellose sodium), hydroxyethyl cellulose (HEC), hydroxypropylcellulose (HPC), hydroxypropyl methylcellulose (hypromellose) (HPMC), methylcellulose (MC), crystalline cellulose, microcrystalline cellulose, ethylcellulose, crystalline cellulose-carmellose sodium, carmellose calcium, powder cellulose, and low-substituted hydroxypropylcellulose.

Examples of the starch-based binders include starch, pregelatinized starch, partly pregelatinized starch, potato starch, wheat starch, rice starch, porous starch, corn starch, hydroxypropyl starch, and sodium starch glycolate (sodium carboxymethyl starch).

Examples of the vinyl-based binder include polyvinyl alcohol (PVA), polyvinylpyrrolidone (povidone) (PVP), carboxy vinyl polymer, and copolyvidone.

Examples of the polyether include macrogol (polyethylene glycol) 200, macrogol 300, macrogol 400, macrogol 600, macrogol 1000, macrogol 1500, macrogol 1540, macrogol 4000, macrogol 6000, macrogol 20000, glycerin, polyoxyethylene [105] polyoxypropylene [5]glycol, and propylene glycol.

Two or more kinds of these binders may be mixed at an appropriate ratio and then used.

The binder in the formulation of the present invention is preferably hydroxypropylcellulose (HPC).

In the present invention, a disintegrant may be used, and disintegrants described in the Japanese Pharmacopoeia, the Japanese Pharmaceutical Codex, the Japanese Pharmaceutical Excipients, the Japan's Specifications and Standards for Food Additives, or the like can be used. Examples of the disintegrant include a cellulose-based disintegrant, a starch-based disintegrant, a vinyl-based disintegrant, and magnesium aluminometasilicate.

Examples of the cellulose-based disintegrant include carmellose, carmellose calcium, carmellose sodium, hydroxypropylcellulose, low-substituted hydroxypropylcellulose, croscarmellose sodium (Ac-Di-Sol), crystalline cellulose, and powder cellulose.

Examples of the starch-based disintegrant include partly pregelatinized starch, potato starch, cornstarch, hydroxypropyl starch, sodium carboxymethyl starch, low-substituted sodium carboxymethyl starch, sodium starch glycolate, pregelatinized starch, and starch.

Examples of the vinyl-based disintegrant include crospovidone and polyvinyl alcohol.

Two or more kinds of these disintegrants may be mixed at an appropriate ratio and then used.

The disintegrant in the formulation of the present invention is preferably low-substituted hydroxypropylcellulose.

That is, it is possible to use one or more selected from the group consisting of lactose, hydroxypropylcellulose, and low-substituted hydroxypropylcellulose in the step of wet kneading and/or wet granulation.

The present invention also includes a pharmaceutical composition containing a compound represented by Formula (I) or the like, the pharmaceutical composition being obtained by the method for producing the pharmaceutical composition of the present invention.

The pharmaceutical composition of the present invention also includes a pharmaceutical composition containing a crystal of a compound represented by Formula (I) or the like, the crystal being obtained by the method for producing the crystal of the present invention. In particular, a pharmaceutical composition containing an anhydrate crystal of the compound represented by Formula (I) is preferable.

The present invention also includes a pharmaceutical composition containing a compound represented by Formula (I) or the like, the pharmaceutical composition being obtained by the production method of the present invention. The production method of the present invention may include other steps. The present invention also includes a pharmaceutical composition containing the compound represented by Formula (I) or the like that has been wet-kneaded and/or wet-granulated.

As the pharmaceutical composition of the present invention, preferred is a pharmaceutical composition that does not contain a compound represented by Formula (III) or contains the compound represented by Formula (III) and has a content ratio of the compound represented by Formula (III) to an amount of the compound represented by Formula (I) or the like of 0.0001 to 10 ppm. The phrase "does not contain the compound represented by Formula (III)" means that the compound represented by Formula (III) is not contained, or even if the compound represented by Formula (III) is contained, the amount of the compound represented by Formula (III) is below a detection limit, and the compound represented by Formula (III) cannot be detected.

In particular, preferred is a pharmaceutical composition in which when a stability testing is performed under a condition of 40±2° C. and a relative humidity of 75±5% (glass bottle opened) for G months, the compound represented by Formula (III) is not detected, or the content ratio of the compound represented by Formula (III) to the amount of the compound represented by Formula (I) or the like is 0.0001 to 30 ppm.

Furthermore, more preferred is a pharmaceutical composition in which when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I) or the like is 0.0001 to 10 ppm.

The pharmaceutical composition of the present invention also includes a pharmaceutical composition in which when a stability testing is performed under a condition of 25±2° C. and a relative humidity of 60±5% (glass bottle opened or low-density polyethylene bag) for 12 months or 30±2° C. and a relative humidity of 65±5% (glass bottle opened or low-density polyethylene bag) for 12 months, the content ratio of the compound represented by Formula (III) to the amount of the compound represented by Formula (I) or the like is 0.0001 to 30 ppm.

The above temperature and relative humidity vary, but the present invention also includes a pharmaceutical composition in which when a stability testing is performed for a period as a condition at any temperature and relative humidity included in the above range, the content ratio of the compound represented by Formula (III) to the amount of the compound represented by Formula (I) or the like is 0.0001 to 30 ppm. Under a condition of either glass bottle opened or low-density polyethylene bag, the content ratio of the compound represented by Formula (III) to the amount of the compound represented by Formula (I) or the like may be 0.0001 to 30 ppm.

The pharmaceutical composition is preferably a pharmaceutical composition in which the content ratio of the compound represented by Formula (III) to the amount of the compound represented by Formula (I) or the like is 0.0001 to 20 ppm, and more preferably 0.0001 to 10 ppm.

In the pharmaceutical composition of the present invention, the amount of the amorphous compound represented by Formula (I) or the like in the pharmaceutical composition is small, and it is possible to suppress the production of the compound represented by Formula (III) in a stability testing.

The stability testing may be performed under a condition of 40±2° C. and a relative humidity of 75%±5% (also referred to as 40±2° C./75±5% RH) for C months as an accelerated testing, or may be performed under a condition of 25±2° C. and a relative humidity of 60±5% (also referred to as 25±2° C./60±5% RH) for 12 months as a long-term testing. These tests can be performed under a condition of glass bottle closed or opened, or low-density polyethylene bag. Preferably, these tests are performed under a condition of glass bottle opened under the above relative humidity. A method for performing these stability tests is described in the Japanese Pharmacopoeia, and thus the stability tests can be performed according thereto.

The pharmaceutical composition of the present invention may be a solid formulation. Specifically, the solid formulation may be a granule, a fine granule, a tablet, a powder, a capsule, a pill, or the like, and is preferably a granule or a tablet. In the present specification, an uncoated formulation or an uncoated granule is, for example, a formulation or a granule that can be coated. An uncoated formulation of a powder, a fine granule, or a granule is referred to as an uncoated granule, and an uncoated formulation of a tablet is referred to as a core tablet.

Regarding the shape of the tablet, any shape can be adopted: specifically, the tablet can be formed into a shape of a circle, an ellipse, a sphere, a bar, or a donut. Furthermore, the tablet may be a multi-layer tablet, a dry-film-coated tablet, and the like, but is preferably a single-layer tablet, which is produced easily. In addition, impression such as a mark and a letter for improving discriminability, or a cleavage line for revision may be imparted.

The pharmaceutical composition of the present invention in a form of a tablet or a granule also includes a pharmaceutical composition containing a hydroxycarboxylic acid ester, a polyhydric alcohol ester, and/or a polyether in a core tablet or an uncoated granule. Examples of the hydroxycarboxylic acid ester, the polyhydric alcohol ester, and the polyether include those used in the method for producing a pharmaceutical composition of the present invention.

For example, preferred is a pharmaceutical composition containing a compound represented by Formula (I) or the like, the pharmaceutical composition being a tablet or a granule and containing one or more selected from the group consisting of triethyl citrate, miglyol (for example, miglyol 812, miglyol 810, and miglyol 829), triacetin, macrogol 6000, polysorbate 20, polysorbate 60, polysorbate 80, and fats and oils (sesame oil, corn oil, olive oil, soybean oil, and the like) in a core tablet or an uncoated granule.

As another aspect, preferred is a pharmaceutical composition containing a compound represented by formula (I) or the like, the pharmaceutical composition being a tablet or a granule and containing triethyl citrate in a core tablet or an uncoated granule.

A method for producing a granule that is the pharmaceutical composition of the present invention is not particularly limited, but is specifically a method for mixing an active ingredient, a hydroxycarboxylic acid ester, a polyhydric alcohol, and/or a polyether, and an additive such as an excipient to produce a mixed powder and then granulating the mixed powder, preferably a wet granulation method in which granulation is performed by adding water, or water or a solvent containing a binder.

A method for producing a tablet that is the pharmaceutical composition of the present invention is not particularly limited, but is specifically a tableting method in which a granule is produced by the above-mentioned method, a binder, a disintegrant, and a lubricant are further mixed with the granule, and the mixed granule is tableted with a tableting machine. As a machine for mixing an active ingredient, an additive, and the like, a V-type mixer or a container blender can be used. As the tableting machine, single tableting machine and rotary tableting machine can be used.

The hydroxycarboxylic acid ester, the polyhydric alcohol, and/or the polyether ester can be used in an amount of 0.001 to 15% by weight, preferably 0.01 to 10% by weight, more preferably 0.1 to 5% by weight, and still more preferably 0.1 to 2% by weight, based on a total amount of the pharmaceutical composition.

The hydroxycarboxylic acid ester, the polyhydric alcohol ester, and/or the polyether can be used in an amount of 0.0001 to 0.5 parts by weight, preferably 0.001 to 0.3 parts by weight, based on 1 part by weight of the compound.

Also in the pharmaceutical composition in a form of a tablet or a granule, the pharmaceutical composition containing a hydroxycarboxylic acid ester, a polyhydric alcohol ester, and/or a polyether in a core tablet or an uncoated granule, it is preferable that the compound represented by Formula (III) is contained, and the content ratio of the compound represented by Formula (III) to the amount of the compound represented by Formula (I) or the like is 0.0001 to 10 ppm. Furthermore, it is preferable that when a stability testing is performed under a condition of 40±2° C. and a relative humidity of 75±5% (glass bottle opened or low-density polyethylene bag) for 6 months, the content ratio of the compound represented by Formula (III) to the amount of the compound represented by Formula (I) or the like is 0.0001 to 30 ppm.

In the pharmaceutical composition of the present invention, the compound represented by Formula (I) or the like is contained in an amount of 1 to 1000 mg, preferably 10 to 450 mg, and more preferably 50 to 300 mg.

In the pharmaceutical composition of the present invention, a blending amount of the compound represented by Formula (I) or the like is 0.1 to 90% by weight, preferably 20 to 50% by weight, and more preferably 25 to 40% by weight, based on to the total amount of the pharmaceutical composition.

In the pharmaceutical composition of the present invention, the blending amount of the compound represented by Formula (I) or the like is 0.1 to 90% by weight, preferably 20 to 50% by weight, and more preferably 25 to 40% by weight, based on a total amount of a core tablet or an uncoated granule.

The pharmaceutical composition of the present invention may contain one or more additives selected from the group consisting of an excipient, a binder, a disintegrant, and a lubricant. Examples of the excipient, the binder, and the disintegrant include those used in the method for producing a pharmaceutical composition of the present invention mentioned above.

As the lubricant, lubricants described in the Japanese Pharmacopoeia, the Japanese Pharmaceutical Codex, the Japanese Pharmaceutical Excipients, the Japan's Specifications and Standards for Food Additives, or the like can be used. Examples of the lubricant include stearic acid and metallic stearate, an inorganic lubricant, a hydrophobic lubricant, a hydrophilic lubricant, and sodium stearyl fumarate.

Examples of the stearic acid and metallic stearate include magnesium stearate, calcium stearate, stearic acid, stearyl alcohol, and polyoxyl 40 stearate.

Examples of the inorganic lubricant include talc, light anhydrous silicic acid, hydrated silicon dioxide, magnesium carbonate, precipitated calcium carbonate, dried aluminum hydroxide gel, magnesium aluminometasilicate, magnesium silicate, synthetic aluminum silicate, magnesium oxide, and magnesium sulfate.

Examples of the hydrophobic lubricant include cacao butter, carnauba wax, glycerin fatty acid ester, hardened oil, white beeswax, soybean hardened oil, beeswax, cetanol, and sodium laurate.

Examples of the hydrophilic lubricant include sucrose fatty acid ester and polyethylene glycol (macrogol).

Two or more kinds of these lubricants may be mixed at an appropriate ratio and then used.

The lubricant in the formulation of the present invention is preferably magnesium stearate.

For example, the pharmaceutical composition of the present invention is preferably a pharmaceutical composition containing one or more selected from the group consisting of lactose, low-substituted hydroxypropylcellulose, hydroxypropylcellulose, and magnesium stearate.

A content of the excipient in the pharmaceutical composition of the present invention is not particularly limited, and is 10 to 90% by weight, preferably 25 to 75% by weight, and more preferably 45 to 65% by weight, based on the total amount of the pharmaceutical composition. When two or more kinds of excipients are used, a total amount of the excipients may be within the above content ranges.

A content of the binder in the pharmaceutical composition of the present invention is not particularly limited, and is 0.1 to 20% by weight, preferably 0.5 to 10% by weight, and more preferably 1 to 5% by weight, based on the total amount of the pharmaceutical composition. When two or more kinds of binders are used, a total amount of the binders may be within the above content ranges.

A content of the disintegrant in the pharmaceutical composition of the present invention is not particularly limited, and is 0.1 to 20% by weight, preferably 0.5 to 10% by weight, and more preferably 2 to 7% by weight, based on the total amount of the pharmaceutical composition. When two or more kinds of binders are used, a total amount of the binders may be within the above content ranges.

A content of the lubricant in the pharmaceutical composition of the present invention is not particularly limited, and is 0.05 to 10% by weight, preferably 0.1 to 7% by weight, and more preferably 0.2 to 3% by weight, based on the total amount of the pharmaceutical composition.

The pharmaceutical composition of the present invention may be a core tablet or an uncoated granule, or may be a film-coated tablet or a coated granule.

The film-coated tablet or the coated granule can be produced by producing a tablet or a granule according to the method for producing a pharmaceutical composition of the present invention, then coating the tablet or the granule with a light stabilizing substance and a polymer to form a coating layer. When forming a coating layer on the granule, a fluidized bed granulation coating machine, a fluidized bed tumbling coating machine, and the like can be used. When forming a coating layer on the tablet, a pan coating machine, an aerated coating machine, and the like can be used.

As a coating agent used in the present pharmaceutical composition, coating agents described in the Japanese Pharmacopoeia, the Japanese Pharmaceutical Codex, the Japanese Pharmaceutical Excipients, the Japan's Specifications and Standards for Food Additives, or the like can be used. Examples of the coating agent include a water-soluble coating agent, a sustained-release coating agent, an enteric coating agent, and a sugar coating base. These coating agents are coated on surfaces of a tablet, a granule, a capsule, and the like.

Examples of the water-soluble coating agent include cellulose-based polymers, acrylic acid-based polymers, vinyl-based polymers, and polysaccharides. Examples of the cellulose-based polymer include hydroxypropylcellulose (HPC), hypromellose (HPMC), methylcellulose, hydroxyethyl cellulose, and methyl hydroxyethyl cellulose. Examples of the acrylic-based polymer include aminoalkyl acrylate copolymer E and polyvinyl acetal diethyl aminoacetate. Examples of the vinyl-based polymer include polyvinyl pyrrolidone. Examples of the polysaccharide include pullulan, When a sustained-release formulation described in the Japanese Pharmacopoeia is produced, the formulation may be coated with a sustained-release coating agent. Examples of the sustained-release coating agent include cellulose-based polymers and acrylic acid-based polymers. Examples of the cellulose-based polymer include ethyl cellulose. Examples of the acrylic acid-based polymer include aminoalkyl methacrylate copolymer RS [Eudragit RS (trade name)] and ethyl acrylate-methyl methacrylate copolymer suspension [Eudragit NE (trade name)].

When an enteric formulation described in the Japanese Pharmacopoeia is produced, the formulation may be coated with an enteric coating agent. Examples of the enteric coating agent include cellulose-based polymers, acrylic acid-based polymers, and natural products. Examples of the cellulose-based polymer include hydroxypropyl methylcellulose phthalate, hydroxypropyl methylcellulose acetate succinate, hydroxyethyl cellulose, carboxymethyl ethyl cellulose, and cellulose acetate phthalate. Examples of the acrylic acid-based polymer include acrylic acid-based polymers such as methacrylic acid copolymer L [Eudragit L (trade name)], methacrylic acid copolymer LD [Eudragit L-30D55 (trade name)], and methacrylic acid copolymer S [Eudragit S (trade name)]. Examples of the natural product include shellac.

Examples of the sugar coating base include refined white soft sugar, and the sugar coating base is selected from talc, precipitated calcium carbonate, gelatin, gum arabic, pullulan, carnauba wax, and the like.

Two or more kinds of these coating agents may be mixed at an appropriate ratio and then used.

The coating agent in the pharmaceutical composition of the present invention is preferably hypromellose (HPMC).

A content of the coating agent in the pharmaceutical composition of the present invention is not particularly limited, and is 0.1 to 10% by weight, preferably 0.5 to 7% by weight, and more preferably 1 to 5% by weight, based on a total amount of the formulation. When two or more kinds of coating agents are used, a total amount of the coating agents may be within the above content ranges.

When a core tablet is film-coated, a film-coating layer is usually 1 to 10 parts by weight, preferably 2 to 6 parts by weight, per 100 parts by weight of the core tablet.

In the pharmaceutical composition of the present invention, a plasticizer may be contained together with a coating agent, and plasticizers described in the Japanese Pharmacopoeia, the Japanese Pharmaceutical Codex, the Japanese Pharmaceutical Excipients, the Japan's Specifications and Standards for Food Additives, or the like can be used. Examples of the plasticizer include a citric acid ester, a glycerin fatty acid ester, a surfactant, monostearate, diethyl phthalate, dibutyl phthalate, diethyl sebacate, and dibutyl sebacate.

Examples of the citric acid ester include triethyl citrate, tributyl citrate, and acetylated triethyl citrate.

Examples of the glycerin fatty acid ester include triacetin, polyethylene glycol, propylene glycol, glycerin, and monoacetylglycerin.

Examples of the surfactant include sorbitan monolaurate, poloxamer, polyoxyethylene-hydrogenated castor oil, and polysorbate.

Two or more kinds of these plasticizers may be mixed at an appropriate ratio and then used.

The plasticizer in the formulation of the present invention is preferably triethyl citrate.

A content of the plasticizer in the pharmaceutical composition of the present invention is not particularly limited, and is 0.01 to 5% by weight, preferably 0.05 to 1% by weight, based on the total amount of the formulation. When two or more kinds of plasticizers are used, a total amount of the plasticizers may be within the above content ranges.

In the pharmaceutical composition of the present invention, a coloring agent may be contained, and coloring agents described in the Japanese Pharmacopoeia, the Japanese Pharmaceutical Codex, the Japanese Pharmaceutical Excipients, the Japan's Specifications and Standards for Food Additives, or the like can be used. Examples of the coloring agent include natural dyes (natural colorants), synthetic dyes (synthetic colorants), iron oxide, titanium oxide, talc, riboflavin, light anhydrous silicic acid, and the like.

Examples of the natural dye (natural colorant) include caramel dye, turmeric extract, ß-carotene, carotene, licorice extract, and *Sasa veitchii* extract.

Examples of the synthetic dye (synthetic colorant) include Food Blue No. 1, Food Blue No. 2 aluminum lake, Food Yellow No. 4, Food Yellow No. 4 aluminum lake, Food Yellow No. 5, Food Red No. 2, Food Red No. 3, Food Red, and the like.

Examples of the iron oxide include yellow ferric oxide, ferric oxide, black oxide of iron, yellow oxide of iron, brown oxide of iron, and the like.

Two or more kinds of these coloring agents may be mixed at an appropriate ratio and then used.

Preferred are talc, yellow ferric oxide, and/or ferric oxide.

The pharmaceutical composition of the present invention contains the compound represented by Formula (I) or the like. The compound represented by Formula (I) or the like has a $P2X_3$ and/or $P2X_{2/3}$ receptor antagonistic action. Therefore, the pharmaceutical composition of the present invention is useful as a therapeutic agent for a disease involving $P_2X_3$ and/or $P2X_{2/3}$.

The $P2X_3$ and/or $P2X_{2/3}$ receptor is considered to be involved in pain, urological diseases and respiratory diseases, and the pharmaceutical composition of the present invention is useful as a pharmaceutical composition having an analgesic effect, a urinary tract disorder improving effect, a urination disorder improving effect, or a respiratory disorder improving effect. The pharmaceutical composition of the present invention is effective for treatment of these diseases, and alleviation or prevention of symptoms.

A weight of the compound represented by Formula (I) or the like, which is contained in the pharmaceutical composition of the present invention, particularly in the tablet or the granule, is not particularly limited as long as it is such a content that is easily taken by patients and enables the tablet or the granule to be produced, and is 1 to 450 mg, preferably 5 to 350 mg, and more preferably 10 to 300 mg, per tablet or pack.

Specifically, a content of the compound represented by Formula (I) or the like, which is contained per tablet or pack, is 10 mg, 20 mg, 30 mg, 50 mg, 70 mg, 100 gm, 150 gm, 200 mg, 250 mg, or 300 mg. In this case, 10 mg indicates a range of 9.0 to 11.0 mg, preferably a range of 9.5 to 10.5 mg, 20 mg indicates a range of 18.0 to 22.0 mg, preferably a range of 19.0 to 21.0 mg, 30 mg indicates a range of 26.0 to 34.0 mg, preferably a range of 28.0 to 32.0 mg, 50 mg indicates a range of 46.0 to 54.0 mg, preferably a range of 48.0 to 52.0 mg, 70 mg indicates a range of 66.0 to 74.0 mg, preferably a range of 68.0 to 72.0 mg, 100 mg indicates a range of 96.0 to 104.0 mg, preferably a range of 98.0 to 102.0 mg, 150 mg indicates a range of 146.0 to 154.0 mg, preferably a range of 148.0 to 152.0 mg, 200 mg indicates a range of 196.0 to 204.0 mg, preferably a range of 198.0 to 202.0 mg, 250 mg indicates a range of 246.0 to 254.0 mg, preferably a range of 248.0 to 252.0 mg, and 300 mg indicates a range of 296.0 to 804.0 mg, preferably a range of 298.0 to 302.0 mg.

The present invention also includes a method for analyzing a related substance in a crystal of a compound represented by Formula (I) or the like, or in a pharmaceutical composition containing the compound represented by Formula (I) or the like, the method including: a) a step of using a crystal of the compound represented by Formula (I) or the like, or a pharmaceutical composition containing the compound represented by Formula (I) or the like as a sample, and performing chromatographic analysis on the sample; and b) a step of obtaining a content or a content ratio of a compound represented by Formula (III) in the chromatographic analysis obtained in the above step.

The present, invention also includes a method for analyzing a content or a content ratio of a compound represented by Formula (III) in a crystal of a compound represented by Formula (I) or the like, or in a pharmaceutical composition containing the compound represented by Formula (I) or the like, wherein the compound represented by Formula (III) is used as a standard sample.

The chromatographic analysis may be a technique in which UV detection is combined (HPLC/UV) or a technique in which mass spectrometry is combined (LC/MS, L/MS/MS).

For example, an amount (content or content ratio) of a related substance including the compound represented by Formula (III) can be measured by high performance liquid chromatography. At that time, the compound represented by Formula (III) can be used as a standard sample (reference standard) in the measurement of the related substance. A content or a content ratio of the compound represented by Formula (III) can be calculated from a peak area of chromatography data. As the content ratio, a ratio with respect to an entire formulation, a ratio with respect to the compound represented by Formula (I) or the like, a ratio with respect to a total of the compound represented by Formula (I) or the like and the compound represented by Formula (III), or the like can be used.

The present invention also includes a dihydrate crystal of the compound represented by Formula (I).

X-ray powder diffraction peaks characteristic of the dihydrate crystal of the compound represented by Formula (I) are at X-ray powder diffraction angles (2θ): 5.7°, 7.7°. 11.8°, 15.2°, 17.7° 20.6°, 20.8°, 26.5°, 27.1°, or 29.1°, each also including a numerical value within a range of about ±0.2°.

For example, the dihydrate crystal of the compound represented by Formula (I) can be identified as a crystal that exhibits characteristic X-ray powder diffraction peaks at diffraction angles (2θ): 5.7±0.2°, 7.7±0.2°, 11.8±0.2°, 15.2±0.2°, 17.7±0.2°, 20.6±0.2°, 20.8±0.2°, 26.5±0.2°, 27.1±0.2°, and 29.1±0.2°.

The dihydrate crystal of the compound represented by Formula (I) can be identified as a crystal that exhibits characteristic X-ray powder diffraction peaks at diffraction angles (2θ): 5.7±0.2°, 7.7±0.2°, 11.8±0.2°, 15.2±0.2°, and 17.7±0.2°.

The dihydrate crystal of the present invention has a moisture content of, for example, 4.7 to 9.7% by weight. Preferably, the moisture content is about 5.6 to 7.6% by weight (a theoretical value of the moisture content of the dihydrate crystal of the compound represented by Formula (I) is 6.6%, but the moisture content may increase due to an influence of water adhering to the crystal, or a part of water in the crystal may be desorbed before measurement whereby the moisture content may decrease).

EXAMPLES

Hereinafter, the present invention will be described in more detail with reference to Examples and Reference Examples, but the present invention is not limited thereto. For numerical values (for example, amount, temperature, and the like), some error and deviation should be considered.

Unless otherwise noted, "%" means % by weight of the component and % by weight of the total weight of the composition, and "pressure" means a pressure at or near atmospheric pressure.

(Measurement of X-Ray Powder Diffraction Pattern)

X-ray powder diffraction measurement of a crystal obtained in each Example was performed according to the X-ray powder diffraction measurement method described in the General Tests. Processes and Apparatus of the Japanese Pharmacopoeia. The measurement conditions are shown below, (Apparatus)

SmartLab manufactured by Rigaku Corporation (Operation Method)

Measurement method: reflection method

Used wavelength: CuKα ray

Tube current: 200 mA

Tube voltage: 45 kV

Sample plate: glass

Incident angle of X-ray: 2.5°

Sampling width: 0.02°

Detector: HyPix-3000 (two-dimensional detection mode)

(Measurement of Raman Spectrum)

A Raman spectrum of a crystal obtained in each Example was measured. The measurement conditions are shown below.

Measuring instrument: LabRAM ARAMIS (manufactured by HORIBA Jobin Yvon SAS)

Measurement method: micro laser Raman spectroscopy

Laser wavelength: 633 nm (He—Ne laser)

Diffraction grating: 600 grooves/mm

Detector: CCD detector

Objective lens: 20×(NA 0.25)

Number of integrations: 5 times

Exposure time: 5 seconds (Measurement of TG/DTA)

About 4.4 mg of the crystal obtained in Reference Example K was weighed, was put in an aluminum pan, and was measured in an open system. The measurement conditions are as follows.

Apparatus: Hitachi High-Technologies TG/DTA STA7200RV

Measurement temperature range: room temperature to 300° C.

Heating rate: 10° C./min

The compound represented by Formula (I) or the like can be produced with reference to the method disclosed in Patent Document 1.

(Reference Example A) Synthesis of Compound (3)

[Chemical Formula 7]

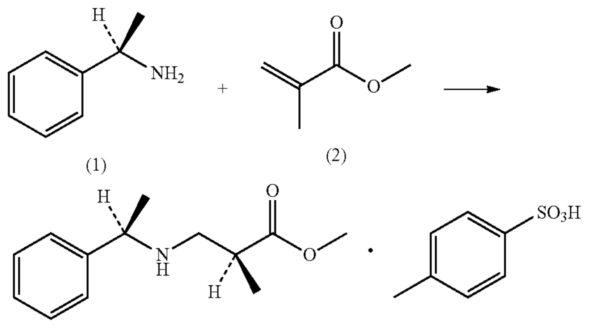

(1) (2) (3)

Methanol (20 mL) and methyl methacrylate (compound (2)) (49.64 g, 495.8 mmol) were added to (R-(+)-1-phenylethylamine (compound (1)) (20.01 g, 165.1 mmol) at room temperature. After cooling to −10° C., lithium chloride (7.07 g, 167 mmol) was added. The reaction solution was heated to 80° C. and stirred for 6 hours. The reaction solution was cooled to 25° C., a 9.1% sodium chloride aqueous solution (77.03 g) was added thereto, and an organic layer and an aqueous layer were obtained by liquid separation. Toluene (61.04 g) was added to the obtained aqueous layer at room temperature, and an aqueous layer was removed by liquid separation. The obtained two organic layers were combined, toluene (16.99 g) was added, and the mixture was distilled off under reduced pressure at 50° C.

p-Toluenesulfonic acid monohydrate (28.91 g, 152.0 mmol) was dissolved in ethanol (16.00 g) to prepare an ethanol solution (44.91 g) of p-toluenesulfonic acid.

Toluene (155.91 g) was added to the concentrated solution prepared above. A slurry obtained by adding toluene (63 μL) to the ethanol solution (5.88 g) of p-toluenesulfonic acid prepared above and a seed crystal (19.95 mg, 0.05070 mmol) of a compound (3) to suspend the seed crystal was added at room temperature. The ethanol solution (39.93 g) of the p-toluenesulfonic acid prepared above was added to the obtained slurry, and ethanol (10 mL) was added thereto. The resulting mixture was stirred for 2 hours and allowed to stand overnight. The mixture was cooled to 0° C. and stirred for 2 hours, and a solid was collected by filtration, to give the compound (3) (20.75 g, 31.9%) as a crude product.

Toluene (1.92 g), ethyl acetate (21.70 g) and methanol (2.90 g) were added to a part (5.00 g) of the crude product of the compound (3), and the mixture was stirred at 50° C. for 3 hours. The mixture was cooled to 0° C., and a solid was collected by filtration, whereby the compound (3) (1.65 g) was obtained.

Elemental analysis: C, 61.22%, H, 7.09%, N, 3.56%, S, 8.12%

$^1$H-NMR (DMSO-d6) δ ppm: 1.12 (d, J=7.0 Hz, 3H), 1.55 (br d, 1=6.7 Hz, 3H), 2.29 (s, 3H), 2.50 (s, 2H), 2.83 (br dd, J=13.2 Hz, 6.9 Hz, 1H), 2.90 (m, 2H), 3.62 (s, 3H), 7.13 (m, 2H), 7.47 (m, 7H)

(Reference Example B) Synthesis of Seed Crystal of Compound (3)

(R)-(+)-1-Phenylethylamine (compound (1)) (2.00 g, 16.5 mmol), methanol (1.59 g), methyl methacrylate (compound (2)) (4.97 g, 49.6 mmol), and lithium chloride (0.70 g, 17 mmol) were mixed at room temperature, and the mixture was heated to 80° C. and stirred for 4 hours. The reaction solution was cooled to 25° C., a 9.1% sodium chloride aqueous solution (7.70 g) was added thereto, and an aqueous layer was removed by liquid separation. After toluene (5.21 g) was added to the organic layer obtained, a methanol solution (4.46 g) of p-toluenesulfonic acid prepared by dissolving p-toluenesulfonic acid monohydrate (2.88 g, 15.1 mmol) in methanol (1.58 g) was added thereto. This reaction solution was added to toluene (6.94 g) cooled to 0° C., and the mixture was stirred at 0° C. for 30 minutes. The precipitated solid was collected by filtration to obtain a seed crystal (1.60 g, 24.6%) of the compound (3).

(Reference Example C) Synthesis of Compound (4)

[Chemical Formula 8]

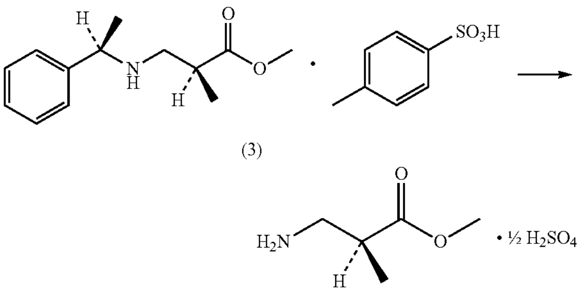

(3) (4)

Toluene (95.26 g) and water (44.00 g) were added to the compound (3) (22.00 g, 55.91 mmol) so that the compound (3) was suspended, an 8% sodium hydroxide aqueous solution (27.54 g) and water (4.40 g) were added thereto, and an aqueous layer was removed by liquid separation. Water (11.00 g) was added to the obtained organic layer, and an aqueous layer was removed by liquid separation. An operation of distilling off the resulting organic layer under reduced pressure at 50° C. and adding methanol was repeated so that the solvent was replaced with methanol. Concentrated sulfuric acid (2.04 g, 19.8 mmol), 10% palladium on carbon (2.20 g, about 40% wet) and methanol (17.41 g) were added to the obtained concentrated solution. The reaction solution was heated to 40° C. and stirred for 90 minutes under a hydrogen atmosphere. Palladium on carbon was removed by filtration, and methanol (52.24 g) and concentrated sulfuric acid (0.67 g, 6.5 mmol) were added to the obtained filtrate. An operation of adding acetonitrile to the obtained reaction solution and distilling off under reduced pressure was repeated so that the solvent was replaced with acetonitrile, and the reaction solution was cooled to 0° C. The precipitated solid was collected by filtration to obtain a compound (4) (8.58 g, 92.3%).

Elemental analysis: C, 35.72%, H, 7.18%, N, 8.55%, S, 9.63%

$^1$H-NMR (DMSO-d6) δ ppm: 1.10 (d, J=7.1 Hz, 3H), 2.62 (m, 1H), 2.75 (dd, J=12.7H, 5.9 Hz, 1H), 2.89 (dd, J=12.7 Hz, 7.3 Hz, 1H), 3.63 (s, 3H)

(Reference Example D) Synthesis of Compound (5)

[Chemical Formula 9]

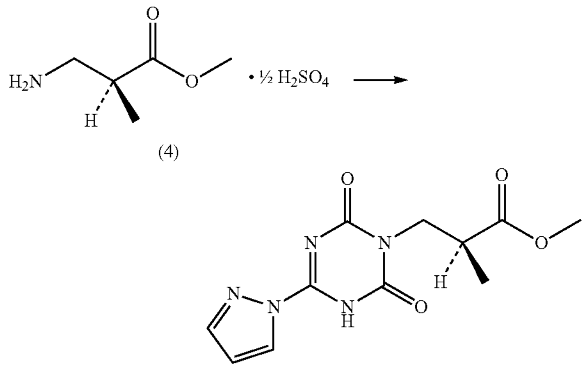

(4)

(5)

The compound (4) (19.00 g, 114.3 mmol) was suspended in acetonitrile (45.00 g). At 2° C., 1,8-diazabicyclo[5.4.0]-7-undecene (19.10 g, 125.5 mmol) and acetonitrile (3.00 g) were added thereto, and the mixture was stirred at 2° C. for 30 minutes. The reaction solution was added, at 2° C., to a slurry obtained by suspending N,N-carbonyldiimidazole (21.30 g, 131.4 mmol) in acetonitrile (75.00 g). Acetonitrile (15.00 g) was added to the reaction solution, and the mixture was stirred at 2° C. for 1 hour and 22 minutes. At 2° C., 1,8-diazabicyclo[5.4.0]-7-undecene (17.40 g, 114.3 mmol) and acetonitrile (3.00 g) were added to the reaction solution, and the mixture was cooled to 1° C. To the reaction solution, 1H-pyrazole-1-carboxamidine hydrochloride (106.80 g, 114.6 mmol) and acetonitrile (3.00 g) were added. The reaction solution was heated to 60° C. and stirred for 2 hours and 10 minutes. The reaction solution was cooled to 20° C. At 2° C., 1.8-diazabicyclo[5.4.0]-7-undecene (27.80 g, 182.6 mmol) and acetonitrile (3.00 g) were added to the reaction solution, and the mixture was cooled to −10° C. To the reaction solution, N,N-carbonyldiimidazole (29.70 g, 183.2 mmol) and acetonitrile (3.00 g) were added. The reaction solution was stirred at 2° C. for 1 hour and 20 minutes. To the reaction solution, methanol (7.50 g), acetic acid (4.80 g, 79.9 mmol), and acetonitrile (3.00 g) were added at 2° C. The reaction solution was distilled off under reduced pressure at 50° C. N,N-Dimethylacetamide (27.00 g) was added to the obtained concentrated solution, the mixture was cooled to 10° C., and 17% aqueous sulfuric acid (204.1 g) and water (19.00 g) were added thereto. To the reaction solution, 17% aqueous sulfuric acid (31.30 g) and water (2.50 g) were added at 25° C., and the mixture was stirred for 1 hour and 48 minutes. The reaction solution was distilled off under reduced pressure at 50° C. Water (190 mL) was added to the obtained concentrated solution and cooled to 2° C., and then 17% aqueous sulfuric acid (3.30 g) and water (1.30 g) were added thereto. The reaction solution was stirred at 2° C. for 1 hour and 15 minutes, and the precipitated solid was collected by filtration to obtain a compound (5) (27.13 g, 85.0%).

$^1$H-NMR ($CDCl_3$) δ ppm: 1.24 (d. J=7.1 Hz, 3H), 3.02 (m, 1H), 3.68 (s, 3H), 1.02 (dd, J=13.4 Hz, 6.3 Hz, 1H), 4.24 (dd, J=13.3 Hz, 8.4 Hz, 1H), 6.60 (dd, J=2.8 Hz, 1.6 Hz, 1H), 7.85 (d, J=1.6 Hz, 1H), 8.48 (dd, J=2.9 Hz, 0.6 Hz, 1H), 9.70 (brs, 1H)

(Reference Example E) Synthesis of Compound (8)

[Chemical Formula 10]

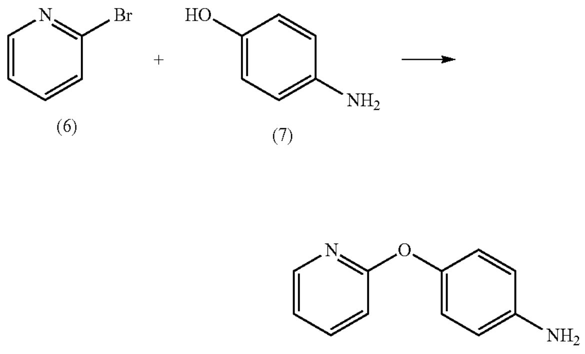

(6) (7)

(8)

Sodium tert-butoxide (12.50 g, 130.1 mol) was suspended in N-methyl-2-pyrrolidone (64.00 g), and 4-aminophenol (compound (7)) (14.10 g, 129.2 mmol) and N-methyl-2-pyrrolidone (16.00 g) were added thereto. The reaction solution was heated to 100° C., and 2-bromopyridine (compound (6)) (19.50 g, 123.4 mmol) and N-methyl-2-pyrrolidone (4.00 g) were added thereto. The reaction solution was stirred at 115° C. for 8 hours and 20 minutes, and was cooled to 50° C. Water (29.00 g) was added to the reaction solution at 50° C., the reaction solution was cooled to 25° C., and water (107.00 g) was added thereto. A seed crystal (8, 20 mg) of a compound (8) and water (195 mg) were added to the reaction solution, and the mixture was stirred at 20° C. for 50 minutes. Water (156.00 g) was added to the reaction solution at 25° C., the reaction solution was cooled to 5° C., and was stirred for 1 hour and 30 minutes. The precipitated solid was collected by filtration to obtain the compound (8) (17.81 g, 77.5%).

$^1$H-NMR ($CDCl_3$) δ ppm: 3.60 (s, 2H), 6.69-6.73 (m, 2H) 6.83 (ddd, J=8.4 Hz, 0.8 Hz, 0.8 Hz, 1H), 6.92-6.96 (m, 3H), 7.63 (ddd, J=8.0 Hz, 7.2 Hz, 2.0 Hz, 1H), 8.18 (ddd, J=5.2 Hz, 2.0 Hz, 0.8 Hz, 1H)

(Reference Example F) Synthesis of Seed Crystal of Compound (8)

Sodium tert-butoxide (3.20 g, 33.3 mmol) was suspended in N-methyl-2-pyrrolidone (16.42 g), and 4-aminophenol (compound (7)) (3.64 g, 33.4 mmol) and N-methyl-2-pyrrolidone (4.12 g) were added thereto. The reaction solution was heated to 100° C., and 2-bromopyridine (compound (6)) (5.01 g, 31.7 mmol) and N-methyl-2-pyrrolidone (1.10 g) were added thereto. The reaction solution was stirred at 115° C. for 6 hours, and sodium tert-butoxide (1.07 g, 11.1 mmol) was added thereto. The mixture was stirred at 115° C. for 2 hours and 35 minutes, and then cooled to 50° C. Water (7.50 g) was added to the reaction solution at 50° C., and thereafter the reaction solution was cooled to 25° C. Water (67.54 g) was added thereto, and was cooled to 1° C. for crystallization. After the obtained slurry was stirred at 5° C. for 30 minutes, the precipitated solid was collected by filtration to obtain a seed crystal (3.84 g, 65.2%) of the compound (8).

(Reference Example G) Synthesis of Compound (9)

[Chemical Formula 11]

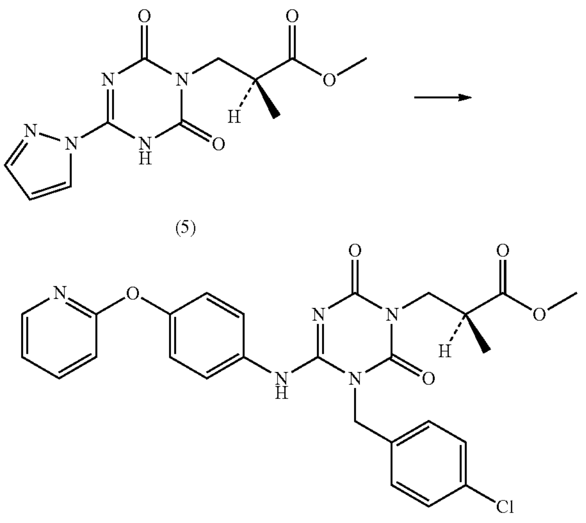

(5)

(9)

Sodium bromide (4.1 g, 39.9 mmol) and N,N-dimethylacetamide (27.70 g) were added to the compound (5) (10.13 g, 36.27 mmol). N,N-diisopropylethylamine (5.16 g, 39.9 mmol) and N,N-dimethylacetamide (0.96 g) were added to the reaction solution, and the mixture was heated to 75° C. To the reaction solution, an N,N-dimethylacetamide solution of 4-chlorobenzyl chloride prepared by dissolving 4-chlorobenzyl chloride (6.43 g, 39.9 mmol) in N,N-dimethylacetamide (9.56 g) was added at 75° C. and N,N-dimethylacetamide (9.56 g) was added. The reaction solution was stirred at 75° C. for 5 hours and 15 minutes. The reaction solution was cooled to 25° C., acetic acid (0.65 g, 11 mmol) was added thereto, and the mixture was heated to 40° C. To the reaction solution, an N,N-dimethylacetamide solution of the compound (8) prepared by dissolving the compound (8) (7.43 g, 39.9 mmol) in N,N-dimethylacetamide (9.55 g) was added, and N,N-dimethylacetamide (9.55 g) was added. The reaction solution was stirred at 40° C. for 3 hours, and was cooled to room temperature. To the reaction solution, acetone (27.91 g) and water (35.46 g) were added. A seed crystal (10.13 mg) of a compound (9), water (0.40 g), and acetone (0.08 g) were added to the reaction solution, and the mixture was stirred at room temperature for 3 hours and 25 minutes and then allowed to stand overnight. After the reaction solution was stirred at room temperature for 1 hour, then water (30.39 g) was added thereto, and the mixture was stirred for 3 hours and 25 minutes. The precipitated solid was collected by filtration to obtain the compound (9) (16.72 g, 88.3%).

$^1$H-NMR ($CDCl_3$) δ ppm: 1.19 (d, J=7.1 Hz, 3H), 2.91 (m, 1H), 3.61 (s, 3H), 3.90 (dd, J=13.6 Hz, 6.2 Hz, 1H), 4.12 (dd, =13.6 Hz, 8.4 Hz, 1H), 5.18 (d, J=14.2 Hz, 1H), 5.22 (d, J=14.2 Hz, 1H), 6.85 (m, 2H), 6.96 (m, 1H), 7.00 (m, 1H), 7.11 (m, 2H), 7.31 (m, 2H), 7.50 (m, 2H), 7.70 (m, 1H), 7.89 (brs, 1H), 8.14 (m, 1H)

(Reference Example H) Synthesis of Seed Crystal of Compound (9)

Sodium bromide (2.00 g, 19.4 mmol) and N,N-dimethylacetamide (13.67 g) were added to the compound (5) (5.01 g, 17.9 mmol). N,N-diisopropylethylamine (2.55 g, 19.7 mmol) and N,N-dimethylacetamide (0.47 g) were added to the reaction solution, and the mixture was heated to 75° C. To the reaction solution, an N,N-dimethylacetamide solution of 4-chlorobenzyl chloride prepared by dissolving 4-chlorobenzyl chloride (3.16 g, 19.6 mmol) in N,N-dimethylacetamide (4.71 g) was added at 75° C., and N,N-dimethylacetamide (4.71 g) was added. The reaction solution was stirred at 75° C. for 4 hours and 30 minutes. The reaction solution was cooled to 25° C., acetic acid (0.32 g, 5.3 mmol) was added thereto, and the mixture was heated to 40° C. To the reaction solution, an N,N-dimethylacetamide solution of the compound (8) prepared by dissolving the compound (8) (3.66 g, 19.7 mmol) in N,N-dimethylacetamide (4.71 g) was added, and N,N-dimethylacetamide (4.71 g) was added. The reaction solution was stirred at 40° C. for 3 hours and 25 minutes, and was cooled to room temperature. To the reaction solution, acetone (13.79 g) and water (17.54 g) were added. The reaction solution was allowed to stand overnight at room temperature. After the reaction solution was heated to 25° C. and stirred for 5 hours, then water (15.00 g) was added thereto, and the mixture was stirred at 25° C. for 2 hours. The precipitated solid was collected by filtration to obtain a seed crystal of the compound (9) (8.17 g, 87.2%).

(Reference Example 1) Synthesis of Anhydrate Crystal of Compound Represented by Formula (I)

[Chemical Formula 12]

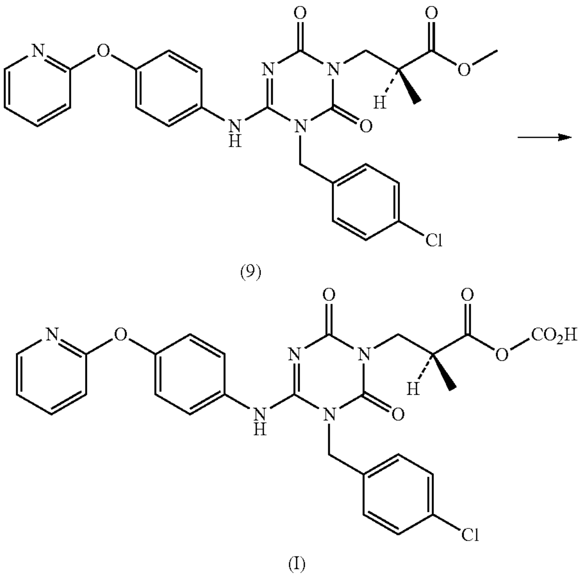

(9)

(I)

To the compound (9) (70.00 g, 134.1 mmol), 2-propanol (109.91 g), water (63.00 g), and a 48% sodium hydroxide aqueous solution (27.94 g, 335.3 mmol) were added. The reaction solution was heated to 35° C. and stirred for 4 hours and 10 minutes. To the reaction solution, 2-propanol (32.97 g), methanol (177.30 g), and water (63.00 g) were added, and the mixture was heated to 50° C. Formic acid (18.52 g, 402.3 mmol) and a seed crystal of an anhydrate of the compound represented by Formula (I) (70.00 mg) were added to the reaction solution, and the mixture was stirred at 50° C. for 1 hour and 10 minutes. Thereafter, water (280.00 g) was added thereto, and the mixture was cooled to 25° C.

The precipitated solid was collected by filtration to obtain an anhydrate crystal of the compound represented by Formula (I) (62.86 g, 92.3%).

The anhydrate crystal was confirmed by differential scanning calorimetry (DSC), thermogravimetry/differential thermal analysis (TG/DTA), moisture adsorption/desorption measurement (DVS), and X-ray powder diffraction measurement.

$^1$H-NMR ($CDCl_3$) δ ppm: 1.13 (d, J=7.0 Hz, 3H), 2.76 (in, 1H), 3.83 (dd, J=13.5 Hz, 6.1 Hz, 1H), 4.03 (dd, J=13.5 Hz, 8.5 Hz, 1H), 5.14 (m, 1H), 5.25 (d, J=14.4 Hz, 1H), 6.82 (d, J=8.6 Hz, 2H), 7.00 (m, 2H), 7.08 (m, 2H), 7.25 (m, 2H), 7.43 (d, J=8.3 Hz, 2H), 7.72 (m, 1H), 8.06 (dd, J=5.4 Hz, 1.8 Hz, 1H), 8.67 (brs, 1H)

Figure 1:
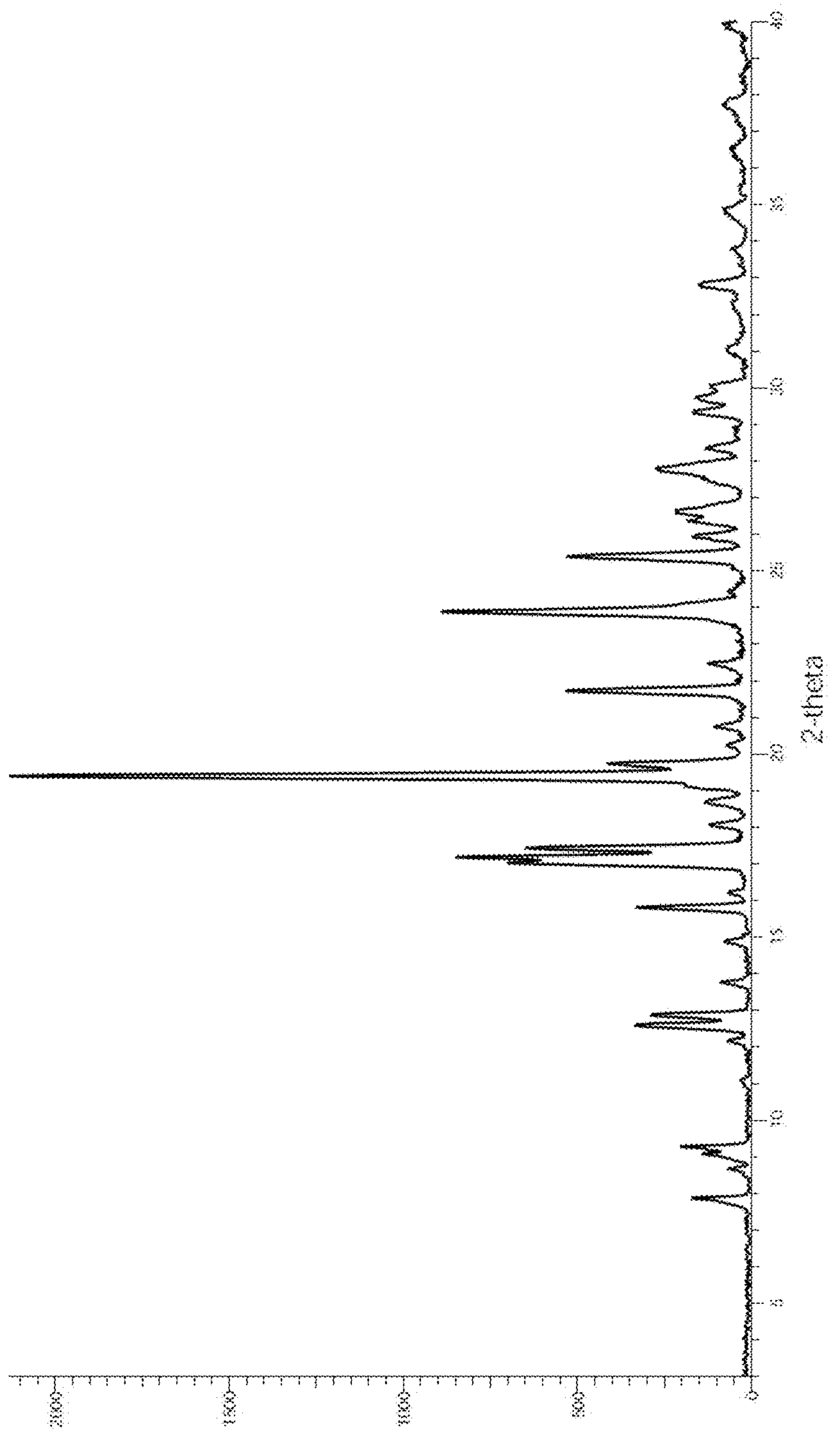
FIG. 1 shows an X-ray powder diffraction pattern of an anhydrate crystal of a compound represented by Formula (I). The horizontal axis represents 2θ (°), and the vertical axis represents an intensity (Count).

An X-ray powder diffraction pattern of the crystal of the anhydrate of the compound represented by Formula (I) is shown in FIG. 1.

Diffraction angles (2θ): 7.9°, 9.3°, 12.6°, 12.9°, 15.8°, 17.2°, 19.4°, 21.7°, 23.9°, 25.4°, 26.6°, 27.8°, 32.8°.

Figure 2:
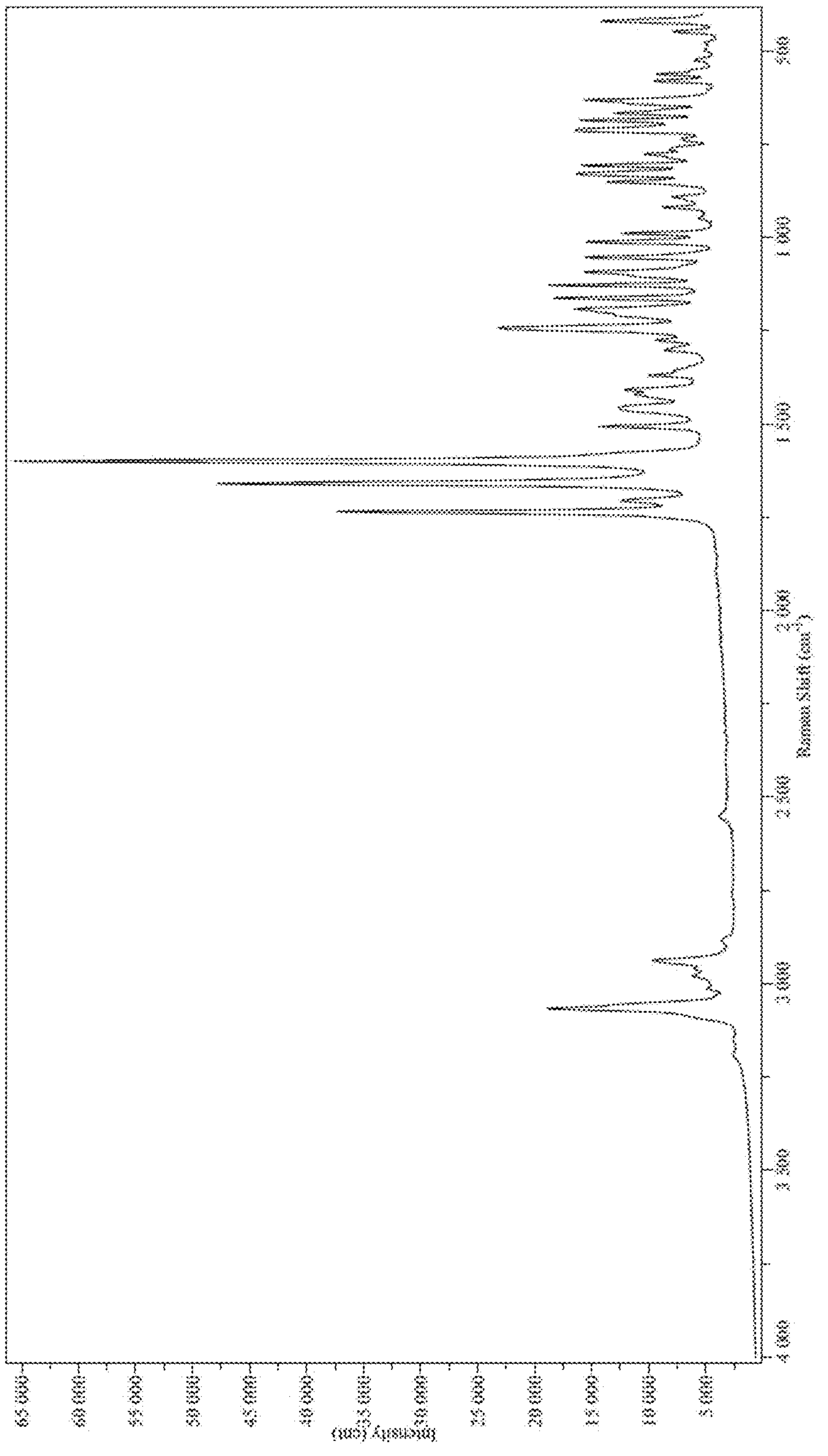
FIG. 2 shows a Raman spectrum of the anhydrate crystal of the compound represented by Formula (I). The horizontal axis represents a Raman shift ($cm^{-1}$), and the vertical axis represents a peak intensity.

A Raman spectrum of the crystal of the anhydrate of the compound represented by Formula (I) is shown in FIG. 2.

Main absorption peaks were recognized at 829 $cm^{-1}$±2 $cm^{-1}$, 989 $cm^{-1}$±2 $cm^{-1}$, 1013 $cm^{-1}$±2 $cm^{-1}$, 1093 $cm^{-1}$±2 $cm^{-1}$, 1128 $cm^{-1}$±2 $cm^{-1}$, 1213 $cm^{-1}$±2 $cm^{-1}$, 1370 $cm^{-1}$±2 $cm^{-1}$, 1599 $cm^{-1}$±2 $cm^{-1}$, 1659 $cm^{-1}$±2 $cm^{-1}$, 1735 $cm^{-1}$±2 $cm^{-1}$, 2938 $cm^{-1}$±2 $cm^{-1}$, and 3067 $cm^{-1}$±2 $cm^{-1}$.

Melting point (onset temperature): about 196° C.

(Reference Example J) Synthesis of Seed Crystal of Anhydrate of Compound Represented by Formula (I)

To the compound (9) (1.50 g, 2.87 mmol), methanol (5.95 g), water (3.00 g), and a 48% sodium hydroxide aqueous solution (0.60 g, 7.20 mmol) were added. The reaction solution was heated to 40° C. and stirred for 1 hour and 30 minutes. The reaction solution was cooled to room temperature, formic acid (0.10 g, 8.62 mmol), ethyl acetate (10.5 mL), and water (9 mL) were added thereto at room temperature, and an aqueous layer was removed by liquid separation. Water (3 mL) was added to the obtained organic layer, an aqueous layer was removed by liquid separation, 2-propanol (90 mL) was added to the organic layer, and the mixture was distilled off under reduced pressure at 40° C. Water (7.5 mL) and 2-propanol (7.5 mL) were added to the obtained concentrated residue, and the mixture was stirred at 25° C. for 1 hour and 30 minutes. Water (7.5 mL) and methanol (7.5 mL) were added, then the mixture was heated to 60° C. and stirred for 2 hours, and cooled to 25° C. The precipitated solid was collected by filtration to obtain a seed crystal (1.25 g, 85.6%) of an anhydrate of the compound represented by Formula (I).

(Reference Example K) Synthesis of Dihydrate Crystal of Compound Represented by Formula (I)

To an anhydrate crystal (50.00 g, 98.43 mmol) of the compound represented by Formula (I), 2-propanol (314.02 g), water (150.00 g), and 48% sodium hydroxide (20.51 g, 246.1 mmol) were added to dissolve the anhydrate crystal. To the resulting solution, 35% hydrochloric acid (25.64 g, 246.1 mmol) and a seed crystal of a dihydrate of the compound represented by Formula (I) (50.00 mg) were added, then the mixture was stirred at room temperature for 1 hour, and water (250.00 g) was added and stirred for 2 hours. The obtained slurry was cooled to 5° C. and filtered to obtain a dihydrate crystal (49.23 g) of the compound represented by Formula (I). The dihydrate crystal was confirmed by thermogravimetry/differential thermal analysis (TG/DTA), moisture adsorption/desorption measurement (DVS), and X-ray powder diffraction measurement.

Figure 3:
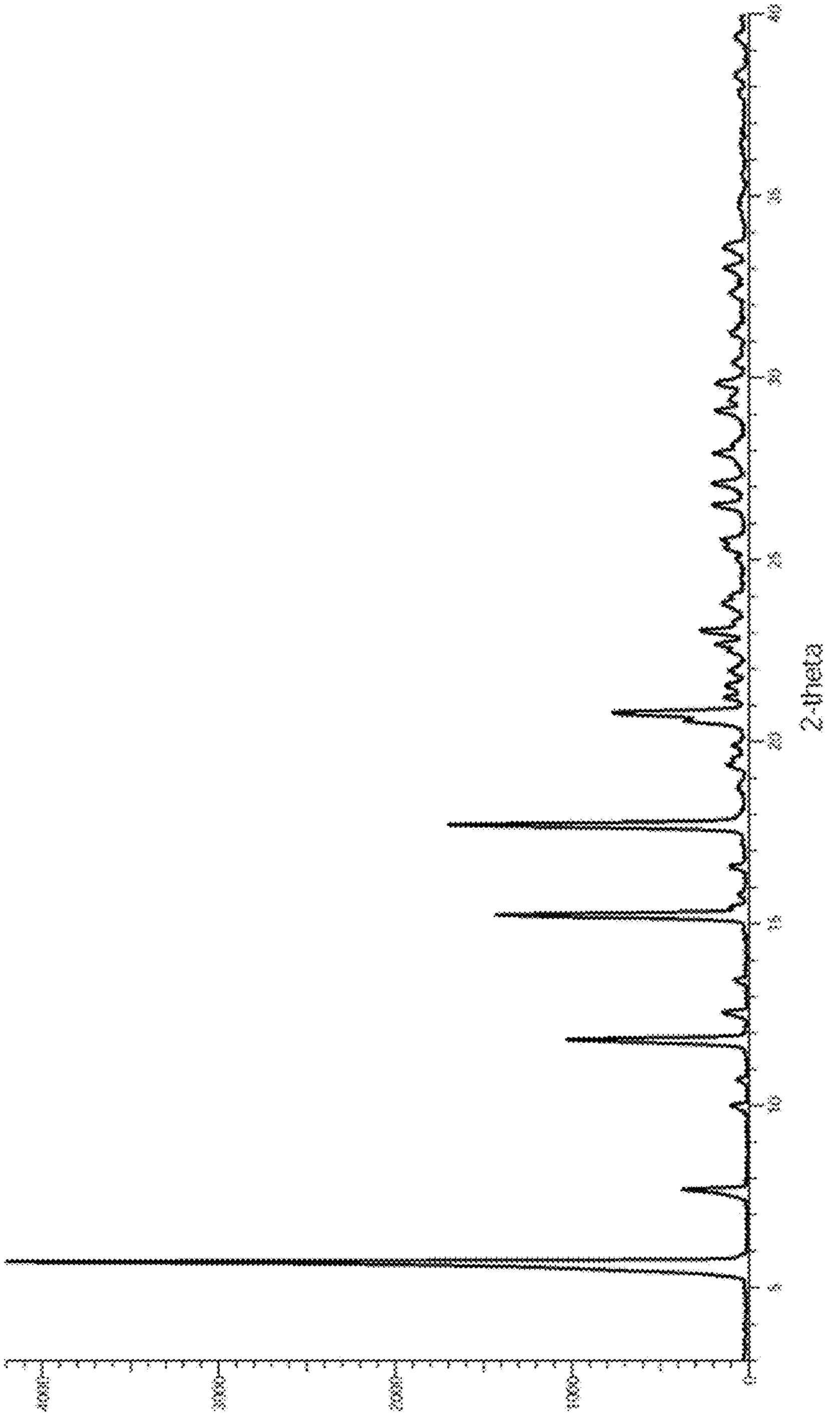
FIG. 3 shows an X-ray powder diffraction pattern of a dihydrate crystal of the compound represented by Formula (I). The horizontal axis represents 2θ (°), and the vertical axis represents an intensity (Count).

An X-ray powder diffraction pattern of the dihydrate crystal of the compound represented by Formula (I) is shown in FIG. 3.

Diffraction angles (2θ): 5.7°, 7.7°, 11.8°, 15.2°, 17.7°, 20.6°, 20.8°, 26.5°, 27.1°, 29.1°.

Figure 4:
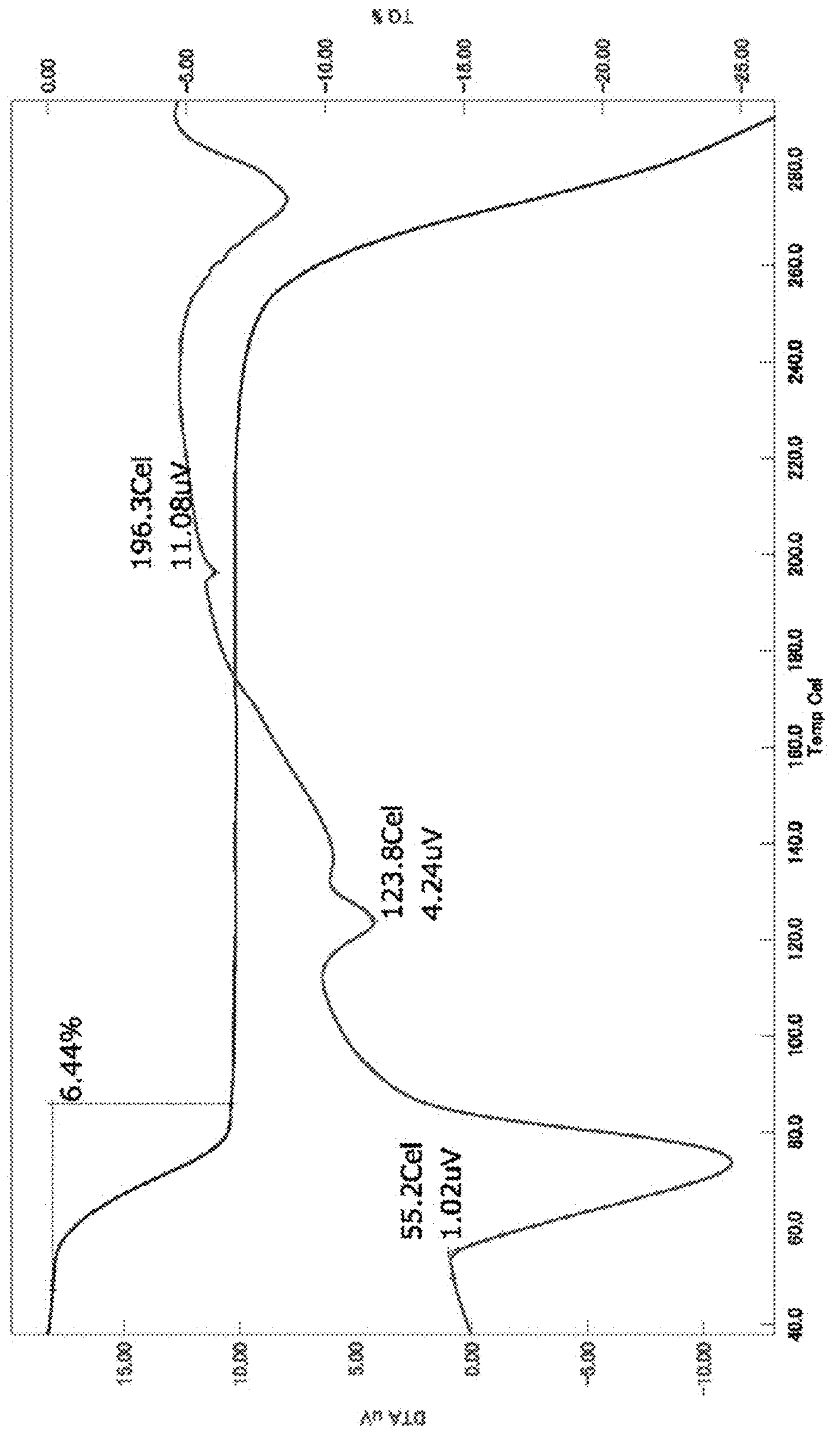
FIG. 4 shows TG/DTA analysis results of the dihydrate crystal of the compound represented by Formula (I). The vertical axis represents a heat flow (μV) or a weight change (%), and the horizontal axis represents temperature CC). “Cel” in the figure means a degree Celsius (° C.).

The results of the thermogravimetry/differential thermal analysis (TG/DTA) of the dihydrate crystal of the compound represented by Formula (I) are shown in FIG. 4. As a result, from about 55° C. to about 85° C., a weight loss of 6.4% with an endothermic peak was confirmed. Since a theoretical value of a moisture content of the dihydrate crystal of the compound represented by Formula (I) was 6.6%, it was confirmed to be a dihydrate crystal of the compound represented by Formula (I).

(Example L) Synthesis of Seed Crystal of Dihydrate of Compound Represented by Formula (I)

To the compound (9) (70.00 g, 134.1 mmol), 2-propanol (109.91 g), water (63.02 g), and 48% sodium hydroxide (27.95 g, 335.4 mmol) were added, and the mixture was stirred at 25° C. for 4 hours. To the obtained reaction solution, 2-propanol (16.49 g), methanol (127.43 g), and water (217.00 g) were added, then formic acid (9.88 g, 215 mmol) was added thereto at 25° C., and the mixture was stirred at 25° C. for 35 minutes. To the obtained slurry, a formic acid aqueous solution prepared by mixing formic acid (8.64 g, 188 mmol) and water (70.00 g) was added dropwise at 25° C., and then water (7.00 g) and methanol (27.70 g) were added thereto. The obtained slurry was filtered to obtain a dihydrate of the compound represented by Formula (I) (64.01 g, content ratio of the compound represented by Formula (III): not detected).

The content ratio of the compound represented by Formula (III) in the dihydrate crystal of the compound represented by Formula (I) produced in Example L was determined by the following method.

In Examples 1 to 4 and 6 and Reference Examples 1 to 2, the content ratio was determined in the same manner.

(Test Example 1) Measurement of Content Ratio of Compound Represented by Formula (III) Contained in Crystal (Preparation of Standard Solution)

A standard sample of the compound represented by Formula (III) was prepared by the following method, Step 1: About 25 mug of the compound represented by Formula (III) was weighed precisely, and dissolved in a mixed solution of N,N-dimethylformamide and water (9:1) to make exactly 20 mL, Step 2: One milliliter of the solution of Step 1 was accurately taken, and a mixed solution of N,N-dimethylformamide and water (9:1) was added to make exactly 50 mL.

Step 3: Two milliliters of the solution of Step 2 was accurately taken, and a mixed solution of N,N-dimethylformamide and water (9:1) was added to make exactly 20 mL, thereby obtaining a standard solution.

(Preparation of Sample Solution)

A sample solution was prepared by the following method.

About 125 to 600 mg of a sample was weighed precisely, and dissolved by adding a mixed solution of N,N-dimethylformamide and water (9:1) to make exactly 5 mL.

(Method for Measuring Amount of Compound Represented by Formula (III))

An amount of the compound represented by Formula (III) was measured with a liquid chromatograph according to the following method and conditions.

Measuring instrument: UHPLC (NexeraX2, SHIMADZU)
Detector: UV
Measurement wavelength: 271 nm
Column: ACQUITY UPLC BEH SHIELD PR18, 1.7 μm (2.1×100 mm)
Column temperature: constant temperature at near 40° C.
Mobile phase A: 20 mmol/L potassium dihydrogen phosphate aqueous solution
Mobile phase B: acetonitrile for liquid chromatography
Feed of mobile phase: The mixing ratio of mobile phase A and mobile phase B was changed as shown in Table 1 to control concentration gradient.

TABLE 1

| Time (min) after sample injection | Composition of liquid A (%) | Composition of liquid B (%) |
|---|---|---|
| 0.00 to 7.00 | 80 → 65 | 20 → 35 |
| 7.00 to 10.00 | 65 | 35 |
| 10.00 to 10.01 | 65 → 30 | 35 → 70 |
| 10.01 to 20.00 | 30 | 70 |
| 20.00 to 20.01 | 30 → 80 | 70 → 20 |
| 20.01 to 30.00 | 80 | 20 |

Flow rate: 0.3 mL/min
Injection amount 2 μL
Sample cooler temperature: 5° C.
Area measurement range: 11 minutes after injection
Needle washing solution: mixed solution of N,N-dimethylformamide and water (9:1)

(Calculation Formula)

Content (ppm) of compound represented by Formula (III)=$M_S/M_T \times A_T/A_S \times 1/2000 \times 1000000$ (Mathematical formula 4)

$M_S$: Weighing amount (mg) of compound represented by Formula (III)
$M_T$: Weighing amount (mg) of sample
$A_S$: Peak area of compound represented by Formula (III) obtained from standard solution
$A_T$: Peak area of compound represented by Formula (III) obtained from sample solution
1/2000: Dilution ratio As a result of the above test, it was found that in a dihydrate crystal of the compound represented by Formula (I), the compound represented by Formula (III) is not contained or is below a detection limit.

A method for producing a dry-pulverized product of the compound represented by Formula (I) or the like is shown below.

(Reference Example 1) Production of Dry-Pulverized Product of Compound Represented by Formula (I)

An anhydrate crystal of the compound represented by Formula (I) obtained in accordance with Reference Example I mentioned above was dry-pulverized in a counter jet mill (100AFG, Hosokawa Micron Corporation) to obtain a product (14.53 μm).

A 90% particle size distribution in the production method of Reference Example 1 was determined by the following method.

In Examples 1 to 6 and Reference Example 3, the 90% particle size distribution was determined in the same manner.

(Test Example 2) Method for Measuring 90% Particle Size Distribution

A 90% particle size distribution was measured according to the following method and conditions.

Measuring instrument: laser diffraction particle size distribution measuring apparatus (HELOS & RODOS, Sympatec GmbH)
Dispersion pressure: 4 bar
Feed: 50%
Rotation: 20%
Focal length: 50 mm
Trigger condition: reference duration 2 seconds
Time Base 100 ms
Start Optical concentration ≥1.0%
Stop Optical concentration ≤1.0%
Measurement range: R2

A method for producing a crystal of the compound represented by Formula (I) or the like, characterized by wet-pulverizing the compound represented by Formula (I) or the like, is shown below.

Examples 1 to 4 show a method for producing a crystal of the compound represented by Formula (I) or the like including a wet pulverization step using a pressure type homogenizer.

(Example 1) Production of Wet-Pulverized Product of Compound Represented by Formula (I) (1)

To the compound (9) (70.00 g, 134.12 mmol), 2-propanol (109.91 g), water (63.00 g), and 48% sodium hydroxide (27.94 g, 335.3 mmol) were added, and the mixture was stirred at 35° C. for 2 hours. 2-Propanol (32.97 g) water (63.00 g), and methanol (177.30 g) were added to the reaction solution (content ratio of the compound represented by Formula (III): 54.3 ppm), and the temperature was raised to 50° C. Formic acid (18.52 g, 402.35 mmol) and a seed crystal (70.02 mg) of an anhydrate of the compound represented by Formula (I) were added while performing a pressure type homogenizer (LAB2000, SMT) treatment, and then the mixture was stirred for 1 hour under a pressure type homogenizer treatment to precipitate an anhydrate crystal of the compound represented by Formula (I), thereby obtaining a slurry.

Water (280.00 g) was added to the obtained slurry under a pressure type homogenizer treatment, and the slurry was cooled to 25° C. The obtained slurry was wet-pulverized with a pressure type homogenizer and then filtered to obtain an anhydrate crystal (62.86 g, 90% particle size distribution: 5.51 μm, content ratio of the compound represented by Formula (III): 1.10 ppm) of the compound represented by Formula (I).

A total amount of the content ratio of the compound represented by Formula (III) contained in the filtrate after filtration and the obtained crystal was 119.6 ppm, and an increased amount of the content ratio of the compound represented by Formula (III) during the crystallization operation was 119.6−54.3=65.3 ppm.

The content ratio of the compound represented by Formula (JII) in the solution in the production method of Example 1 was determined by the following method.

In Example 4 and Reference Examples 2 to 3, the content ratio was determined in the same manner.

(Test Example 3) Measurement of Content Ratio of Compound Represented by Formula (III) Contained in Solution (Preparation of Standard Solution)

A standard sample of the compound represented by Formula (III) was prepared by the following method.

Step 1: About 25 mg of the compound represented by Formula (III) was weighed precisely, and dissolved in a mixed solution of N,N-dimethylformamide and water (9:1) to make exactly 20 mL.

Step 2: One milliliter of the solution of Step 1 was accurately taken, and a mixed solution of N,N-dimethylformamide and water (9:1) was added to make exactly 50 mL.

Step 3: Two milliliters of the solution of Step 2 was accurately taken, and a mixed solution of N,N-dimethylformamide and water (9:1) was added to make exactly 20 ml, thereby obtaining a standard solution.

(Preparation of Sample Solution)

A sample solution was prepared by the following method.

About 60 to 1300 mg of a sample was weighed precisely, and dissolved by adding a mixed solution of N,N-dimethylformamide and water (9:1) to make exactly 5 mL.

(Method for Measuring Amount of Compound Represented by Formula (III))

An amount of the compound represented by Formula (III) was measured with a liquid chromatograph according to the following method and conditions.

Measuring instrument: UHPLC (NexeraX2, SHIMADZU)

Detector: UV

Measurement wavelength: 271 nm

Column: ACQUITY UPLC BEH SHIELD PF18, 1.7 μm (2.1×100 mm)

Column temperature: constant temperature at near 40° C.

Mobile phase A: 20 mmol/L potassium dihydrogen phosphate aqueous solution

Mobile phase B: acetonitrile for liquid chromatography

Feed of mobile phase: The mixing ratio of mobile phase A and mobile phase B was changed as shown in Table 2 to control concentration gradient.

TABLE 2

| Time (min) after sample injection | Composition of liquid A (%) | Composition of liquid B (%) |
|---|---|---|
| 0.00 to 7.00 | 80 → 65 | 20 → 35 |
| 7.00 to 10.00 | 65 | 35 |
| 10.00 to 10.01 | 65 → 30 | 35 → 70 |
| 10.01 to 20.00 | 30 | 70 |
| 20.00 to 20.01 | 30 → 80 | 70 → 20 |
| 20.01 to 30.00 | 80 | 20 |

Flow rate: 0.3 mL/min

Injection amount: 2 μL

Sample cooler temperature: 5° C.

Area measurement range: 11 minutes after injection

Needle washing solution: mixed solution of N,N-dimethylformamide and water (9:1)

(Calculation formula)

$$\text{Content (ppm) of compound represented by Formula (III)}=M_S/M_T\times A_T/A_S\times 1/2000\times Y_T/Y_S\times 1000000 \quad \text{(Mathematical formula 3)}$$

$M_S$: Weighing amount (mg) of compound represented by Formula (III)

$M_T$: Weighing amount (mag) of sample $A_S$: Peak area of compound represented by Formula (III) obtained from standard solution $A_T$: Peak area of compound represented by Formula (III) obtained from sample solution $Y_S$: Yield (g) of compound represented by Formula (I)

$Y_T$: Total weight (g) of sample

1/2000: Dilution ratio (Test Example 4) Stability Testing

The samples obtained in Example 1 and Reference Example 1 were subjected to a stability testing to evaluate the content of the compound represented by Formula (III).

The storage conditions and the packaging form of Example 1 are shown in Table 3, and the storage conditions and the packaging form of Reference Example 1 are shown in Table 4.

In the tables, the details of the packaging form are as follows, and the same applies to other tables.

Double polyethylene bag, Convex, metal can:

Samples were placed in a polyethylene bag (Suntec-LD M2206 (additive free) 100×210×0.1 mm, TOWA KAKO CO., LTD.) and tightened with Convex (CV100N, SHIBAKEISOZAI CO., LTD.). This bag was further placed in a polyethylene (Suntec-LD M2206 (additive free) 100×210×0.1 mm, TOWA KAKO CO., LTD.) bag and similarly tightened with Convex (CV100N, SHIBAKEISOZAI CO., LTD.). The above samples under the same storage conditions were put together in a metal can (3dia, a stainless steel can with an inner diameter of 16 cm and a depth of 18 cm).

Double polyethylene bag, Convex (containing desiccant), metal can:

Samples were placed in a polyethylene bag (Suntec-LD M2206 (additive free) 100×210×0.1 mm, TOWA KAKO CO., LTD.) and tightened with Convex (CV100N, SHIBAKEISOZAI CO., LTD.). This bag was further placed in a polyethylene bag (Suntec-LD M2206 (additive free) 100×210×0.1 mm, TOWA KAKO) CO., LTD.) and similarly tightened with Convex (CV100N, SHIBAKEISOZAI CO., LTD.). The samples under the same storage conditions were put together in a metal can (3dia, a stainless steel can with an inner diameter of 16 cm and a depth of 18 cm) containing silica gel (using raw materials manufactured by Fuji Silysia Chemical Ltd., contained in 1 g bag).

TABLE 3

| Storage conditions | | | |
|---|---|---|---|
| Temperature | Relative humidity | Light | Packaging form |
| 40 ± 2° C. | 75 ± 5% RH | Protect from light | Double polyethylene bag, Convex (containing desiccant), metal can |
| 25 ± 2° C. | 60 ± 5% RH | Protect from light | Double polyethylene bag, Convex (containing desiccant), metal can |
| 5 ± 3° C. | | Protect from light | Double polyethylene bag, Convex (containing desiccant), metal can |

TABLE 4

| Storage conditions | | | |
|---|---|---|---|
| Temperature | Relative humidity | Light | Packaging form |
| 40 ± 2° C. | 75 ± 5% RH | Protect from light | Double polyethylene bag, Convex (containing desiccant), metal can |

The content of the compound represented by Formula (III) was confirmed in the same manner as in Test Example 1.

(Results)

For Example 1 and Reference Example 1, the amount of the compound represented by Formula (III) relative to the amount of the compound represented by Formula (I) or the like in the product stored over time is shown in Table 5. In the table, M represents month. The same applies to other tables.

The content ratio of the compound represented by Formula (III) to the amount of the compound represented by Formula (I) or the like under a condition of 10±2° C. and a relative humidity of 75±5% (in Table 5, expressed as 40±2° C./75±5% RH) was 15 ppm (increased amount from the start of the test was 12 ppm) in 1 month and 18 ppm (increased amount from the start of the test was 15 ppm) in 3 months for the sample of Reference Example 1. On the other hand, in the sample of Example 1, the content ratio was 2 ppm (increased amount from the start of the test was 1 ppm) in 1 month, 3 ppm (increased amount from the start of the test was 2 ppm) in 8 months, and 4 ppm (increased amount from the start of the test was 2 ppm) in 6 months. The wet-pulverized sample of Example 1 had a suppressed increase in the amount of the compound represented by Formula (III), as compared with the sample of Reference Example 1. From this, it was found that the stability is improved by wet-pulverizing the compound represented by Formula (I) or the like.

In addition, from the above results, it was confirmed that in a stability testing under a condition of 40±2° C. and a relative humidity of 75±5% for 1 month, the crystal of the present invention has a content ratio of the compound represented by Formula (III) to the amount of the compound represented by Formula (I) or the like of 0.0001 to 10 ppm. Furthermore, it was confirmed that in a stability testing under a condition of 10±2° C. and a relative humidity of 75±5% for 6 months, the crystal of the present invention has a content ratio of the compound represented by Formula (III) to the amount of the compound represented by Formula (I) or the like of 0.0001 to 20 ppm.

TABLE 5

| | Storage conditions | Initial (ppm) | 1M (ppm) | 3M (ppm) | 6M (ppm) | 12M (ppm) |
|---|---|---|---|---|---|---|
| Example 1 | 40 ± 2° C./ 75 ± 5% RH | 1 | 2 | 3 | 4 | — |
| | 25 ± 2° C./ 60 ± 5% RH | 1 | — | 1 | 1 | 2 |
| | 5 ± 3° C. | 1 | — | 1 | 1 | 1 |
| Reference example 1 | 40 ± 2° C./ 75 ± 5% RH (containing silica gel) | 3 | 15 | 18 | — | — |

(Example 2) Production of Wet-Pulverized Product of Compound Represented by Formula (I) (2)

2-Propanol (2266 g), water (1004 g), methanol (3011 g), and 48% sodium hydroxide (162 g, 5.56 mol) were added to an anhydrate crystal (1129 g, 2.800 mol) of the compound represented by Formula (I) to dissolve the anhydrate crystal, and the temperature was raised to 50° C. Formic acid (307 g, 6.67 mol) and an anhydrate crystal (1.16 g) of the compound represented by Formula (J) were added while performing a pressure type homogenizer (LAB2000, SMT) treatment, and then the mixture was stirred for 2 hours under a pressure type homogenizer treatment to precipitate the anhydrate crystal of the compound represented by Formula (I), thereby obtaining a slurry.

Water (4.64 kg) was added to the obtained slurry under a pressure type homogenizer treatment, and the slurry was cooled to 25° C. The obtained slurry was wet-pulverized with a pressure type homogenizer and then filtered to obtain an anhydrate crystal (1067 g, 90% particle size distribution: 7.17 μm, content ratio of the compound represented by Formula (III): 1.0 ppm) of the compound represented by Formula (I).

(Example 3) Production of Wet-Pulverized Product of Compound Represented by Formula (I) (3)

To the compound (9) (70.00 g, 134.12 mmol), 2-propanol (109.91 g), water (63.00 g), and 48% sodium hydroxide (27.95 g, 335.4 mmol) were added, and the mixture was stirred at 25° C. for 5 hours and dissolved. 2-Propanol (16.49 g), water (217.00 g) and methanol (127.44 g) were added to the reaction solution, formic acid (9.88 g) was added thereto at 25° C. while performing a pressure type homogenizer (LAB2000, SMT) treatment, the mixture was stirred for 35 minutes, and formic acid (8.61 g) and water (70.00 g) were added dropwise thereto over 2 hours. By adding water (7.00 g) and methanol (27.70 g), a dihydrate crystal of the compound represented by Formula (I) was precipitated to obtain a slurry.

A seed crystal (70 mg) of an anhydrate of the compound represented by Formula (I) was added to the obtained slurry, and the mixture was stirred at 50° C. for 1 hour and then cooled to 25° C. The obtained slurry was wet-pulverized with a pressure type homogenizer and then filtered to obtain an anhydrate crystal (60.44 g, 90% particle size distribution: 6.48 μm, content ratio of the compound represented by Formula (III): 1.5 ppm) of the compound represented by Formula (I).

(Example 1) Production of Wet-Pulverized Product of Compound Represented by Formula (I) (4)

To an anhydrate crystal (1168 g, 2.300 mol) of the compound represented by Formula (I), 2-propanol (2166 g), water (4642 g), methanol (2260 g), and 48% sodium hydroxide (479 g, 5.75 mol) were added to dissolve the anhydrate crystal (content ratio of the compound represented by Formula (III): 58.4 ppm). Thereafter, formic acid (169 g, 3.67 mol) was added thereto at 25° C., and the mixture was stirred at 25° C. for 30 minutes while performing a pressure type homogenizer (LAB2000, SMT) treatment. An aqueous solution obtained by mixing formic acid (148 g, 3.22 mol) and water (1202 g) was added to the obtained slurry at 25° C., and then water (240 g) was further added to precipitate a dihydrate crystal of the compound represented by Formula (I), thereby obtaining a slurry.

A seed crystal (1.20 g) of an anhydrate of the compound represented by Formula (I) and methanol (475 g) were added to the obtained slurry, and the mixture was stirred at 50° C. for 1 hour and then cooled to 25° C. The obtained slurry was wet-pulverized with a pressure type homogenizer and then filtered to obtain an anhydrate crystal (1659 g, 90% particle size distribution: 8.82 μm, content ratio of the compound represented by Formula (III): 1.3 ppm) of the compound represented by Formula (I).

A total amount of the content ratio of the compound represented by Formula (III) contained in the filtrate after filtration and the obtained crystal was 67.1 ppm, and an increased amount of the content ratio of the compound represented by Formula (III) during the crystallization operation was 67.1−58.4=8.7 ppm.

Hereinafter, a method for producing a crystal of the compound represented by Formula (I) or the like including a wet pulverization step using a rotor stator type homogenizer will be described.

(Example 5) Production of Wet-Pulverized Product of Compound Represented by Formula (I) (5)

To the compound (9) (220.00 g, 421.49 mmol), 2-propanol (34542 g), water (198.22 g), and 48% sodium hydroxide (87.82 g, 1051 mmol) were added, and the mixture was stirred at 30° C. for 3 hours. Then, 154.81 g of the obtained reaction solution was taken, 2-propanol (18.85 g), water (36.01 g), and methanol (101.35 g) were added, and the temperature was raised to 50° C. Formic acid (10.58 g, 2299 mmol) and a seed crystal (40.07 mg) of an anhydrate of the compound represented by Formula (I) were added while performing a rotor stator type homogenizer (magic LAB, IKA) treatment, and then the mixture was stirred for 1 hour under a rotor stator type homogenizer treatment to precipitate an anhydrate crystal of the compound represented by Formula (I), thereby obtaining a slurry.

Water (160.32 g) was added to the obtained slurry under a rotor stator type homogenizer treatment, and the slurry was cooled to 25° C. The obtained slurry was wet-pulverized with a rotor stator type homogenizer and then filtered to obtain an anhydrate crystal (33.67 g, 90% particle size distribution: 27.57 μm) of the compound represented by Formula (I).

(Example 6) Production of Wet-Pulverized Product of Compound Represented by Formula (I) (6)

2-Propanol (49.00 g), water (13.20 g), methanol (60.81 g), and 48% sodium hydroxide (9.58 g, 115 mmol) were added to an anhydrate to crystal (23.36 g, 44.75 mmol) of the compound represented by Formula (I), and the temperature was raised to 50° C. Formic acid (6.50 g, 141 mmol) and a seed crystal (24.75 mg) of an anhydrate of the compound represented by Formula (I) were added while performing a rotor stator type homogenizer (HG92, SMT) treatment, and then the mixture was stirred for 2 hours under a rotor stator type homogenizer treatment to precipitate the anhydrate crystal of the compound represented by Formula (I), thereby obtaining a slurry. Water (96.32 g) was added to the obtained slurry under a rotor stator type homogenizer treatment, and the slurry was cooled to 25° C. The obtained slurry was wet-pulverized with a rotor stator type homogenizer and then filtered to obtain an anhydrate crystal (22.58 g, 90% particle size distribution: 61.22 μm, content ratio of the compound represented by Formula (III): 1.0 ppm) of the compound represented by Formula (I).

Hereinafter, a method for producing the compound represented by Formula (I) or the like including a wet pulverization step using a bead mill will be described.

(Example 7) Production of Wet-Pulverized Product of Compound Represented by Formula (I) (7)

A solution of methanol/2-propanol/water (1.1/0.9/2 vol) was added to an anhydrate crystal of the compound represented by Formula (I) to form a slurry.

The obtained slurry was wet-pulverized with a bead mill (DYNO-MILL nanodisperser research lab type, Willy A. Bachofen AG) and then filtered to obtain an anhydrate crystal (90% particle size distribution: 2.791 μm) of the compound represented by Formula (I). The 90% particle size distribution was measured by the method described in Test Example 5.

(Test Example 5) Method for Measuring 90% Particle Size Distribution of Wet-Pulverized Product Using Bead Mill A 90% particle size distribution was measured according to the following method and conditions.

Measuring instrument: particle size distribution measuring apparatus (Mastersizer 2000, Malvern Panalytical Ltd)

Dispersion solvent: 0.1 g of sodium dodecyl sulfate (SDS) was dissolved in 1 L of water Rotation speed: 2500 rpm Ultrasound: 50%

Slurry concentration: adjusted between 10 to 20%

The following Reference Examples 2 and 3 show a method for producing a crystal of a compound represented by Formula (I) or the like, which does not include a wet pulverization treatment step.

Reference Example 2

To the compound (9) (220.00 g, 421.19 mmol), 2-propanol (345.42 g), water (198.22 g), and 48% sodium hydroxide (87.82 g, 1054 mmol) were added, and the mixture was stirred at 30° C. for 3 hours to obtain a reaction solution (851.31 g).

2-Propanol (3.77 g), water (7.20 g), and methanol (20.26 g) were added to the obtained reaction solution (30.53 g, content ratio of the compound represented by Formula (III): 178.9 ppm), and the temperature was raised to 50° C. Formic acid (2.12 g, 46.1 mmol) and a seed crystal (18.53 mg) of an anhydrate of the compound represented by Formula (I) were added, and then the mixture was stirred for 5 hours to precipitate an anhydrate crystal of the compound represented by Formula (I), thereby obtaining a slurry. Water (32.06 g) was added to the obtained slurry, and the mixture was cooled to 25° C. and filtered to obtain an anhydrate crystal (7.35 g, content ratio of the compound represented by Formula (III): 1.3 ppm) of the compound represented by Formula (I).

A total amount of the content ratio of the compound represented by Formula (III) contained in the filtrate after filtration and the obtained crystal was 316.7 ppm, and an increased amount of the content ratio of the compound represented by Formula (III) during the crystallization operation was 316.7−178.9=37.8 ppm.

Reference Example 3

To the compound (9) (41.00 g, 78.55 mmol), 2-propanol (61.38 g), water (36.93 g), and 48% sodium hydroxide (16.36 g, 196.3 mmol) were added, and the mixture was stirred at 35° C. for 4 hours to obtain a reaction solution (158.29 g, content ratio of the compound represented by Formula (III): 82.0 ppm).

2-Propanol (3.77 g), water (5.60 g), and methanol (20.27 g) were added to the obtained reaction solution (30.89 g), and the temperature was raised to 50° C. Formic acid (2.12 g, 46.1 mmol) and a seed crystal (8.21 mg) of an anhydrate of the compound represented by Formula (I) were added, and then the mixture was stirred for 8 hours to precipitate an anhydrate crystal of the compound represented by Formula (I), thereby obtaining a slurry. Water (7.18 g) was added to the obtained slurry, and the mixture was cooled to 25° C. and filtered to obtain an anhydrate crystal (7.18 g, 90% particle size distribution: 169.84 pin) of the compound represented by Formula (I).

A total amount of the content ratio of the compound represented by Formula (III) contained in the filtrate after filtration and the obtained crystal was 252.5 ppm, and an increased amount of the content ratio of the compound represented by Formula (III) during the crystallization operation was 252.5−82.0=170.5 ppm.

The increased amount of the content ratio of the compound represented by Formula (III) during the crystallization operation in Reference Examples 2 and 3 and Examples 1 and 4 is shown in Table 6.

TABLE 6

| | Increased amount (ppm) of content ratio of compound represented by Formula (III) during crystallization operation | Stirring time until slurry of compound represented by Formula (I) is obtained | Temperature during wet pulverization treatment step |
|---|---|---|---|
| Reference Example 2 | 137.8 | 5 h | 50° C. |
| Reference Example 3 | 170.5 | 8 h | 50° C. |
| Example 1 | 65.3 | 1 h | 50° C. |
| Example 4 | 8.7 | 30 min | 25° C. |

In Example 1 including a wet pulverization treatment step using a wet pulverizer, the increased amount of the content ratio of the compound represented by Formula (III) during the crystallization operation was smaller than that in Reference Examples 2 and 3 not including the wet pulverization treatment step using a wet pulverizer. From this, it was found that the increased amount of the content ratio of the compound represented by Formula (III) during the crystallization operation can be suppressed by the wet pulverization treatment step using a wet pulverizer.

This is presumed to be because the wet pulverization treatment step using a wet pulverizer could promote the nucleation of a crystal and shorten the crystallization time of an anhydrate crystal of the compound represented by Formula (I).

Furthermore, in Example 4, the wet pulverization treatment step using a wet pulverizer is included, and by performing the wet pulverization treatment step at 25° C., the increased amount of the content ratio of the compound represented by Formula (III) during the crystallization operation could be greatly reduced. In Example 4, a dihydrate crystal of the compound represented by Formula (I) was crystallized by performing the wet pulverization treatment step at 25° C., and then solvent-mediated transition to an anhydrate crystal of the compound represented by Formula (I) was performed.

By changing the temperature in the wet pulverization treatment step from 50° C. to 25° C., the crystallization time of a crystal of the compound represented by Formula (I) could be shortened. When Example 4 and Example 1 were compared, the shortened time is half, but the effect of suppressing the increased amount of the content ratio of the compound represented by Formula (III) was very high. From this, it is presumed that the suppression of the increased amount of the content ratio of the compound represented by Formula (III) during the crystallization operation had an effect due to low-temperature crystallization and/or via of a dihydrate crystal.

The 90% particle size distribution of the anhydrate crystal of the compound represented by Formula (I) and the content ratio of the compound represented by Formula (III) in the anhydrate crystal of Reference Examples 2 and 3 and Examples 1 and 4 is shown in Table 7.

In Examples 1 and 4 including the wet pulverization treatment step using a wet pulverizer, it was confirmed that the 90% particle size distribution of the crystal of the compound represented by Formula (I) is 100 μm or less.

TABLE 7

| | 90% particle size distribution (μm) | Content ratio (ppm) of compound represented by Formula (III) in anhydrate crystal |
|---|---|---|
| Reference Example 2 | Unmeasured | 1.30 |
| Reference Example 3 | 169.84 | Unmeasured |
| Example 1 | 5.51 | 1.10 |
| Example 4 | 8.82 | 1.30 |

Hereinafter, a pharmaceutical composition containing the compound represented by Formula (I) obtained by wet pulverization was produced.

(Example 8) Production of Pharmaceutical Composition Containing Compound Represented by Formula (I)

A compound represented by Formula (I) produced in the same manner as in Example 4 was wet-granulated in the formulation shown in Table 8 to produce a pharmaceutical composition containing the compound represented by Formula (I) or the like.

TABLE 8

| | Example 8 |
|---|---|
| Compound represented by Formula (I) | 300.0 |
| Triethyl citrate | 6.0 |
| Anhydrous lactose 24AN | 513.0 |
| Low-substituted hydroxypropylcellulose LH21 | 45.0 |
| Hydroxypropylcellulose SL | 27.0 |
| Vegetable magnesium stearate | 9.0 |
| Total of core tablet (mg) | 900.0 |
| OPADRY ORANGE 03A430007 | 18.5 |
| Triethyl citrate | 1.3 |
| Total of coating layer (mg) | 19.8 |
| Total | 919.8 |

The compound represented by Formula (I) produced in the same manner as in Example 4, anhydrous lactose 24AN (DFE Pharma GmbH & Co. KG), low-substituted hydroxypropylcellulose LH21 (Shin-Etsu Chemical Co., Ltd.), and hydroxypropylcellulose SSL (Nippon Soda Co., Ltd.) were nixed, and sieved with a 30-mesh wire mesh to perform bag mixing. Triethyl citrate (Merck KGaA) was dissolved in purified water and wet-granulated with the mixture with a continuous wet granulator (CTS-MG100, Powrex Corporation) at a water for granulation of 20% (w/w). The granulated product was dried with a fluidized bed granulator (CTS-FD-01W, Powrex Corporation) at an aeration temperature of 75° C. After drying, the particles were adjusted with a screen mill (QC-197S, Powrex Corporation). The sized granulated product and vegetable magnesium stearate (Mallinckrodt Pharmaceuticals plc) were mixed with a lubricant by bag mixing, and tableting was performed with a static compressor (ABM4100S type, manufactured by JT Toshi Co., Ltd.).

The core tablet was coated with OPADRY ORANGE 03A430007 (Colorcon Japan LLC) and triethyl citrate (Merck KGaA) to produce a film-coated tablet. A coating film amount per tablet was 2% (w/w) (19.8 mg/tablet) with respect to a mass of the core tablet.

Each condition is as follows.

(Mixing Conditions)

Bag mixing 10 times each left and right (Granulation Conditions)

Continuous wet granulator: CTS-MG100

Center blade rotation speed: 5000 $min^{-1}$

Scraper rotation speed: 50 $min^{-1}$

Water for granulation: 20%

Treatment speed: 20 kg/h (as mixed powder)

(Drying Conditions)

Dryer: CTS-FD-01W

Air supply temperature: 75° C. (preset temperature)

Air supply volume: 1.2 m3/min

Loss on drying: 1.0% or less (Particle Adjusting Conditions)

Sizing machine: QC-197S

Screen: aperture 1.143 mm, round hole

Impeller rotation speed: 2000 $min^{-1}$

Impeller shape: round (Lubricant Mixing Condition 1)

Bag mixing 10 times each left and right (Tableting Conditions)

Tableting machine: ABM100S type static compressor

Punch: diameter of 17.6×9.2 mm, oval type, CrN coating

Load speed: 2.0 F.S./min (F.S.=10 kN)

Hold time: 1 second

Hold point: 11.0 kN to 14.0 kN (Covering Conditions)

HICOATER LABO (Freund Corporation)

Charge: about 250 to 300 g

Air blowing temperature: 50 to 60° C. (preset temperature)

Air supply volume: 0.8 $m^3$/min

Static pressure in pan: −50 Pa or less

Spray pressure: 0.3 MPa

Flow meter display: 30 NL/min

Spray gun: NAT-2 type, 1 spray gun (nozzle cap diameter: 2 mm, nozzle diameter: 1.0 mm)

Pan rotation speed: 20 $min^{-1}$

Liquid velocity: 1.5 to 3.0 g/min

Spray distance: about 10 to 15 cm to tablet surface

End point of coating: average mass increase of tablet of 18.2 mg or more

The sample of Example 8 was subjected to the PTP packaging shown in Table 9.

TABLE 9

| | Packaging material | |
|---|---|---|
| | Molding agent | Lid material |
| Example 8-1 | Aclar PA 200/02 (191/51) | Push-Thru Blister Lidding 20 μm Aluminum Foil |
| Example 8-2 | Formpack 3PLY | |
| Example 8-3 | Formpack Dessiflex Plus | |

(Example 8-4) Production of Pharmaceutical Composition Containing Compound Represented by Formula (I)

The dry-pulverized compound represented by Formula (I) was wet-kneaded and/or wet-granulated in the formulation shown in Table 10 to produce a pharmaceutical composition containing the compound represented by Formula (I) or the like.

TABLE 10

| | Example 8-4 |
|---|---|
| Compound represented by Formula (I) | 50.0 |
| Triethyl citrate | 1.0 |
| Anhydrous lactose 24AN | 85.5 |
| Low-substituted hydroxypropylcellulose LH21 | 7.5 |
| Hydroxypropylcellulose SL | 4.5 |
| Vegetable magnesium stearate | 1.5 |
| Total of core tablet (mg) | 150.0 |
| OPADRY ORANGE 03A430007 | 5.6 |
| Triethyl citrate | 0.4 |
| Total of coating layer (mg) | 6.0 |
| Total | 156.0 |

The compound represented by Formula (I) produced by the method of Reference Example 1, anhydrous lactose 24AN (DFE Pharma GmbH & Co. KG), and low-substituted hydroxypropylcellulose LH21 (Shin-Etsu Chemical Co., Ltd.) were mixed, sieved with a 30-mesh wire mesh, and mixed with a high speed mixer (10 type, Fukae Kogyo Co., Ltd.) to obtain a mixture. Hydroxypropylcellulose SSL (Nippon Soda Co., Ltd.) and triethyl citrate (Merck KGaA) were dissolved in purified water, and the mixture was wet-granulated with a high speed mixer (10 type. Fukae Kogyo Co., Ltd.) at a water for granulation of 23% (w/w). The granulated product was sized with a power mill (SHOWA KAGAKUKIKAI CO., LTD., P-3S type), and dried with a fluidized bed granulator (5 type) (GPCG 5 type, Powrex Corporation) at an aeration temperature of 65° C., After drying, the particles were adjusted with a power mill (P-3 type, SHOWA KAGAKUKIKAI CO., LTD). The sized granulated product and vegetable magnesium stearate (Mallinckrodt Pharmaceuticals plc) were mixed with a lubricant with a mixer (22 L V-type), and tableting was performed with a tableting machine (LIBRA836BK-AWCZ type, KIKUSUI SEISAKUSHO LTD.).

The core tablet was coated with OPADRY ORANGE 03A430007 (Colorcon Japan LLC) and triethyl citrate (Merch KGaA) to produce a film-coated tablet. A coating film amount per tablet was 4% (w/w) (6.0 mg/tablet) with respect to a mass of the core tablet.

The film-coated tablet was subjected to the PTP packaging shown in Table 11.

TABLE 11

| | Packaging material | |
|---|---|---|
| | Molding agent | Lid material |
| Example 8-4 | Aclar PA 200/02 (191/51) | Push-Thru Blister Lidding 20 μm Aluminum Foil |

Each condition is as follows.

(Mixing Conditions)

Mixer: 10 type high speed mixer

Agitator rotation speed: 250±20 $min^{-1}$

Mixing time: 30 to 35 seconds (Granulation Conditions)

Granulator: 10 type high speed mixer

Agitator rotation speed: 250±20 $min^{-1}$

Chopper rotation speed: 2500±100 $min^{-1}$

Water for granulation: 23%

Liquid injection speed: 90 to 91 g/min

Stirring time after liquid injection: 0.5 to L 5 minutes (Sizing Conditions)

Sizing machine: P-3 type power mill

Basket: herringbone 2.5 mm

Rotation speed: 2,000±50 $min^{-1}$

Blade: spoiler blade (Drying Conditions)

Dryer: GPCG 5 type fluidized bed granulator

Air supply temperature: 65° C. (preset temperature)

Air supply volume: 0.5 to 5.0 m3/min

Loss on drying: 1.0% or less (Particle Adjusting Conditions)

Dryer: P-3 type power mill

Basket: Wire mesh 18 mesh

Rotation speed: 3000±50 $min^{-1}$

Blade: spoiler blade (Lubricant Mixing)

Mixer: 22 L V-type mixer

Rotation speed: 35±1.0 $min^{-1}$

Mixing time: 1 to 3 minutes (Tableting Conditions)

Tableting machine: LIBRA83GBK-AWCZ type tableting machine

Punch: diameter of 7.0 mm, two-stage R (13×2.3), CrN coating

Number of punches: 12

Rotation speed: 30±2.0 $min^{-1}$

Feed shoe: open (Covering Conditions)

AQC-48 type AQUA COATER

Charge: about 3.7 to 5.1 kg

Air blowing temperature: 50 to 70° C. (preset temperature)

Air supply volume: 3.5±0.5 m3/min

Static pressure in pan: 0 Pa or less

Spray pressure: 0.5±0.1 MPa

Flow meter display (atomizing): 60±20 NL/min

Flow meter display (pattern): 40±20 NL/min

Spray gun: NAT-2 type, 1 spray gun (nozzle cap type number: 015, nozzle diameter: 1.0 mm)

Pan rotation speed: G to 15 $min^{-1}$

Liquid velocity: 8 to 14 g/min

Spray distance: about 15 to 20 cm to tablet surface

End point of coating: average mass increase of tablet of 5.5 mg or more

The samples of Examples 8-1 to 8-4 were subjected to a stability testing under a condition of 40±2° C., a relative humidity of 75±5% (also referred to as 40±2° C./75±5% RH), and light shielding to evaluate the content of the compound represented by Formula (III).

(Test Example C) Stability Testing of Pharmaceutical Composition

Preparation of a standard solution, preparation of a sample solution, a method for measuring a total amount of a related substance, and a calculation formula were performed by the following method.

(Preparation of Standard Solution)

A standard sample of the compound represented by Formula (III) was prepared by the following method.

Step 1: About 20 mug of the compound represented by Formula (III) was weighed precisely, and a mixed solution of acetonitrile and water (4:1) was added to dissolve the compound to make exactly 100 mL.

Step 2: One milliliter of the solution of Step 1 was accurately taken, and a mixed solution of acetonitrile and water (4:1) was added to make exactly 100 mL.

Step 3: One milliliter of the solution of Step 2 was accurately taken, and a mixed solution of acetonitrile and water (4:1) was added to make exactly 100 mL.

Step 4: Five milliliters of the solution of Step 3 was accurately taken, and a mixed solution of acetonitrile and water (4:1) was added to make exactly 20 mL, thereby obtaining a standard solution.

(Preparation of Sample Solutions of Examples 8-1 to 8-3)

Step 1: One tablet of a 300 mg tablet was added to a 300 mL volumetric flask.

Step 2: To Step 1 was added 60 mL of water, and the mixture was vigorously shaken for 10 minutes to disintegrate the tablet completely. The shaking time was extended as necessary.

Step 3: To Step 2 was added 150 mL of acetonitrile, and the mixture was vigorously shaken for 30 minutes.

Step 4: After cooling, acetonitrile was added to make exactly 300 mL, a part of the liquid was centrifuged at 13000 rpm for 10 minutes, and the supernatant was used as a sample solution.

(Preparation of Sample Solutions of Examples 8-1 to 8-4)

Step 1: One tablet of a 50 mg tablet was added to a 50 mL volumetric flask.

Step 2: To Step 1 was added 10 mL of water, and the mixture was irradiated with ultrasonic waves for 10 minutes to disintegrate the tablet completely. The ultrasonic irradiation time was extended as necessary.

Step 3: To Step 2 was added 25 mL of acetonitrile, and the mixture was irradiated with ultrasonic waves for 30 minutes.

Step 4: After cooling, acetonitrile was added to make exactly 50 mL, a part of the liquid was centrifuged at 13000 rpm for 10 minutes, and the supernatant was used as a sample solution.

(Method for Measuring Total Amount of Related Substance)

An amount of the compound represented by Formula (III) was measured with a liquid chromatograph according to the following method and conditions.

Measuring instrument: LC/MS/MS (PM No. AESC76) manufactured by Agilent Technologies, Inc.

Column: L-column 24.6×150 mm, 3 μm

Column temperature: constant temperature at near 35° C.

Mobile phase A: 10 mM ammonium acetate

Mobile phase B: acetonitrile for liquid chromatography

Feed of mobile phase: The mixing ratio of mobile phase A and mobile phase B was changed as shown in Table 12 to control concentration gradient.

TABLE 12

| Time (min) after sample injection | Mobile phase A (%) | Mobile phase B (%) |
|---|---|---|
| 0 to 12 | 65 | 35 |
| 12 to 12.01 | 65 → 10 | 35 → 90 |
| 12.01 to 17 | 10 | 90 |
| 17 to 17.01 | 10 → 65 | 90 → 35 |
| 17.01 to 25 | 65 | 35 |

Post runtime: 5 minutes
Flow rate: 0.5 mL/min (retention time of compound represented by Formula (III): about 9 minutes)
Injection amount: 5 μL
Sample cooler temperature: constant temperature at near 10° C.
Needle washing solution: acetonitrile for liquid chromatography
Ionization method: ESI
Scan type: MRM
Polarity: positive
Precursor ion: m/z=187.2
Product ion: m/z=64.9
Fragmentor: 120
Collision energy: 33
Capillary 4000 V
Gas temperature: 350° C.
Gas flow rate: 12 L/min
Nebulizer: 40 psi
MS uptake time: 0 to 12 minutes
(Calculation Formula)

$$\text{Content (ppm) of compound represented by Formula (III)}=M_S \times P/100 \times (100-W_S)/100 \times A_T/A_S \times 1/C \times D \times 1000000 \quad \text{(Mathematical formula 5)}$$

$M_S$: Weighing amount (mg) of compound represented by Formula (III)
P: Purity (%) of compound represented by Formula (III)
$W_S$: Moisture (%) of compound represented b Formula (III)
$A_S$: Peak area of compound represented by Formula (II) obtained from standard solution
$A_T$: Peak area of compound represented by Form ula (III) obtained from sample solution
C: Theoretical content of compound represented by Formula (I) or the like (50 mg tablet: 50, 300 mg tablet: 300)
D: Dilution ratio (50 mg tablet: 1/80000, 300 mg tablet: 1/480000)
(Results)

For the samples of Examples 8-1 to 8-4, the amount of the compound represented by Formula (III) in the product stored over time is shown in Table 13. In the table, M represents month.

The content ratio of the compound represented by Formula (III) to the amount of the compound represented by Formula (I) or the like in the pharmaceutical composition containing the wet-pulverized compound represented by Formula (I) or the like was 1.6 ppm at the start of the test of Examples 8-1 to 8-3. After storage under a condition of 40±2° C., a relative humidity of 75±5%, and light shielding for 1 month, the content ratio was 1.6 ppm for Example 8-1, 1.7 ppm for Example 8-2, and 1.6 ppm for Example 8-2. From this result, it was confirmed that in a stability testing under a condition of 40±2° C. and a relative humidity of 75±5% for 1 month, the pharmaceutical composition of the present invention has a content ratio of the compound represented by Formula (III) to the amount of the compound represented by Formula (I) or the like of 0.0001 to 10 ppm.

After storage under a condition of 40±2° C., a relative humidity of 75±5%, and light shielding for 6 months, the content ratio was 2.4 ppm for Example 8-1, 2.1 ppm for Example 8-2, and 2.0 ppm for Example 8-3. From this result, it was confirmed that in a stability testing under a condition of 40±2° C. and a relative humidity of 75±5% for 6 months, the pharmaceutical composition of the present invention has a content ratio of the compound represented by Formula (III) to the amount of the compound represented by Formula (I) or the like of 0.0001 to 30 ppm.

Also for the sample of Example 8-4, which is a pharmaceutical composition obtained by wet granulation of a dry-pulverized compound represented by Formula (I) or the like, the content ratio was 1.8 ppm at the start of the test, 2.4 ppm at 2 months after the stability testing, and 3.2 ppm at 6 months after the stability testing, and an increase in the amount of the compound represented by Formula (III) was suppressed. From this result, it was confirmed that in a stability testing under a condition of 40±2° C. and a relative humidity of 75±5% for 1 month, the pharmaceutical composition of the present invention has a content ratio of the compound represented by Formula (III) to the amount of the compound represented by Formula (I) or the like of 0.0001 to 10 ppm. Furthermore, it was confirmed that in a stability testing under a condition of 40±2° C. and a relative humidity of 75±5% for 6 months, the pharmaceutical composition of the present invention has a content ratio of the compound represented by Formula (III) to the amount of the compound represented by Formula (I) or the like of 0.0001 to 30 ppm. This is an effect of wet granulation.

TABLE 13

| | Example 8-1 | Example 8-2 | Example 8-3 | Example 8-4 |
|---|---|---|---|---|
| Initial | 1.6 ppm | 1.6 ppm | 1.6 ppm | 1.8 ppm |
| 1M | 1.6 ppm | 1.7 ppm | 1.6 ppm | Unmeasured |
| 3M | 2.3 ppm | 2.0 ppm | 1.8 ppm | 2.4 ppm |
| 6M | 2.4 ppm | 2.1 ppm | 2.0 ppm | 3.2 ppm |

Formulation studies of the compound represented by Formula (I) or the like are shown below.

Reference Example 4

A crystal of an anhydride of the compound represented by Formula (I) obtained in accordance with Reference Example I mentioned above was dry-pulverized in a counter jet mill (100 AFG, Hosokawa Micron Corporation) to obtain a product.

Example 9

The sample of Reference Example 4 was weighed in a mortar, an appropriate amount of purified water was added thereto, and wet kneading was performed with a pestle. The resulting granulated product was sieved with a 20-mesh wire mesh, and dried at an aeration temperature of 60° C. for 30 minutes in an aeration dryer (TH-80, SATAKE CHEMICAL EQUIPMENT MFG., LTD.). Thereafter, the resulting product was sieved with a 20-mesh wire mesh to obtain a product.

(Test Example 7) Stability Testing

The samples obtained in Example 9 and Reference Example 4 were evaluated for the stability in the product stored over time.

A stability testing was performed under a condition of 60° C. glass bottle closed, 10° C. glass bottle closed, and 40° C./75% RH glass bottle opened to evaluate the content of the compound represented by Formula (III).

(Preparation of Standard Solution)

A standard sample of 5 ng/mL (corresponding to 5 ppm with respect to the sample solution) of the compound represented by Formula (ITI) was prepared by the following method.

Step 1: About 20 mg of the compound represented by Formula (III) was weighed precisely, and a mixed solution of acetonitrile and water (4:1) was added to dissolve the compound to make exactly 100 mL.

Step 2: One milliliter of the solution of Step 1 was accurately taken, and a mixed solution of acetonitrile and water (4:1) was added to make exactly 100 mL.

Step 3: One milliliter of the solution of Step 2 was accurately taken, and a mixed solution of acetonitrile and water (4:1) was added to make exactly 100 mL.

Step 4: Five milliliters of the solution of Step 8 was accurately taken, and a mixed solution of acetonitrile and water (4:1) was added to make exactly 20 mL, thereby obtaining a standard solution.

(Preparation of Sample Solution)

A sample solution was prepared by the following method.

Step 1: A sample in an amount corresponding to 50 mg of the compound represented by Formula (I) or the like was added to a 50 mL volumetric flask.

Step 2: To Step 1 was added 10 mL of water, and the mixture was irradiated with ultrasonic waves for 10 minutes to disintegrate the sample completely. The ultrasonic irradiation time was extended as necessary.

Step 3: To Step 2 was added 25 mL of acetonitrile, and the mixture was irradiated with ultrasonic waves for 30 minutes.

Step 4: After cooling, acetonitrile was added to make exactly 50 mL, a part of the liquid was centrifuged at 13000 rpm for 10 minutes, and the supernatant was used as a sample solution.

(Method for Measuring Total Amount of Related Substance)

An amount of the compound represented by Formula (III) was measured with a liquid chromatograph according to the following method and conditions.

Measuring instrument: LC/MS/MS (PM No. AES676) manufactured by Agilent Technologies, Inc.
Column: L-column 24.6×150 mm, 3 μm
Column temperature: constant temperature at near 35° C.
Mobile phase A: 10 mM ammonium acetate
Mobile phase B: acetonitrile for liquid chromatography
Feed of mobile phase: The mixing ratio of mobile phase A and mobile phase B was changed as shown in Table 14 to control concentration gradient.

TABLE 14

| Time (min) after sample injection | Mobile phase A (%) | Mobile phase B (%) |
|---|---|---|
| 0 to 12 | 65 | 35 |
| 12 to 12.01 | 65 → 10 | 35 → 90 |
| 12.01 to 17 | 10 | 90 |
| 17 to 17.01 | 10 → 65 | 90 → 35 |
| 17.01 to 25 | 65 | 35 |

Post runtime: 5 minutes
Flow rate: 0.5 mL/min (retention time of S202AA: about 9 minutes)
Injection amount: 5 μL
Sample cooler temperature: constant temperature at near 10° C.
Needle washing solution: acetonitrile for liquid chromatography
Ionization method: ESI
Scan type: MEM
Polarity: positive
Precursor ion: m/z=187.2
Product ion: m/z=64.9
Fragmentor: 120
Collision energy: 33
Capillary: 4000 V
Gas temperature: 350° C.
Gas flow rate: 12 L/min
Nebulizer: 40 psi
MS uptake time: 0 to 12 minutes (Calculation Formula)

$$\text{Content (ppm) of compound represented by Formula (III)}=M_S \times P/100\times(100-W_S)/100\times A_T/A_S\times 1/50\times 1/80000\times 1000000 \quad \text{(Mathematical formula 6)}$$

$M_S$: Weighing amount (mg) of compound represented by Formula (III)
P: Purity (%) of compound represented by Formula (III)
$W_S$: Moisture (%) of compound represented by Formula (JII)
$A_S$: Peak area of compound represented by Formula (III) obtained from standard solution
$A_T$: Peak area of compound represented by Formula (III) obtained from sample solution (Results)

For the samples of Example 9 and Reference Example 1, the amount of the compound represented by Formula (III) in the product stored over time is shown in Table 15. As a result, the wet-kneaded sample of Example 9 had a suppressed increase in the amount of the compound represented by Formula (III), as compared with the sample of Reference Example 4. From this, it was found that the stability is improved by wet-kneading and/or wet-granulating the compound represented by Formula (I) or the like. In the table, W represents week, and M represents month. The same applies to other tables.

In the sample of Reference Example 4, the content ratio of the compound represented by Formula (III) to the amount of the compound represented by Formula (I) or the like was 13.1 ppm in storage for 1 month under a condition of 40° C./75% RE glass bottle opened. On the other hand, the content ratio was 6.4 ppm in the sample of Example 9. From this result, it was confirmed that in a stability testing under a condition of 40±2° C. and a relative humidity of 75±5% (glass bottle opened) for 1 month, the pharmaceutical composition of the present invention has a content ratio of the compound represented by Formula (III) to the amount of the compound represented by Formula (I) or the like of 0,0001 to 10 ppm.

In the sample of Reference Example 4, the content ratio of the compound represented by Formula (III) to the amount of the compound represented by Formula (I) or the like was 19.7 ppm in storage for 3 months under a condition of 40° C./75% RH glass bottle opened. On the other hand, the content ratio was 7.1 ppm in the sample of Example 9. From the above results, it was strongly suggested that also in a stability testing under a condition of 40±2° C. and a relative humidity of 75±5% (glass bottle opened) for 6 months, the pharmaceutical composition of the present invention has a content ratio of the compound represented by Formula (III) to the amount of the compound represented by Formula (I) or the like of 0.0001 to 30 ppm.

TABLE 15

| | | Example 9 Wet kneading | Reference example 4 Untreated |
|---|---|---|---|
| Initial (ppm) | | 3.8 | 3.0 |
| 60° C. glass bottle closed (ppm) | 2W | 4.1 | 10.9 |
| 40° C. glass bottle closed (ppm) | 2W | 6.0 | 10.7 |
| | 1M | 6.7 | 17.2 |
| | 3M | 8.2 | 23.9 |
| 40° C./75% RH | 2W | 4.9 | 9.4 |
| glass bottle opened | 1M | 6.4 | 13.1 |
| (ppm) | 3M | 7.1 | 19.7 |

(Test Example 8) Differential Scanning Calorimetry

The samples of Example 9 and Reference Example 4 were subjected to differential scanning calorimetry (DSC).

(Differential Scanning Calorimetry (DSC))

About 10 mg of a sample was weighed in an aluminum pan, and measurement was performed by simple sealing. The measurement conditions are shown below. Incidentally, an error may occur within a range of ±2° C. in the measurement by differential scanning calorimetry (DSC).

Apparatus: TA Instruments Discovery

Measurement temperature range: 25° C. to 250° C.

Heating rate: 10° C./min

Atmosphere: $N_2$ 50 ML/min (Results)

Figure 5:
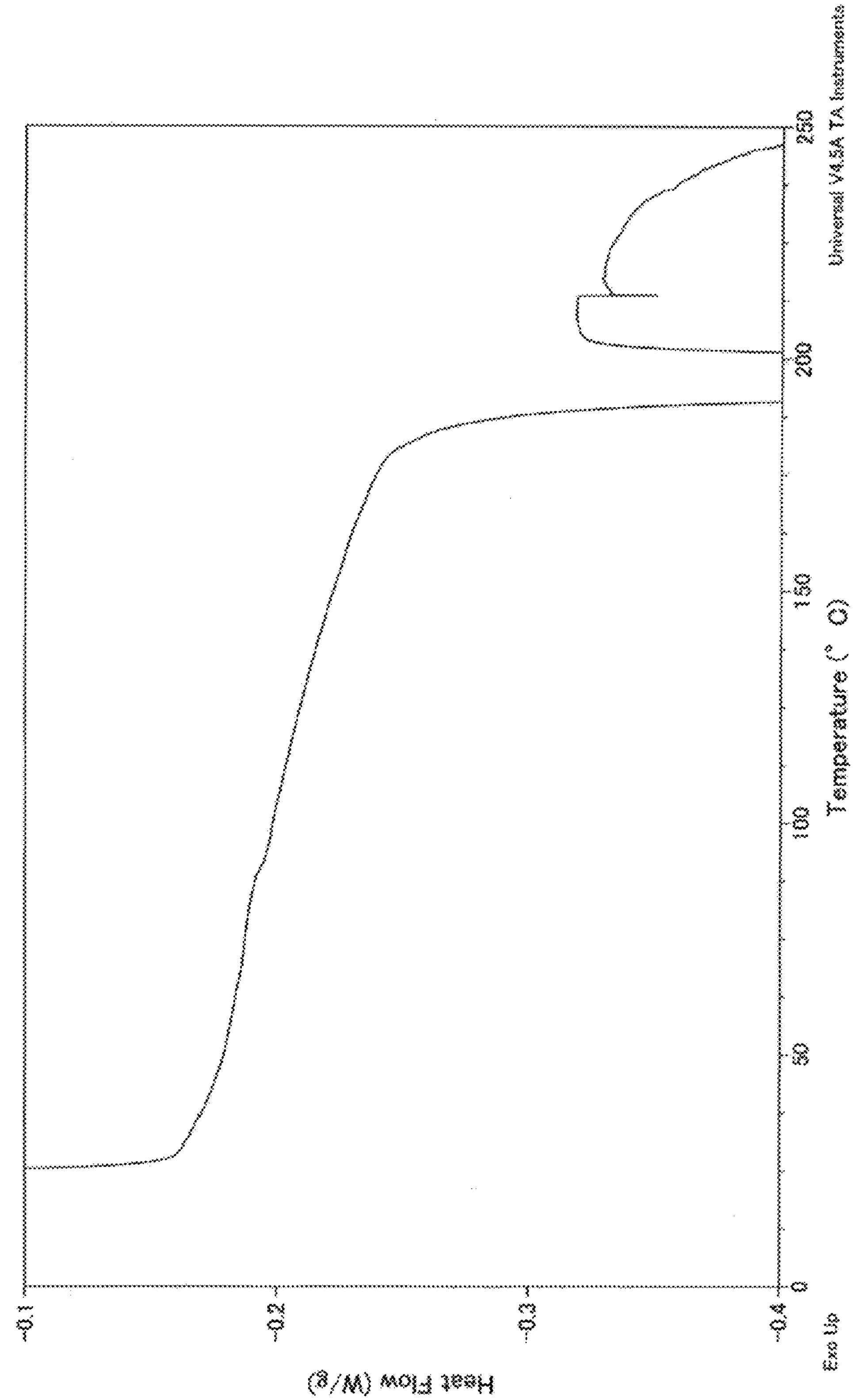
FIG. 5 shows results of differential scanning calorimetry (DSC) of a sample of Example 9. The horizontal axis represents temperature (° C.), and the vertical axis represents a heat flow.
Figure 6:
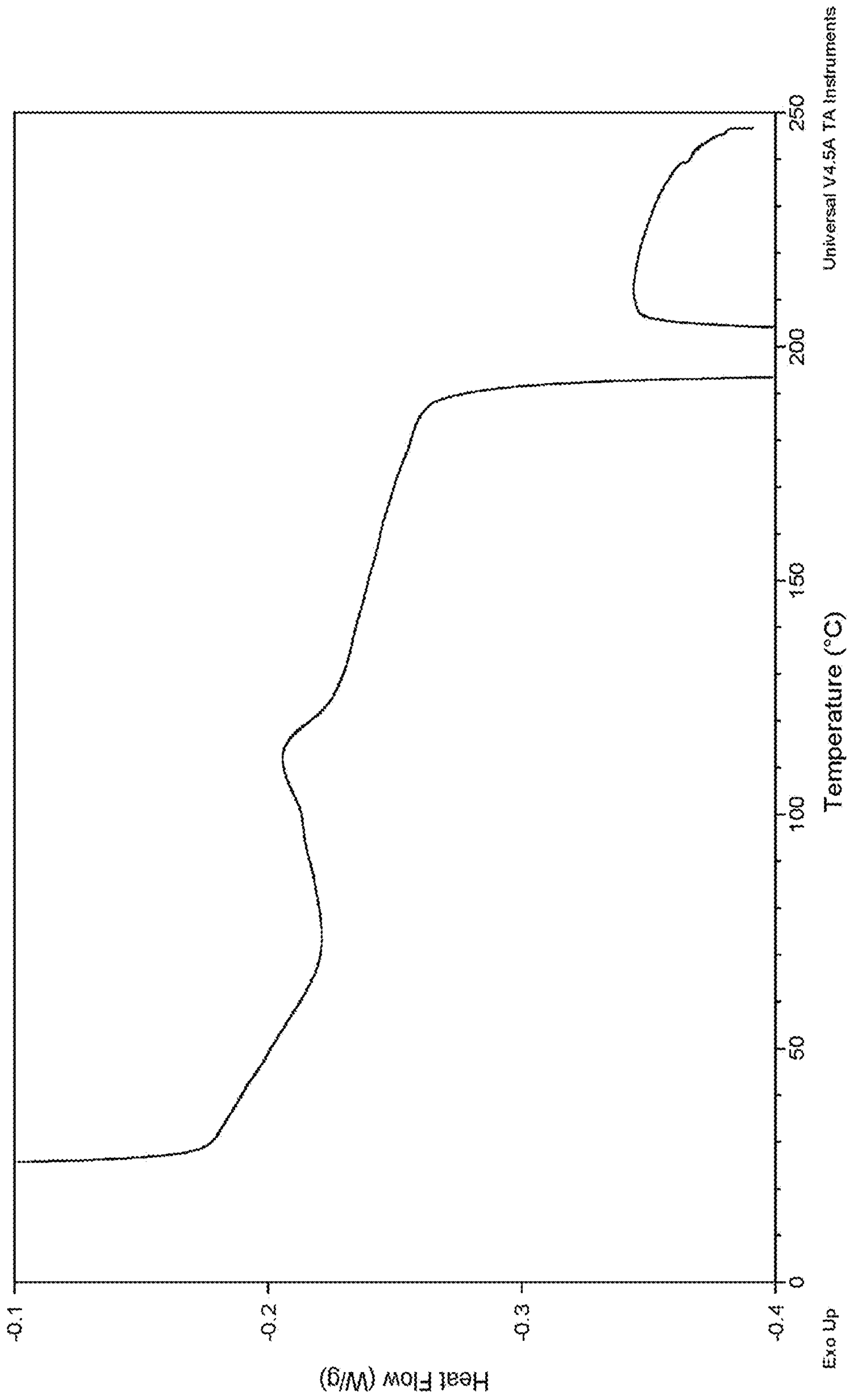
FIG. 6 shows results of differential scanning calorimetry (USC) of a sample of Reference Example 4. The horizontal axis represents temperature (° C.), and the vertical axis represents a heat flow.

The results of differential scanning calorimetry (DSC) measurement of the samples of Example 9 and Reference Example 4 are shown in FIGS. 5 and 6. As shown in FIG. 6, in the sample of Reference Example 1, an exothermic peak (peak top value is 114° C.) was confirmed from around 75° C., and it is considered that heat generation due to crystallization occurred. That is, it is considered that in the sample of Reference Example 4, an amorphous substance was slightly contained in the compound represented by Formula (I) or the like.

On the other hand, as shown in FIG. 5, in Example 9 in which the sample of Reference Example 4 was wet-kneaded, no exothermic peak was confirmed, and an amorphous substance was below a detection limit of differential scanning calorimetry (DSC). That is, the amount of an amorphous substance was reduced in the sample of Example 9. Therefore, in the sample of Example 9, it is considered that the amorphous substance contained in the compound represented by Formula (I) or the like was crystallized in the wet kneading step.

In general, since an amorphous substance has lower stability than that of a crystal, it is considered that an increase in the content of the compound represented by Formula (III) was suppressed by a decrease in the amount of an amorphous substance in the wet kneading step.

(Examples 10 to 14) Study of Stabilizer

A blending property test was performed on the compound represented by Formula (I) or the like and an additive, and the amount of the compound represented by Formula (III) in the product stored over time was evaluated. The sample and additive used in Reference Example 4 were weighed and mixed uniformly with a mortar and a pestle. An appropriate amount of purified water was added to the mixture, and wet kneading was performed with a pestle. The resulting granulated product was sieved with a 20-mesh wire mesh, and dried at an aeration temperature of 60° C. for 30 minutes in an aeration dryer (TH-80, SATAKE CHEMICAL EQUIPMENT MFG., LTD.). Thereafter, the resulting product was further sieved with a 20-mesh wire mesh to obtain samples of Examples 10 to 14. A blending ratio of the additive and the compound represented by Formula (I) of each sample is as shown in Table 16.

(Additive)

As additives, triethyl citrate (Merck KGaA), medium-chain triglyceride miglyol 812 (CREMER OLEO GmbH & Co. KG) (hereinafter referred to as miglyol), macrogol 6000 (NOF CORPORATION), anhydrous lactose 24AN (DFE Pharma GmbH & Co. KG), and hydroxypropylcellulose SL (Nippon Soda Co., Ltd.) were used.

TABLE 16

| | Additive | Preparation method | Blending ratio compound represented by Formula (I) or the like: additive |
|---|---|---|---|
| Example 10 | Triethyl citrate | Wet kneading | 10:1 |
| Example 11 | Miglyol 812 | Wet kneading | 10:1 |
| Example 12 | Macrogol 6000 | Wet kneading | 10:1 |
| Example 13 | Anhydrous lactose 24AN | Wet kneading | 1:10 |
| Example 14 | Hydroxypropylcellulose SL | Wet kneading | 2:1 |

(Test Example 9) Stability Testing

The samples of Examples 10 to 14 were subjected to a stability testing under a condition of 60° C. glass bottle closed (referred to as 60° C. closed in Table 17) and 40° C. glass bottle closed (referred to as 40° C. closed in Table 17) to evaluate the content of the compound represented by Formula (III).

The content of the compound represented by Formula (II) was confirmed in the same manner as in Test Example 7.

(Results)

The amount of the compound represented by Formula (III) in the product stored over time of the samples of Examples 10 to 14 together with Example 9 and Reference Example 4 is shown in Table 17. As a result, the content of the compound represented by Formula (III) increased or decreased depending on the type of the additive, as compared with the sample of Example 9 to which no additive was added. Triethyl citrate, miglyol, and macrogol 6000 suppressed an increase in the amount of the compound represented by Formula (III) in the product stored over time, as compared with Example 9 in which no additive was added. Triethyl citrate, miglyol, and macrogol 6000 were suggested to be useful as stabilizers. Also in Examples 13 and 14 in which anhydrous lactose and hydroxypropylcellulose SL were added, an increase in the amount of the compound represented by Formula (III) in the product stored over time was suppressed, as compared with the sample of Reference Example 4.

TABLE 17

| | Additive | Initial (ppm) | 60° C. closed (ppm) 2W | 40° C. closed (ppm) 2W | 1M | 3M |
|---|---|---|---|---|---|---|
| Reference example 4 | | 3.0 | 10.9 | 10.7 | 17.2 | 23.9 |
| Example 9 | None | 3.8 | 4.1 | 6.0 | 6.7 | 8.2 |
| Example 10 | Triethyl citrate | 2.8 | 3.1 | 3.8 | 2.9 | 4.3 |
| Example 11 | Miglyol 812 | 4.2 | 2.9 | 3.9 | 3.8 | 2.8 |
| Example 12 | Macrogol 6000 | 1.9 | 5.6 | 2.6 | 3.0 | 5.5 |
| Example 13 | Anhydrous lactose 24AN | 2.4 | 8.4 | 7.1 | 9.5 | 10.7 |
| Example 14 | Hydroxypropyl-cellulose SL | 2.3 | 7.8 | 6.2 | 9.6 | 12.3 |

Hereinafter, formulation studies on a mortar scale were conducted.

From the results of Test Example 9, triethyl citrate and miglyol in which the increased amount of the compound represented by Formula (III) was low were selected, and studies of formulation and production methods of a 10 mg tablet and a 0.50 mg tablet were conducted on a mortar scale. Anhydrous lactose 24 AN (DFE Pharma (GmbH & Co. KG) was used as an excipient, hydroxypropylcellulose SL (Nippon Soda Co., Ltd.) was used as a binder, low-substituted hydroxypropylcellulose LH21 (Shin-Etsu Chemical Co., Ltd.) was used as a disintegrant, and vegetable magnesium stearate (Mallinckrodt Pharmaceuticals plc) was used as a lubricant.

(Examples 15 to 25) Production of 10 mg Tablet

A tablet containing 10 mg of the sample of Reference Example 4 and triethyl citrate or miglyol was produced on a mortar scale.

(Method for Producing Core Tablet)

The formulation per tablet is shown in Tables 18 and 19. The compound represented by Formula (I), anhydrous lactose 24AN (DFE Pharma GmbH & Co. KG), and low-substituted hydroxypropylcellulose LH21 (Shin-Etsu Chemical Co., Ltd.) were weighed, and mixed uniformly with a mortar and pestle. Hydroxypropylcellulose SL (Nippon Soda Co., Ltd.) and triethyl citrate (Merck KGaA) or miglyol (CREMER OLEO GmbH & Co. KG) were dissolved in purified water, and the granulating liquid was added to the mixture in the mortar and kneaded with the pestle. Further, purified water was added little by little and kneaded to obtain a granulated product. The moisture during granulation was adjusted to about 20%. The granulated product was sieved with a 20-mesh wire mesh, and dried at an aeration temperature of 60° C. in an aeration dryer (TH-80, SATAKE CHEMICAL EQUIPMENT MFG., LTD.). After drying, the resulting product was further sieved with a 20-mesh wire mesh and the particles were adjusted. The sized product and vegetable magnesium stearate (Mallinckrodt Pharmaceuticals plc) were mixed in a bottle, and a tablet was produced with a static compressor (ABM100S type, manufactured by JT Toshi Co. Ltd.).

TABLE 18

| | Example 15 | Example 16 | Example 17 | Example 18 | Example 19 | Example 20 |
|---|---|---|---|---|---|---|
| Blending amount of triethyl citrate (molar ratio to drug substance) | — | 0.05 | 0.1 | 0.15 | 0.2 | 0.3 |
| Compound represented by Formula (I) or the like | 10.0 | 10.0 | 10.0 | 10.0 | 10.0 | 10.0 |
| Trietbyl citrate | — | 0.27 | 0.54 | 0.82 | 1.09 | 1.63 |
| Anhydrous lactose 24AN | 116.0 | 115.7 | 115.5 | 115.2 | 114.9 | 114.4 |
| Low-substituted hydroxypropylcellulose LH21 | 15.0 | 15.0 | 15.0 | 15.0 | 15.0 | 15.0 |
| Hydroxypropylcellulose SL | 7.5 | 7.5 | 7.5 | 7.5 | 7.5 | 7.5 |
| Vegetable magnesium stearate | 1.5 | 1.5 | 1.5 | 1.5 | 1.5 | 1.5 |
| Total of core tablet (mg) | 150.0 | 150.0 | 150.0 | 150.0 | 150.0 | 150.0 |

TABLE 19

| | Example 21 | Example 22 | Example 23 | Example 24 | Example 25 |
|---|---|---|---|---|---|
| Blending amount of miglyol (molar ratio to drug substance) | 0.02 | 0.05 | 0.1 | 0.2 | 0.3 |
| Compound represented by Formula (I) or the like | 10.0 | 10.0 | 10.0 | 10.0 | 10.0 |
| Miglyol | 0.17 | 0.42 | 0.85 | 1.69 | 2.54 |
| Anhydrous lactose 24AN | 115.8 | 115.6 | 115.2 | 114.3 | 113.5 |
| Low-substituted hydroxypropylcellulose LH21 | 15.0 | 15.0 | 15.0 | 15.0 | 15.0 |
| Hydroxypropylcellulose SL | 7.5 | 7.5 | 7.5 | 7.5 | 7.5 |
| Vegetable magnesium stearate | 1.5 | 1.5 | 1.5 | 1.5 | 1.5 |
| Total of core tablet (mg) | 150.0 | 150.0 | 150.0 | 150.0 | 150.0 |

(Test Example 10) Stability Testing of Tablet

The samples of Examples 15 to 25 were subjected to a stability testing under a condition of 00° C. glass bottle closed (referred to as 60° C. closed in Table 20), 40° C. glass bottle closed (referred to as 40° C. closed in Table 20), and 40° C./75% RH glass bottle opened (referred to as 40° C./75% RH opened in Table 20) to evaluate the content of the compound represented by Formula (III).

Preparation of a sample solution and a calculation formula were performed by the following method, and preparation of a standard solution and a method for measuring a total amount of a related substance were performed in the same manner as in Test Example 7.

(Preparation of Sample Solution)

A sample solution was prepared by the following method.

Step 1: (One tablet of a 10 mg tablet was added to a 10 mL volumetric flask.

Step 2: To Step 1 was added 2 mL of water, and the mixture was irradiated with ultrasonic waves for 10 minutes to disintegrate the tablet completely. The ultrasonic irradiation time was extended as necessary.

Step 3: To Step 2 was added 5 mL of acetonitrile, and the mixture was irradiated with ultrasonic waves for 30 minutes.

Step 4: After cooling, acetonitrile was added to make exactly 10 mL, a part of the liquid was centrifuged at 13000 rpm for 10 minutes, and the supernatant was used as a sample solution.

(Calculation Formula)

Content (ppm) of compound represented by Formula (III)$=M_S \times P/100 \times (100-W_S)/100 \times A_T/A_S \times 1/C \times D \times 1000000$ (Mathematical formula 7)

$M_S$: Weighing amount (mg) of compound represented by Formula (III)

P: Purity (%) of compound represented by Formula (JII)

$W_S$: Moisture (%) of compound represented by Formula (III)

$A_S$: Peak area of compound represented by Formula (III) obtained from standard solution $A_T$: Peak area of compound represented by Formula (III) obtained from sample solution C: Theoretical content of compound represented by Formula (I) or the like (10 mg tablet: 10, 50 mg tablet: 50)

D: Dilution ratio (10 mg tablet: 1/400000, 50 ng tablet: 1/80000)

(Results)

For the samples of Examples 15 to 25, the results of measurement of the amount of the compound represented by Formula (III) in the product stored over time are shown in Tables 20 and 21. In Example 15 in which triethyl citrate and miglyol were not blended, an increase in the amount of the compound represented by Formula (III) was observed over time, but in each of the tablets in which triethyl citrate and miglyol were blended, an increase in the amount of the compound represented by Formula (III) was suppressed.

TABLE 20

| | Blending amount of triethyl citrate (molar ratio to drug substance) | Initial (ppm) | 60° C. closed (ppm) 2W | 40° C. closed (ppm) 1M | 40° C./7 5% RH opened (ppm) 1M |
|---|---|---|---|---|---|
| Example 15 | — | 4 | 12 | 8 | 8 |
| Example 16 | 0.05 | 2 | 5 | 3 | 3 |
| Example 17 | 0.1 | 2 | 4 | 2 | 3 |
| Example 18 | 0.15 | 2 | 3 | 2 | 3 |
| Example 19 | 0.2 | 2 | 3 | 2 | 3 |
| Example 20 | 0.3 | 2 | 3 | 3 | 3 |

TABLE 21

| | Blending amount of miglyol (molar ratio to drug substance) | Initial (ppm) | 60° C. closed (ppm) 2W | 40° C. closed (ppm) 1M | 40° C./75% RH opened (ppm) 1M |
|---|---|---|---|---|---|
| Example 21 | 0.02 | 2 | 3 | 3 | 3 |
| Example 22 | 0.05 | 2 | 2 | 4 | 4 |
| Example 23 | 0.1 | 1 | 2 | 3 | 1 |
| Example 24 | 0.2 | 2 | 2 | 4 | 5 |
| Example 25 | 0.3 | 2 | 2 | 1 | 4 |

(Test Example 11) Dissolution Test of Tablet

The samples of Examples 15, 18, and 19 and the sample of Example 18 stored under a condition of 60° C. glass bottle closed, 40° C. glass bottle closed, and 40° C./75% RH glass bottle opened were subjected to a dissolution test.

(Dissolution Test Method of Formulation)

A dissolution rate of the compound represented by Formula (I) was measured by the dissolution test method (Method 2, Paddle method) according to the Japanese Pharmacopoeia, A second fluid for dissolution test was used as the fluid used in the dissolution test method, and the rotation speed of the paddle was 50 rpm.

(Results)

Figure 7:
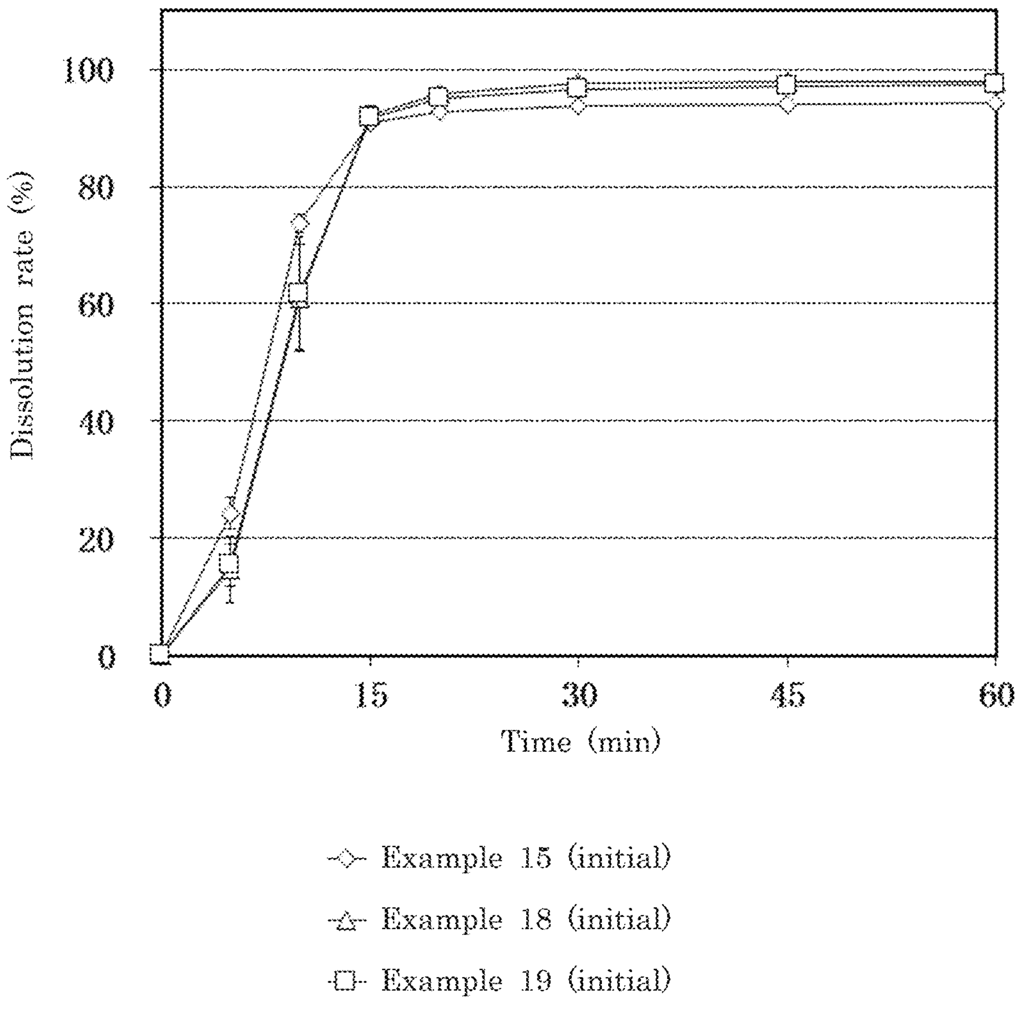
FIG. 7 shows dissolution profile of a 10 mg tablet containing triethyl citrate. The horizontal axis represents time (min), and the vertical axis represents a dissolution rate (%).

FIG. 7 shows a dissolution profile at the start of the stability testing for the samples of Examples 15, 18, and 19. The dissolution profiles of Examples 18 and 19 in which triethyl citrate was blended were equivalent to those of Example 15 in which triethyl citrate was not blended, and a decrease in dissolution due to blending of triethyl citrate was not confirmed.

In addition, the sample of Example 18 was stored under a condition of 60° C. glass bottle closed for 2 weeks (referred to as 60° C./closed/2 weeks in FIG. 8), a condition of 10° C. glass bottle closed for 1 month (referred to as 10° C./closed/month in FIG. 8), and a condition of 40° C./75% EH glass bottle opened for 1 month (referred to as 40° C. 75% RH/opened/1 month in FIG. 8), and then subjected to the dissolution test. This dissolution profile is shown in FIG.

8, and the change in the dissolution profile at the start of the stability testing was equivalent for all the stored products.

(Test Example 12) Evaluation of Tablet Hardness

Tablet hardness was evaluated for the samples of Examples 15 to 20, 21, and (Tablet hardness) Hardness was measured using a tablet hardness tester (TBH200 type, ERWEKA GmbH), and an average value of 2 to 10 tablets was calculated.

(Results)

A relationship between the compression pressure and the tablet hardness in Examples 15 to 20 is shown in FIG. 9, and a relationship between the compression pressure and the tablet hardness in Examples 15, 21, and 22 is shown in FIG. 10. In the triethyl citrate-containing tablet, the tablet hardness was almost constant regardless of the blending amount of triethyl citrate.

(Examples 26, 27-1 to 27-5) Production of 50 mg Tablet

A tablet containing 50 mg of the sample of Reference Example 4 and triethyl citrate was produced on a mortar scale, and the amount of the compound represented by Formula (III) in the product stored over time, the dissolution test, and the tablet physical properties were evaluated.

(Method for Producing Core Tablet)

The tablet was produced in the same manner as in the production of the 10 mg tablet in the formulation per tablet shown in Table 22.

TABLE 22

| | Example 26 | Example 27-1 | Example 27-2 | Example 27-3 | Example 27-4 | Example 27-5 |
|---|---|---|---|---|---|---|
| Blending amount of triethyl citrate (molar ratio to drug substance) | — | 0.02 | 0.05 | 0.1 | 0.2 | 0.3 |
| Compound represented by Formula (I) or the like | 50 | 50 | 50 | 50 | 50 | 50 |
| Triethyl citrate | — | 0.54 | 1.36 | 2.72 | 5.45 | 8.17 |
| Anhydrous lactose 24AN | 76 | 75.5 | 74.6 | 73.3 | 70.6 | 67.8 |
| Low-substituted hydroxypropylcellulose LH21 | 15 | 15 | 15 | 15 | 15 | 15 |
| Hydroxypropylcellulose SL | 7.5 | 7.5 | 7.5 | 7.5 | 7.5 | 7.5 |
| Vegetable magnesium stearate | 1.5 | 1.5 | 1.5 | 1.5 | 1.5 | 1.5 |
| Total of core tablet (mg) | 150 | 150 | 150 | 150 | 150 | 150 |

(Test Example 13) Stability Testing

The samples of Examples 26 and 27-1 to 27-5 were subjected to a stability testing under a condition of 60° C. glass bottle closed (referred to as 60° C. closed in Table 23), 40° C. glass bottle closed (referred to as 40° C. closed in Table 23), and 40° C./75% RH glass bottle opened (referred to as 40° C./75% RH opened in Table 23) to evaluate the content of the compound represented by Formula (III).

Preparation of a sample solution was performed by the following method, and preparation of a standard solution, a method for measuring a total amount of a related substance, and a calculation formula were confirmed in the same manner as in Test Example 10.

(Preparation of Sample Solution)

A sample solution was prepared by the following method.

Step 1: One tablet of a 50 mg tablet was added to a 50 mL volumetric flask.

Step 2: To Step 1 was added 10 mL of water, and the mixture was vigorously shaken for 10 minutes to disintegrate the tablet completely. The shaking time was extended as necessary.

Step 3: To Step 2 was added 25 mL of acetonitrile, and the mixture was vigorously shaken for 30 minutes.

Step 4: After cooling, acetonitrile was added to make exactly 50 mL, a part of the liquid was centrifuged at 13000 rpm for 10 minutes, and the supernatant was used as a sample solution.

(Results)

The samples of Examples 26 and 27-1 to 27-5 were stored under a condition of 60° C. glass bottle closed for 2 weeks, a condition of 40° C. glass bottle closed for 1 month, or a condition of 40° C./75% RH glass bottle opened, and the results of measurement of the amount of the compound represented by Formula (III) after storage are shown in Table 23. As a result, in the sample of Example 26 in which triethyl citrate was not blended, an increase in the amount of the compound represented by Formula (III) was observed, but in each of the tablets in which triethyl citrate was blended of Examples 27-1 to 27-5, an increase in the amount of the compound represented by Formula (III) was suppressed.

TABLE 23

| | Blending amount of triethyl citrate (molar ratio to drug substance) | Initial (ppm) | 60° C. closed (ppm) 2W | 40° C. closed (ppm) 1M | 40° C./75% RH opened (ppm) 1M |
|---|---|---|---|---|---|
| Example 26 | — | 4 | 10 | 8 | 4 |
| Example 27-1 | 0.02 | 2 | 2 | 3 | 3 |
| Example 27-2 | 0.05 | 2 | 2 | 2 | 3 |
| Example 27-3 | 0.1 | 1 | 2 | Not evaluated | Not evaluated |
| Example 27-4 | 0.2 | 2 | 2 | Not evaluated | Not evaluated |
| Example 27-5 | 0.3 | 3 | 2 | Not evaluated | Not evaluated |

(Test Example 14) Evaluation of Tablet Hardness

For Examples 27-1 to 27-3 in which triethyl citrate was blended, tablet hardness was evaluated in the same manner as in Test Example 12.

(Results)

A relationship between the compression pressure and the tablet hardness of Examples 27-1 to 27-3 is shown in FIG. 20.

A production method with a stirring granulator was studied below.

(Examples 28-1 to 35-2) Production of Tablet with Stirring Granulator

Based on the formulation that was a candidate from the results of studies on a mortar scale, scaling up to a stirring granulator and water for granulation were studied.

(Production Method)

Using the sample of Reference Example 4 as the compound represented by Formula (I) or the like, tablets (core tablets and film-coated tablets) containing 10 mg and 50 mg were produced in the formulation shown in Table 24.

TABLE 24

| | 10 mg tablet | 50 mg tablet |
|---|---|---|
| Compound represented by Formula (I) or the like | 10.0 | 50.0 |
| Triethyl citrate | 1.0 | 1.0 |
| Anhydrous lactose 24AN | 125.5 | 85.5 |
| Low-substituted hydroxypropylcellulose LH21 | 7.5 | 7.5 |
| Hydroxypropylcellulose SL | 4.5 | 4.5 |
| Vegetable magnesium stearate | 1.5 | 1.5 |
| Total of core tablet (mg) | 150.0 | 150.0 |
| OPADRY ORANGE 03A430007 | 5.6 | 5.6 |
| Triethyl citrate | 0.4 | 0.4 |
| Total of coating layer (mg) | 6.0 | 6.0 |
| Total | 156.0 | 156.0 |

The compound represented by Formula (I) or the like, anhydrous lactose 24AN (DFE Pharma GmbH & Co. KG), and low-substituted hydroxypropylcellulose LH21 (Shin-Etsu Chemical Co., Ltd.) were mixed, sieved with a 20-mesh wire mesh, and mixed with a high speed mixer (10 type, Fukae Kogyo Co., Ltd.) to obtain a mixture, Hydroxypropylcellulose SSL (Nippon Soda Co., Ltd.) and triethyl citrate (Merck KGaA) were dissolved in purified water, and the mixture was wet-granulated with a high speed mixer (10 type, Fukae Kogyo Co., Ltd.), The granulated product was sized with a power mill (SHOWA KAGAKUKIKAI CO., LTD., P-3S type), and dried with a fluidized bed granulator (2 type) (WSG 2 & 5 types, Freund Corporation) at an aeration temperature of 60° C., After drying, the particles were adjusted with a power mill (P-3 type, SHOWA KAGAKUKIKAI CO., LTD.). The sized granulated product and vegetable magnesium stearate (Mallinckrodt Pharmaceuticals plc) were mixed with a lubricant by bag mixing or bottle mixing, or with a mixer (8 L V-type), and tableting was performed with a static compressor (ABM100S type, manufactured by JT Toshi Co., Ltd.) or a tableting machine (LIBRA836BK-AWCZ type, KIKUSUI SEISAKUSHO LTD.).

The water for granulation at the time of granulation was changed to 17, 20, 22, and 25% (w/w) as shown in Table 25, the granulated product was sampled with each water for granulation, and the obtained granule was subjected to static compression to produce a core tablet (Examples 28-1, 29-1, 30-1, 31-1, 32-1, 33-1, 34-1, and 35-1).

The core tablet was coated with OPADRY ORANGE 03A30007 (Colorcon Japan LLC) and triethyl citrate (Merck KGaA) to produce a film-coated tablet (Examples 28-2, 29-2, 30-2, 31-2, 32-2, 33-2, 34-2, and 35-2). A coating film amount per tablet was 1% (w/w) (6.0 mg/tablet) with respect to a mass of the core tablet.

TABLE 25

| | Water for granulation % (w/w) | 17 | 20 | 22 | 25 |
|---|---|---|---|---|---|
| 10 mg tablet | Core tablet | Example 28-1 | Example 29-1 | Example 30-1 | Example 31-1 |
| | Film-coated tablet | Example 28-2 | Example 29-2 | Example 30-2 | Example 31-2 |
| 50 mg tablet | Core tablet | Example 32-1 | Example 33-1 | Example 34-1 | Example 35-1 |
| | Film-coated tablet | Example 32-2 | Example 33-2 | Example 34-2 | Example 35-2 |

Each condition is as follows.

(Mixing Conditions)

Mixer: 10 type high speed mixer

Agitator rotation speed: 250±20 $min^{-1}$

Mixing time: 0.5 to 1 minutes (Granulation Conditions)

Granulator: 10 type high speed mixer

Agitator rotation speed: 250±20 $min^{-1}$

Chopper rotation speed: 2500±100 $min^{-1}$

Water for granulation: 17 to 25%

Liquid injection speed: 83 to 94 g/min

Stirring time after liquid injection: 0.5 to 2 minutes

Massing time: 1 to 2 minutes±5 seconds (Sizing Conditions)

Sizing machine: P-3 type power mill

Basket: herringbone 2.5 mm

Rotation speed: 2,000±50 $min^{-1}$

Blade: spoiler blade (Drying Conditions)

Dryer: WSG 2 & 5 types fluidized bed granulator (2 type)

Air supply temperature: 60° C. (preset temperature)

Air supply dynamic pressure: 5 to 8 Pa

Bag filter: T611E

Loss on drying: 1.0% or less (Particle Adjusting Conditions)

Dryer: P-3 type power mill

Basket: Wire mesh 16 mesh

Rotation speed: 2000±50, 3000±50 $min^{-1}$

Blade: spoiler blade (Lubricant Mixing Condition 1)

Bag mixing/bottle mixing 10 times each left and right/10 times each up and down in bottle (Lubricant Mixing Condition 2)

Mixer: 8 L V-type mixer

Rotation speed: 40±1.0 $min^{-1}$

Mixing time: 1.1 to 3.2 minutes (Tableting Condition 1)

Tableting machine: ABM100S type static compressor

Punch: diameter of 7.0 mm, two-stage R (13×2.3), CrN coating

Load speed: 2.0 F.S./min (F.S.=10 kN)

Hold time: 1 second

Hold point: 3.5 kN to 9.0 kN (Tableting Condition 2)

Tableting machine: LIBRA836BK-AWCZ type tableting machine

Punch: diameter of 7.0 mm, two-stage R (13×2.3), CrN coating

Number of punches: 6

Rotation speed: 30±2.0 $min^{-1}$

Feed shoe: open (Covering Condition 1)

Dryer: HCT48 type HICOATER

Charge: about 2.5 kg

Air blowing temperature: 60° C. (preset temperature)

Air supply volume (differential pressure): 300 Pa

Air exhaust volume (differential pressure): 150 Pa

Spray air volume: about 80 NL/min

Spray pressure: 0.8 MPa

Cap: 120SS, nozzle: 2850

Pan rotation speed: 20 $min^{-1}$

Liquid velocity: 10 to 14 g/min

Spray distance: about 13 to 16 cm to tablet surface

End point of coating: average mass increase of tablet of 5.5 mg or more (Covering Condition 2)

AQC-48 type AQUA COATER

Charge: about 2.5 to 4.0 kg

Air blowing temperature: 47 to 65° C. (preset temperature)

Air supply volume: 3.5±0.5 $m^3$/min

Static pressure in pan: 0 Pa or less

Spray pressure: 0.5±0.1 MPa

Flow meter display: 108±40 NL/min

Spray gun: NAT-2 type, 1 spray gun (nozzle cap type number: 0.15, nozzle diameter: 1.0 mm)

Pan rotation speed: 6 to 15 $min^{-1}$

Liquid velocity: 8 to 16 g/min

Spray distance: about 16 cm to tablet surface

End point of coating: average mass increase of tablet of 5.5 mg or more (Test Example 15) Stability Testing of Tablet Tablets were packaged in a glass bottle, a DUMA bottle (plastic container, Gerresheimer AG), and a DUMA bottle containing silica gel, and subjected to a stability testing at 60° C. and 40° C./75% RIH.

The content of the compound represented by Formula (III) was confirmed in the same manner as in Test Example 10 or Test Example 13.

(Results)

For Examples 29-1, 29-2, 31-1, 31-2, 33-1, 33-2, 35-1, and 35-2, the amount (ppm) of the compound represented by Formula (III) of products stored under a condition of 60° C. closed for 2 weeks and a condition of 40° C. for 2 months are shown in Tables 26 and 27. As a result, the amount of the compound represented by Formula (III) was increased by 4 ppm at the maximum from the start of the test, and the stabilization effect was confirmed even in scale-up. Regarding the water for granulation, an increase in the amount of the compound represented by Formula (ITI) was more suppressed when the water for granulation was 25% (w/w) than when the water for granulation was 20% (w/w), but the stabilization effect was confirmed for any water for granulation. In comparison of the packaging form, no clear effect was observed. In addition, in the core tablet and the film-coated tablet, the amount of the compound represented by Formula (11) was equivalent.

From the results of Test Examples 7, 9, 10, 13, and 15 it was confirmed that in a stability testing under a condition of 40±2° C. and a relative humidity of 75±5% (glass bottle closed, glass bottle opened, DUMA bottle, and DUMA bottle containing silica gel) for 1 month and 2 months, the pharmaceutical composition of the present invention has a content ratio of the compound represented by Formula (III) to the amount of the compound represented by Formula (I) or the like of 0.0001 to 10 ppm. Furthermore, it is considered that also in a stability testing under a condition of 40±2° C. and a relative humidity of 75±5% (glass bottle closed, glass bottle opened, DUMA bottle, and DUMA bottle containing silica gel) for 6 months, the pharmaceutical composition of the present invention has a content ratio of the compound represented by Formula (III) to the amount of the compound represented by Formula (I) or the like of 0.0001 to 30 ppm.

TABLE 26

| Storage conditions | Packaging form | Storage period | Example 29-1 (core tablet) | Example 29-2 (film-coated tablet) | Example 31-1 (core tablet) | Example 31-2 (film-coated tablet) |
|---|---|---|---|---|---|---|
| — | — | Initial | 2 | 2 | 2 | 2 |
| 60° C. | Glass bottle closed | 2W | 3 | 3 | 3 | 4 |
| | DUMA bottle | 2W | 4 | 3 | 3 | 3 |
| | DUMA bottle + silica gel | 2W | 3 | 3 | 3 | 2 |
| 40° C./ 75% RH | Glass bottle closed | 1M | 3 | 4 | 2 | 3 |
| | | 2M | 4 | 4 | 4 | 3 |
| | Glass bottle opened | 1M | 3 | 3 | 3 | 3 |
| | | 2M | 4 | 4 | 4 | 3 |
| | DUMA bottle | 1M | 3 | 3 | 3 | 3 |
| | | 2M | 4 | 4 | 3 | 3 |
| | DUMA bottle + silica gel | 1M | 3 | 3 | 2 | 2 |
| | | 2M | 4 | 5 | 4 | 3 |

TABLE 27

| Storage conditions | Packaging form | Storage period | Example 33-1 (core tablet) | Example 33-2 (film-coated tablet) | Example 35-1 (core tablet) | Example 35-2 (film-coated tablet) |
|---|---|---|---|---|---|---|
| — | — | Initial | 2 | 2 | 2 | 2 |
| 60° C. | Glass bottle closed | 2W | 4 | 4 | 3 | 4 |
| | DUMA bottle | 2W | 5 | 4 | 3 | 3 |
| | DUMA bottle + silica gel | 2W | 4 | 4 | 2 | 3 |
| 40° C./ 75% RH | Glass bottle closed | 1M | 4 | 4 | 3 | 3 |
| | | 2M | 5 | 4 | 4 | 3 |
| | Glass bottle opened | 1M | 4 | 4 | 3 | 3 |
| | | 2M | 6 | 4 | 4 | 4 |
| | DUMA | 1M | 5 | 4 | 4 | 3 |

TABLE 27-continued

| Storage conditions | Packaging form | Storage period | Example 33-1 (core tablet) | Example 33-2 (film-coated tablet) | Example 35-1 (core tablet) | Example 35-2 (film-coated tablet) |
|---|---|---|---|---|---|---|
| | bottle | 2M | 6 | 5 | 4 | 4 |
| | DUMA | 1M | 4 | 4 | 3 | 2 |
| | bottle + silica gel | 2M | 6 | 6 | 4 | 4 |

(Test Example 16) Dissolution Test (Influence of Water for Granulation)

For the samples of Examples 28-1, 29-1, 30-1, and 31-1 (10 mg tablets) and Examples 32-1, 33-1, 34-1, and 35-1 (50 mg tablets) in which water for granulation was changed, a dissolution test was performed in the same manner as the dissolution test method of the formulation of Test Example 11.

(Results)

The dissolution profiles of Examples 28-1, 29-1, 30-1, and 31-1 (10 mg tablets) are shown in FIG. 12, and the dissolution profiles of Examples 32-1, 33-1, 34-1, and 35-1 (50 mg tablets) are shown in FIG. 13. In any water for granulation, rapid dissolution of 90% or more was exhibited in 15 minutes, and an influence of a difference in water for granulation on the dissolution was small.

(Test Example 17) Dissolution Test (Influence of Coating)

For the samples of Examples 29-1, 29-2, 33-1, and 33-2 in which water for granulation is 20% (w/w) and Examples 31-1, 31-2, 35-1, and 35-2 in which water for granulation is 25% (w/w), a dissolution test was performed in the same manner as the dissolution test method of the formulation of Test Example 11.

(Results)

The dissolution profiles of Examples 29-1, 29-2, 31-1, and 31-2 are shown in FIG. 14, and the dissolution profiles of Examples 33-1, 33-2, 35-1, and 35-2 are shown in FIG. 15. In both the 10 mg tablet and the 50 mg tablet, an influence of coating on dissolution was small.

INDUSTRIAL APPLICABILITY

In a crystal of the compound represented by Formula (I) or the like obtained by wet pulverization, production of the compound represented by Formula (III) in a stability testing is suppressed, and the stability is improved. By using the crystal of the compound represented by Formula (I) or the like obtained by wet pulverization the pharmaceutical composition of the present invention having excellent stability can be supplied. In addition, the pharmaceutical composition of the present invention adjusted by wet-kneading and/or wet-granulating the compound represented by Formula (I) or the like can suppress production of the compound represented by Formula (III) in a stability testing, and the stability is improved. In that respect, the present invention has industrial applicability.

The invention claimed is:

1. A method for producing a pharmaceutical composition containing a compound represented by Formula (I):

[Chemical Formula 1]

(I)

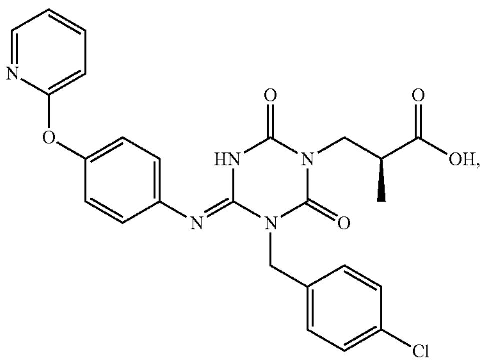

a pharmaceutically acceptable salt thereof, or a solvate thereof, the method comprising:

a step of wet-pulverizing the compound represented by Formula (I), the pharmaceutically acceptable salt thereof, or the solvate thereof; and/or a step of wet-kneading and/or wet-granulating the compound represented by Formula (I), the pharmaceutically acceptable salt thereof, or the solvate thereof.

2. The method according to claim 1, the method comprising a step of wet-kneading and/or wet-granulating the compound represented by Formula (I), the pharmaceutically acceptable salt thereof, or the solvate thereof.

3. The method according to claim 2, wherein the pharmaceutical composition does not contain a compound represented by Formula (III):

[Chemical Formula 2]

(III)

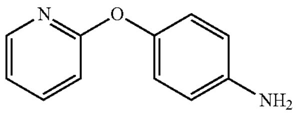

or contains the compound represented by Formula (III) and has a content ratio of the compound represented by Formula (III) to an amount of the compound represented by Formula (I), the pharmaceutically acceptable salt thereof, or the solvate thereof of 0.0001 to 10 ppm.

4. The method according to claim 3, wherein when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I), the pharmaceutically acceptable salt thereof, or the solvate thereof is 0.0001 to 10 ppm.

5. The method according to claim 2, wherein the compound represented by Formula (I), the pharmaceutically acceptable salt thereof, or the solvate thereof used for the wet kneading and/or the wet granulation is obtained by dry pulverization.

6. The method according to claim 1, the method comprising a step of wet-pulverizing the compound represented by Formula (I), the pharmaceutically acceptable salt thereof, or the solvate thereof.

7. A pharmaceutical composition, comprising a compound represented by Formula (I):

[Chemical Formula 1]

(I)

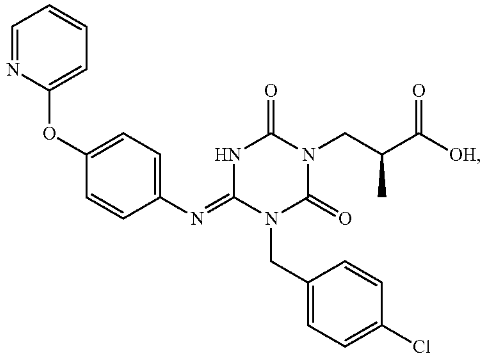

a pharmaceutically acceptable salt thereof, or a solvate thereof, the pharmaceutical composition being obtained by the method for producing the pharmaceutical composition according to claim 1.

8. The pharmaceutical composition according to claim 7, which does not comprise a compound represented by Formula (III):

[Chemical Formula 4]

(III)

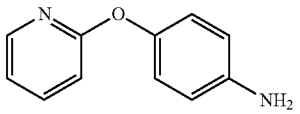

or comprises the compound represented by Formula (III) and has a content ratio of the compound represented by Formula (III) to an amount of the compound represented by Formula (I), the pharmaceutically acceptable salt thereof, or the solvate thereof of 0.0001 to 10 ppm.

9. The pharmaceutical composition according to claim 8, wherein when a stability testing is performed under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I), the pharmaceutically acceptable salt thereof, or the solvate thereof is 0.0001 to 10 ppm.

10. A pharmaceutical composition, comprising a compound represented by Formula (I):

[Chemical Formula 1]

(I)

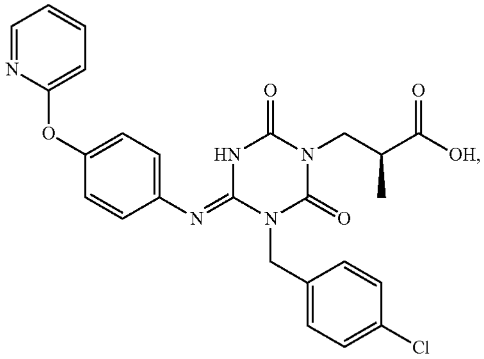

a pharmaceutically acceptable salt thereof, or a solvate thereof, the pharmaceutical composition being a tablet or a granule and containing a hydroxycarboxylic acid ester, a polyhydric alcohol ester, and/or a polyether in a core tablet or an uncoated granule.

11. The pharmaceutical composition according to claim 10, wherein one or more selected from the group consisting of triethyl citrate, miglyol, triacetin, macrogol 6000, polysorbate 20, polysorbate 60, polysorbate 80, sesame oil, corn oil, olive oil, and soybean oil are contained in the core tablet or the uncoated granule.

12. The pharmaceutical composition according to claim 11, wherein one or more selected from the group consisting of triethyl citrate, miglyol, and triacetin are contained in the core tablet or the uncoated granule.

13. The pharmaceutical composition according to claim 12, wherein triethyl citrate is contained in the core tablet or the uncoated granule.

14. The pharmaceutical composition according to claim 10, wherein an amount of the hydroxycarboxylic acid ester, the polyhydric alcohol ester, and/or the polyether is 0.01 to 10% by weight based on a total amount of the tablet or the granule.

15. The pharmaceutical composition according to claim 10, wherein the amount of the hydroxycarboxylic acid ester, the polyhydric alcohol ester, and/or the polyether is 0.0001 to 0.5 parts by weight based on 1 part by weight of the compound represented by Formula (I), the pharmaceutically acceptable salt thereof, or the solvate thereof.

16. The pharmaceutical composition according to claim 10, comprising one or more selected from the group consisting of lactose, low-substituted hydroxypropylcellulose, and hydroxypropylcellulose.

17. A method for producing a crystal of a compound represented by Formula (I):

[Chemical Formula 6]

(I)

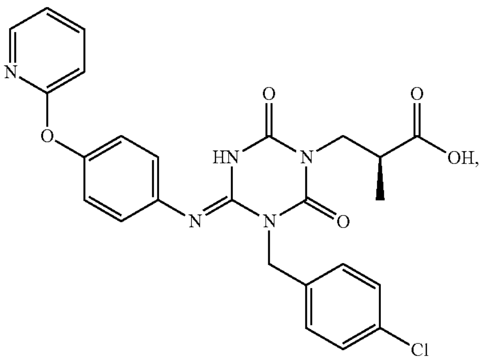

a pharmaceutically acceptable salt thereof, or a solvate thereof, characterized by wet-pulverizing the compound represented by Formula (I), the pharmaceutically acceptable salt thereof, or the solvate thereof.

18. The method according to claim 17, wherein the crystal obtained does not contain a compound represented by Formula (III):

[Chemical Formula 2]

(III)

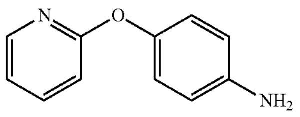

or contains the compound represented by Formula (III) and has a content ratio of the compound represented by Formula (III) to an amount of the compound represented by Formula (I), the pharmaceutically acceptable salt thereof, or the solvate thereof of 0.0001 to 10 ppm.

19. The method according to claim 18, wherein when the crystal obtained is subjected to a stability testing under a condition of 40±2° C. and a relative humidity of 75±5% (glass bottle opened) for 1 month, the compound represented by Formula (III) is not detected, or the content ratio of the compound represented by Formula (III) to the amount of the compound represented by Formula (I), the pharmaceutically acceptable salt thereof, or the solvate thereof is 0.0001 to 10 ppm.

20. The method according to claim 17, wherein a 90% particle size distribution of the crystal obtained is 100 μm or less.

21. The method according to claim 17, wherein the crystal obtained is an anhydrate crystal of the compound represented by Formula (I).

22. The method according to claim 17, characterized by wet-pulverizing an anhydrate crystal and/or an amorphous substance of the compound represented by Formula (I).

23. The method according to claim 17, characterized by wet-pulverizing a supersaturated solution.

24. The method according to claim 23, comprising:

a step of forming a nucleus of a crystal from the supersaturated solution;

a step of crystal-growing the nucleus obtained in the step;

a step of controlling nucleation and crystal growth; and a step of refining the crystal.

25. The method according to claim 24, comprising:

a step of producing a dihydrate crystal of the compound represented by Formula (I) from the supersaturated solution;

a step of producing an anhydrate crystal of the compound represented by Formula (I) from the crystal obtained in the step; and a step of controlling a 90% particle size distribution of the crystal obtained in the step to be 100 μm or less.

26. The method according to claim 25, wherein the step of producing a dihydrate crystal of the compound represented by Formula (I) from the supersaturated solution is performed at 25±5° C.

27. The method according to claim 25, wherein the step of producing an anhydrate crystal of the compound represented by Formula (I) from the dihydrate crystal of the compound represented by Formula (I) includes a step of heating and cooling.

28. The method according to claim 17, wherein a solvent in a step of the wet-pulverizing contains one or more solvents selected from the group consisting of water, methanol, and 2-propanol.

29. A crystal of a compound represented by Formula (I):

[Chemical Formula 1]

(I)

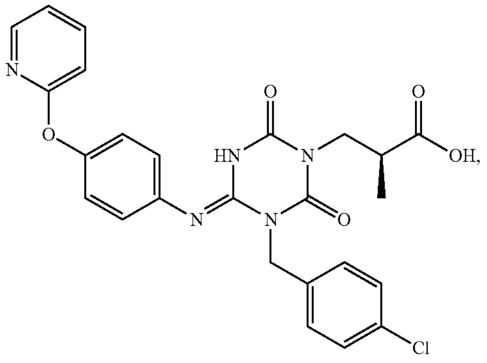

a pharmaceutically acceptable salt thereof, or a solvate thereof, the crystal being obtained by the method according to claim 17.

30. The crystal according to claim 29, which does not comprise a compound represented by Formula (III):

[Chemical Formula 2]

(III)

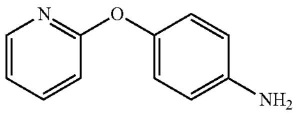

or comprises the compound represented by Formula (III) and has a content ratio of the compound represented by Formula (III) to an amount of the compound represented by Formula (I), the pharmaceutically acceptable salt thereof, or the solvate thereof of 0.0001 to 10 ppm.

31. The crystal according to claim 30, wherein when a stability testing is performed under a condition of 40±2° C.

and a relative humidity of 75±5% (glass bottle opened) for 1 month, the compound represented by Formula (III) is not detected, or the content ratio of the compound represented by Formula (III) to the amount of the compound represented by Formula (I), the pharmaceutically acceptable salt thereof, or the solvate thereof is 0.0001 to 10 ppm.

32. The crystal according to claim 29, which is an anhydrate crystal of the compound represented by Formula (I).

33. The crystal according to claim 32, which exhibits characteristic X-ray powder diffraction peaks at diffraction angles (2θ) of 15.8±0.2°, 19.4±0.2°, 21.7±0.2°, 23.9±0.2°, and 25.4±0.2° or diffraction angles (2θ) of 7.9±0.2°, 9.3±0.2°, 12.9±0.2°, 15.8±0.2°, and 19.4±0.20.

34. A method for analyzing a related substance in a sample, the method comprising:

a) a step of using a crystal of a compound represented by Formula (I):

[Chemical Formula 10]

(I)

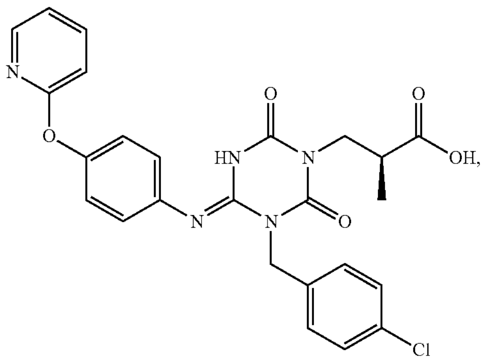

a pharmaceutically acceptable salt thereof, or a solvate thereof, or a pharmaceutical composition containing the compound represented by Formula (I), the pharmaceutically acceptable salt thereof, or the solvate thereof as the sample, and performing chromatographic analysis on the sample; and b) a step of obtaining a content or a content ratio of a compound represented by Formula (III):

[Chemical Formula 11]

(III)

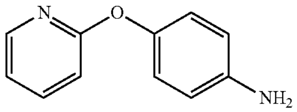

in the chromatographic analysis obtained in the above step.

35. A method for analyzing a content or a content ratio of a compound represented by Formula (III):

[Chemical Formula 13]

(III)

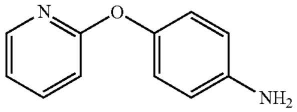

in a crystal of a compound represented by Formula (I):

[Chemical Formula 10]

(I)

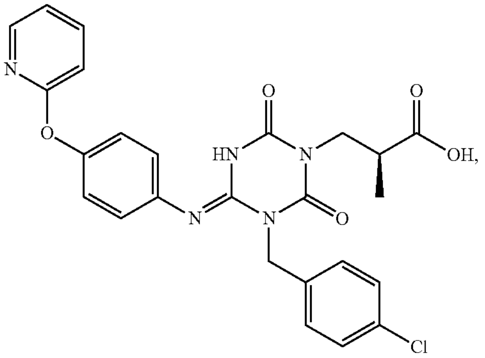

a pharmaceutically acceptable salt thereof, or a solvate thereof, or a pharmaceutical composition containing the compound represented by Formula (I), the pharmaceutically acceptable salt thereof, or the solvate thereof, wherein the compound represented by Formula (III) is used as a standard sample.

* * * * *